(12) United States Patent
Jasti et al.

(10) Patent No.: US 11,739,178 B2
(45) Date of Patent: Aug. 29, 2023

(54) NANOHOOP-FUNCTIONALIZED POLYMER EMBODIMENTS AND METHODS OF MAKING AND USING THE SAME

(71) Applicant: University of Oregon, Eugene, OR (US)

(72) Inventors: Ramesh Jasti, Eugene, OR (US); Ruth Maust, Eugene, OR (US); Penghao Li, Evanston, IL (US)

(73) Assignee: University of Oregon, Eugene, OR (US)

( * ) Notice: Subject to any disclaimer, the term of this patent is extended or adjusted under 35 U.S.C. 154(b) by 232 days.

(21) Appl. No.: 17/033,376

(22) Filed: Sep. 25, 2020

(65) Prior Publication Data

US 2021/0095069 A1    Apr. 1, 2021

Related U.S. Application Data

(60) Provisional application No. 62/907,118, filed on Sep. 27, 2019.

(51) Int. Cl.
*C08G 61/10* (2006.01)
*C08J 3/24* (2006.01)

(52) U.S. Cl.
CPC .............. *C08G 61/10* (2013.01); *C08J 3/24* (2013.01); *C08J 2365/02* (2013.01)

(58) Field of Classification Search
CPC .............. C08G 61/126; C08G 61/10; C08G 2261/124; C08G 2261/1412; C08G 2261/148; C08G 2261/312; C08G 2261/3229; C08G 2261/3328; C08G 2261/42; C07C 15/14
See application file for complete search history.

(56) References Cited

U.S. PATENT DOCUMENTS

| | | | |
|---|---|---|---|
| 8,461,403 | B2 | 6/2013 | Jasti et al. |
| 8,895,768 | B2 | 11/2014 | Yamago |
| 9,090,473 | B2 | 7/2015 | Jasti et al. |
| 9,481,618 | B2 | 11/2016 | Itami et al. |
| 9,527,737 | B2 | 12/2016 | Itami et al. |
| 2011/0166390 | A1 | 7/2011 | Jasti et al. |
| 2012/0220790 | A1 | 8/2012 | Yamago |
| 2016/0372684 | A1 | 12/2016 | Jasti et al. |
| 2018/0290952 | A1 | 10/2018 | Jasti et al. |
| 2019/0025315 | A1 | 1/2019 | Jasti et al. |
| 2020/0010419 | A1 | 1/2020 | Jasti et al. |

OTHER PUBLICATIONS

Kwan et al. (J. Am. Chem. Soc. 2004, 126, 8638-8639).*

(Continued)

*Primary Examiner* — Shane Fang
(74) *Attorney, Agent, or Firm* — Klarquist Sparkman, LLP

(57) ABSTRACT

Disclosed herein are embodiments of a nanohoop-functionalized polymer and methods of making and using the same. In particular embodiments, polymer comprises one or more nanohoops that extend from the polymer backbone. Also disclosed herein are polymerizable nanohoop monomer embodiments that can be used to make the polymer embodiments disclosed herein.

16 Claims, 27 Drawing Sheets

(56) References Cited

OTHER PUBLICATIONS

Ball et al., "Stepping into the Light: Conjugated Macrocycles with Donor-Acceptor Motifs," ACS Cent. Sci., 1, 416-417, Oct. 27, 2015.
Darzi et al., "Selective syntheses of [7]-[12]Cycloparaphenylenes using orthogonal Suzuki-Miyaura cross-coupling reactions," Journal of Organic Chemistry, vol. 77, pp. 6624-6628, Jul. 17, 2012.
Darzi et al., "Synthesis, Properties, and Design Principles of Donor-Acceptor Nanohoops," ACS Central Science, vol. 1, pp. 335-342, Sep. 3, 2015.
Darzi et al., "The dynamic, size-dependent properties of [5]-[12]cycloparaphenylenes," Chem. Soc. Rev., vol. 44, pp. 6401-6410, Apr. 27, 2015.
Darzi, Research Presentation/Slides, Sep. 24, 2014.
Final Office Action issued for U.S. Appl. No. 16/041,676 dated Aug. 27, 2020.
Final Office Action issued for U.S. Appl. No. 15/187,644 dated Aug. 19, 2020.
Havinga et al., "A new class of small band gap organic polymer conductors," Polymer Bulletin, 29(119): 119-126, Aug. 1992.
Hirst "Synthesis of Nitrogen-Substituted Cycloparaphenylenes," Dissertation, May 2014.
Hirst "Synthesis of Nitrogen-Substituted Cycloparaphenylenes," Thesis Defense Presentation, May 13, 2014.
Ishii et al., "Synthesis and dimerization of chloro[10]cyclopharaphenylene: A directly connected cycloparaphenylene dimer," Organic Letters, 16(8): 2174-2176, Apr. 1, 2014.
Iwamoto et al., "Selective and Random Syntheses of [n]Cycloparaphenylenes (n = 8-13) and Size Dependence of Their Electronic Properties," Journal of the American Chemical Society, 133(21): 8354-8361, May 4, 2011.
Iwamoto et al., "Size-Selective Encapsulation of $C_{60}$ by [10]Cycloparaphenylene: Formation of the Shortest Fullerene-Peapod," Agnew. Chem. Int. Ed., vol. 50, pp. 8342-8344, Jul. 18, 2011.
Jasti et al., "Synthesis, Characterization, and Theory of [9]-, [12]-, and [18]Cycloparaphenylene: Carbon Nanohoop Structures," J. Am. Chem. Soc., vol. 130, pp. 17646-17647, Dec. 4, 2008.
Kikuchi et al., "Definitive evidence for the contribution of biradical character in a closed-shell molecule, derivative of 1,4-Bis-(4,5-diphenylimidazol-2-ylidene)cyclohexa-2,5,-diene," JACS Communications, 126(21): 6526-6527, May 11, 2004.
Kubota et al., "η6-cycloparaphenylene transition metal complexes: synthesis, structure, photophysical properties, and application to the selective monofunctionalization of cycloparaphenylenes," JACS,vol. 137, pp. 1356-1361, Jan. 12, 2015.
Kuwabara et al., "Curved oligophenylenes as donors in shape-persistent donoracceptor macrocycles with solvatofluorochromic properties," Angew. Chem. Int. Ed., 54(33): 9646-9649, Aug. 10, 2015.
Matsui et al., "Synthesis and properties of cycloparaphenylene-2,5-pyridylidene: a nitrogen-containing carbon nanoring," Organic Letters, 14(7): 1888-1891, Mar. 23, 2012.
Mutoh et al., "Entropy-controlled biradical-quinoid isomerization of a π-conjugated delocalized biradical," Phys. Chem. Chem. Phys., 17(2): 1151-1155, Nov. 17, 2014.
Nishihara et al., "Excited states in cycloparaphenylenes: dependence of optical properties on ring length," Journal of Physical Chemistry Letters, vol. 3, pp. 3125-3128, Oct. 12, 2012.
Non-Final Office Action issued for U.S. Appl. No. 16/041,676 dated Feb. 6, 2020.
Oki et al., "One-pot synthesis of a rice-ball-shaped cyclophane with syn-diethanoanthracene-fused dipyrrole and hexafluorobenzene," Chem. Lett., vol. 46, pp. 243-244, Nov. 26, 2016.
Ozasa et al., "Studies of polyphenyls and polyphenylenes. II. The synthesis and physical properties of polyphenyls containing para linkage," Bull. Chem. Soc. Jpn., 53(9): 2610-2617, 1980.
Rio et al., "Cyclotetrahalo-p-phenylenes: simulations of halogen substituted cycloparaphenylenes and their interaction with $C_{60}$," Phys. Chem. Chem. Phys., 18(33): 23257-23263, Jul. 22, 2016.
Salvatella, "The alkyl group is a −I + R substituent," Educacion Quimica, vol. 28, pp. 232, 237, Jul. 17, 2017.
Takase et al., "Donor-acceptor segregated paracyclophanes composed of naphthobipyrrole and stacked fluoroarenes," Organic Letters, 15(13): 3202-3205, Jun. 21, 2013.
Xia et al., "Gram-scale synthesis and crystal structures of [8]- and [10]CPP, and the solid-state structure of $C_\alpha$@[10]CPP," Chemical Science, vol. 3, pp. 3018-3021, Jul. 11, 2012.
Xia et al., "Synthesis, Characterization and Computational Studies of Cycloparaphenylene Dimers," J. Am. Chem. Soc., 134(48): 19709-19715, Nov. 6, 2012.
Xue et al., "Cyclo-meta-phenylene revisited: nickel-mediated synthesis, molecular structures, and device applications," Journal of Organic Chemistry, vol. 79, pp. 9735-9739, pp. 9735-9739, Sep. 29, 2014.
Zhang et al., "Giant Cyclo[n]thiophenes with Extended π Conjugation," Angewandte Chemie Int. Ed., 48(36): 6632-6635, Jun. 27, 2009.

\* cited by examiner

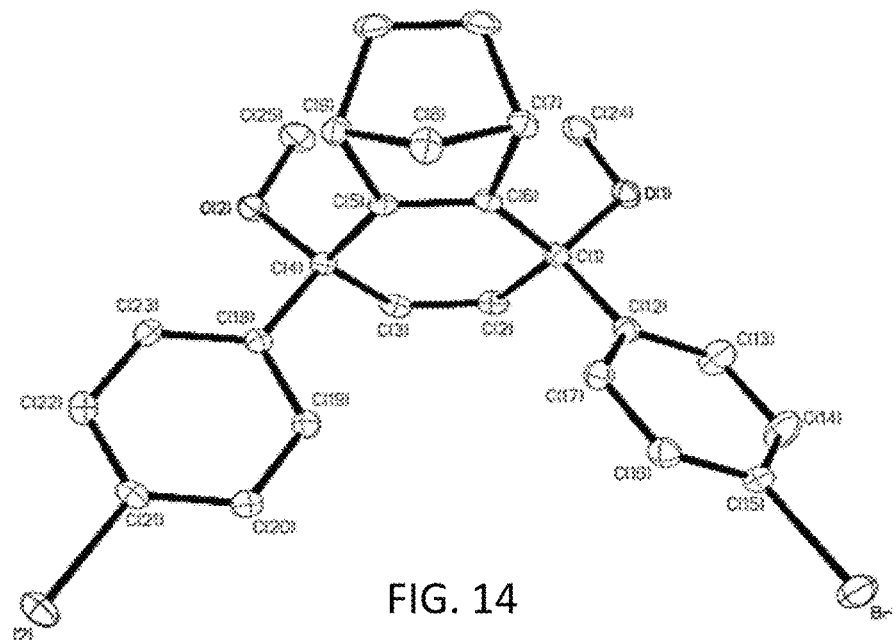
FIG. 14
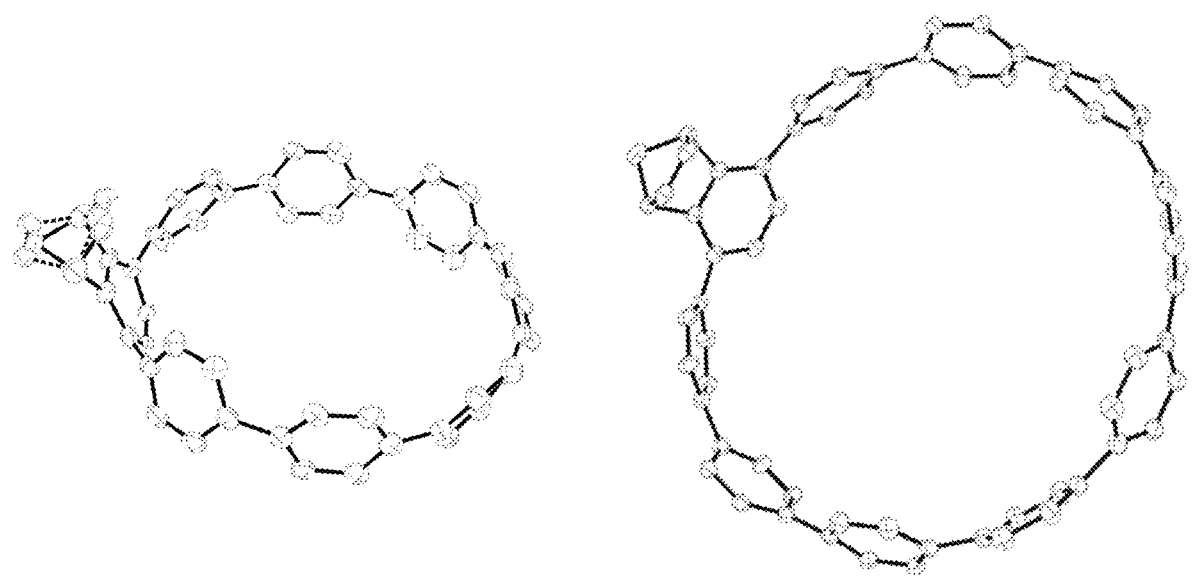
FIG. 15
FIG. 16

NANOHOOP-FUNCTIONALIZED POLYMER EMBODIMENTS AND METHODS OF MAKING AND USING THE SAME

CROSS REFERENCE TO RELATED APPLICATION

This application claims the benefit of the earlier filing date of U.S. Provisional Patent Application No. 62/907,118, filed on Sep. 27, 2019; the entirety of this prior application is incorporated by reference herein.

ACKNOWLEDGMENT OF GOVERNMENT SUPPORT

This invention was made with government support under Contract No. DE-SC0019017 awarded by the Department of Energy. The government has certain rights in the invention.

FIELD

Disclosed herein are embodiments of a nanohoop-functionalized polymer and methods of making and using the same.

BACKGROUND

Over the years, polymer chemistry has enabled making polymers with complex architectures; however, macrocycle-based polymers are more difficult to make and are thus far limited to using cyclodextrins. Macrocycle-based polymers have the potentiality to demonstrate distinct advantages over polymers made up of acyclic units and have the possibility of providing properties intrinsic to each type of macrocyclic unit in the polymer. There is a need in the art for new macrocycle-based polymers, such as polymers comprising cycloparaphenylenes, and methods of making the same.

SUMMARY

Disclosed herein are embodiments of a polymer comprising nanohoop "side arms" that extend from a polymer backbone. Also disclosed herein are polymerizable nanohoop monomers that can be used to make the polymer embodiments. Methods of making and using the polymer embodiments also are disclosed. Representative formulas for the polymer compound embodiments are disclosed herein. In some embodiments, the polymer has a structure satisfying Formula I

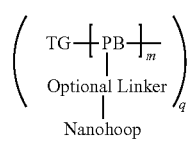

Formula I wherein PB is a polymer backbone; TG is a terminating group; the optional linker is selected from aliphatic, heteroaliphatic, haloaliphatic, haloheteroaliphatic, aromatic, or an organic functional group; the nanohoop comprises six or more aromatic ring systems and wherein each aromatic ring is bound to at least two other rings of the nanohoop by two separate single covalent bonds positioned para, ortho, or meta relative to one another; m is an integer ranging from two or greater; and q is an integer selected from 1 or 2.

Also disclosed herein are embodiments of a polymerizable nanohoop monomer. Representative formulas for such monomers are disclosed herein. In some embodiments, the polymerizable nanohoop monomer has a structure according to Formula V

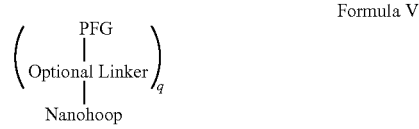

Formula V wherein each PFG independently is a polymerizable functional group; the optional linker is selected from aliphatic, heteroaliphatic, haloaliphatic, haloheteroaliphatic, aromatic, or an organic functional group; the nanohoop comprises six or more aromatic ring systems and wherein each aromatic ring is bound to at least two other rings of the nanohoop by two separate single covalent bonds positioned para, ortho, or meta relative to one another; and q is 1 or 2.

Representative method embodiments for making the polymerizable nanohoop monomer embodiments, as well as the polymer embodiments, also are disclosed herein.

The foregoing and other objects and features of the present disclosure will become more apparent from the following detailed description, which proceeds with reference to the accompanying figures.

BRIEF DESCRIPTION OF THE DRAWINGS

FIG. 14 is an ORTEP representation of the X-ray crystallographic structure of intermediate 402.

FIG. 15 is an ORTEP representation of the X-ray crystallographic structure of polymerizable nanohoop monomer 408.

FIG. 16 is an ORTEP representation of the X-ray crystallographic structure of polymerizable nanohoop monomer 504.

DETAILED DESCRIPTION

I. OVERVIEW OF TERMS

Figure 1:
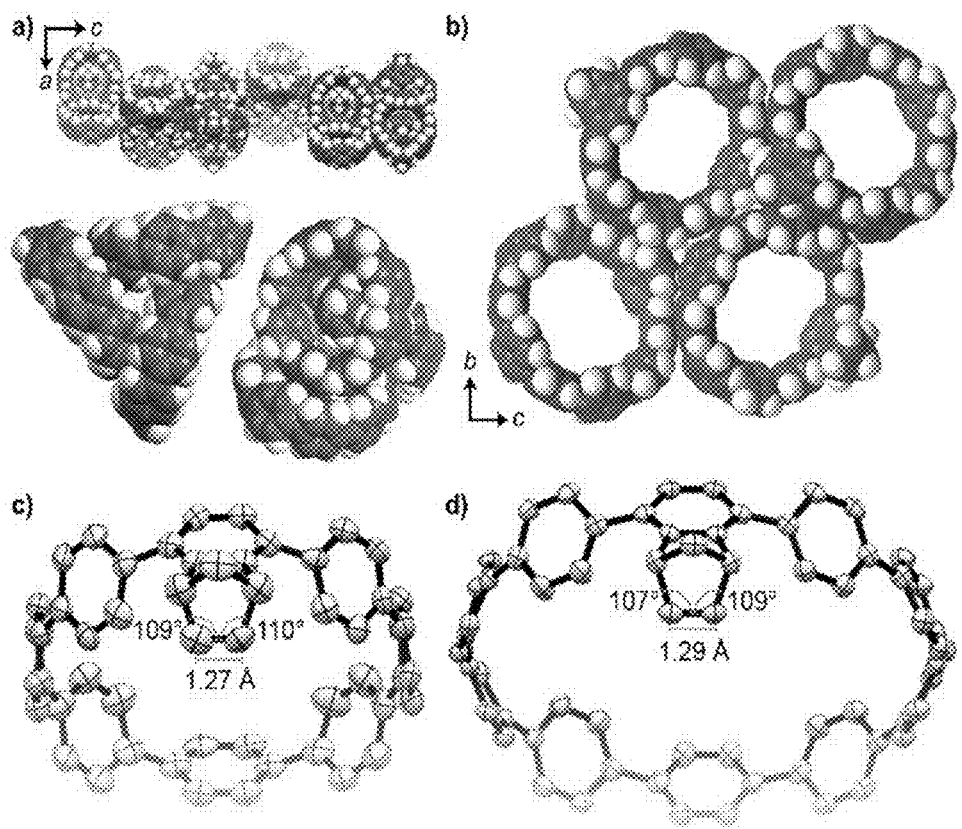
FIG. 1 shows images illustrating that the unit cell for polymerizable nanohoop monomer 408 contains 18 CPP-NB molecules, comprising six unique trimers, with one trimer shown individually in two different views (image "a") and that the unit cell for polymerizable nanohoop monomer 504 contains four CPP-NB molecules (image "b"); as well as images showing the norbornene alkene in the crystal structures of polymerizable nanohoop monomer 408 (image "c") and polymerizable nanohoop monomer 504 (image "d"), which illustrate that the norbornene moiety is largely unaffected by the number of rings in the hoop.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/ methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "—" which is used to show how the defined functional group attaches to, or within, the compound to which it is bound. Also, a dashed bond (i.e., "———") as used in certain formulas described herein indicates an optional bond (that is, a bond that may or may not be present). A person of ordinary skill in the art would recognize that the definitions provided below and the compounds and formulas included herein are not intended to include impermissible substitution patterns (e.g., methyl substituted with 5 different groups, and the like). Such impermissible substitution patterns are easily recognized by a person of ordinary skill in the art. In formulas and compounds disclosed herein, a hydrogen atom is present and completes any formal valency requirements (but may not necessarily be illustrated) wherever a functional group or other atom is not illustrated. For example, a phenyl ring that is drawn as

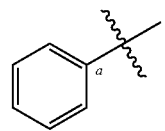 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well. An aliphatic group is distinct from an aromatic group.

Aliphatic-aromatic: An aromatic group that is or can be coupled to a compound disclosed herein, wherein the aromatic group is or becomes coupled through an aliphatic group.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, such as —O-alkyl, —O-alkenyl, —O-alkynyl; with exemplary embodiments including, but not limited to, methoxy, ethoxy, n-propoxy, isopropoxy, n-butoxy, t-butoxy, sec-butoxy, n-pentoxy (wherein any of the aliphatic components of such groups can comprise no double or triple bonds, or can comprise one or more double and/or triple bonds).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or —NR$^a$C(O)R$^b$ wherein each of R$^a$ and R$^b$ independently is selected from hydrogen, aliphatic, heteroaliphatic, haloaliphatic, haloheteroaliphatic, aromatic, or an organic functional group.

Amino: —NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized Tr-electron system. Typically, the number of out of plane Tr-electrons corresponds to the Hückel rule (4n +2). The point of attachment to the parent structure typically is through an aromatic portion of the condensed ring system. For example,

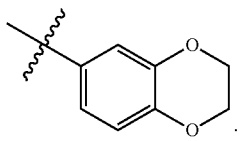 [SMILES: *c1ccc2c(c1)OCCO2]

However, in certain examples, context or express disclosure may indicate that the point of attachment is through a non-aromatic portion of the condensed ring system. For example,

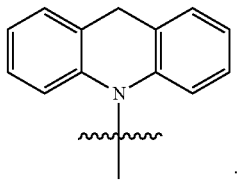 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen, such as aliphatic, heteroaliphatic, haloaliphatic, haloheteroaliphatic, aromatic, or an organic functional group.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, haloaliphatic, haloheteroaliphatic, aromatic, or an organic functional group.

Aroxy: —O-aromatic.

Azo: -N═NR$^a$ wherein R$^a$ is hydrogen, aliphatic, heteroaliphatic, haloaliphatic, haloheteroaliphatic, aromatic, or an organic functional group.

Carbamate: —OC(O)NR$^a$R$^b$, wherein each of R$^a$ and R$^b$ independently is selected from hydrogen, aliphatic, heteroaliphatic, haloaliphatic, haloheteroaliphatic, aromatic, or an organic functional group.

Carboxyl: —C(O)OH.

Carboxylate: —C(O)O$^-$ or salts thereof, wherein the negative charge of the carboxylate group may be balanced with an M$^+$ counterion, wherein M$^+$ may be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Cyano: —CN.

Disulfide: —SSR$^a$, wherein R$^a$ is selected from hydrogen, aliphatic, heteroaliphatic, haloaliphatic, haloheteroaliphatic, aromatic, or an organic functional group.

Dithiocarboxylic: —C(S)SR$^a$ wherein R$^a$ is selected from hydrogen, aliphatic, heteroaliphatic, haloaliphatic, haloheteroaliphatic, aromatic, or an organic functional group.

Electron-Accepting Group (EAG): A functional group capable of accepting electron density from the ring to which it is directly attached, such as by inductive electron withdrawal.

Electron-Donating Group (EDG): A functional group capable of donating at least a portion of its electron density into the ring to which it is directly attached, such as by resonance.

Ester: —C(O)OR$^a$ or —OC(O)R$^a$, wherein R$^a$ is selected from aliphatic, heteroaliphatic, haloaliphatic, haloheteroaliphatic, aromatic, or an organic functional group.

Ether: -aliphatic-O-aliphatic, -aliphatic-O-aromatic, -aromatic-O-aliphatic, or -aromatic-O-aromatic.

Halo (or halide or halogen): Fluoro, chloro, bromo, or iodo.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino, disulfide, peroxy, and thioether groups are exemplary (but non-limiting) examples of heteroaliphatic.

Heteroaliphatic-aryl: An aryl group that is or can be coupled to a compound disclosed herein, wherein the aryl group is or becomes coupled through a heteroaliphatic group.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, haloaliphatic, haloheteroaliphatic, aromatic, or an organic functional group.

Heteroatom: An atom other than carbon or hydrogen, such as (but not limited to) oxygen, nitrogen, sulfur, silicon, boron, selenium, or phosphorous. In particular disclosed embodiments, such as when valency constraints do not permit, a heteroatom does not include a halogen atom.

Ketone: —C(O)R$^a$, wherein R$^a$ is selected from aliphatic, heteroaliphatic, haloaliphatic, haloheteroaliphatic, aromatic, or an organic functional group.

Nanohoop: A compound comprising linked rings, such as linked aromatic rings (or groups), that are organized to form a hoop-like structure. In some embodiments, the rings can be linked in a para-, ortho-, or meta-substituted manner, or other positional manner. In some embodiments, the rings of the nanohoop skeleton are all linked in a para-substituted manner such that the bonds connecting each ring to two other rings of the nanohoop compound are para-substituted relative to each other. In some additional embodiments, at least one ring of the nanohoop skeleton is linked in a meta-substituted manner such that the bonds connecting this ring to two other rings of the nanohoop compound are meta-substituted relative to each other.

Organic Functional Group: A functional group that may be provided by any combination of aliphatic, heteroaliphatic, aromatic, haloaliphatic, and/or haloheteroaliphatic groups, or that may be selected from, but not limited to, aldehyde; aroxy; acyl halide; halogen; nitro; cyano; azide; carboxyl (or carboxylate); amide; ketone; carbonate; imine; azo; carbamate; hydroxyl; thiol; sulfonyl (or sulfonate); oxime; ester; thiocyanate; thioketone; thiocarboxylic acid; thioester; dithiocarboxylic acid or ester; phosphonate; phosphate; silyl ether; sulfinyl; thial; or combinations thereof.

Oxime: —CR$^a$=NOH, wherein R$^a$ is hydrogen, aliphatic, heteroaliphatic, haloaliphatic, haloheteroaliphatic, aromatic, or an organic functional group.

Peroxy: —O—OR$^a$ wherein R$^a$ is hydrogen, aliphatic, heteroaliphatic, haloaliphatic, haloheteroaliphatic, aromatic, or an organic functional group.

Phosphate: —O—P(O)(OR$^a$)$_2$, wherein each R$^a$ independently is hydrogen, aliphatic, heteroaliphatic, haloaliphatic, haloheteroaliphatic, aromatic, or an organic functional group; or wherein one or more R$^a$ groups are not present and the phosphate group therefore has at least one negative charge, which can be balanced by a counterion, M$^+$, wherein each M$^+$ independently can be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Phosphonate: —P(O)(OR$^a$)$_2$, wherein each R$^a$ independently is hydrogen, aliphatic, heteroaliphatic, haloaliphatic, haloheteroaliphatic, aromatic, or an organic functional group; or wherein one or more R$^a$ groups are not present and the phosphate group therefore has at least one negative charge, which can be balanced by a counterion, M$^{30}$, wherein each M$^+$ independently can be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as $[Ca^{2+}]_{0.5}$, $[Mg^{2+}]_{0.5}$, or $[Ba^{2+}]_{0.5}$.

Quaternary Amine: —N$^+$R$^b$R$^c$R$^d$, wherein each of R$^b$, R$^c$, and R$^d$ independently are selected from hydrogen, aliphatic, heteroaliphatic, aryl, heteroaryl, and any combination thereof.

Silyl Ether: —OSi R$^a$R$^b$, wherein each of R$^a$ and R$^b$ independently is selected from hydrogen, aliphatic, heteroaliphatic, haloaliphatic, haloheteroaliphatic, aromatic, or an organic functional group.

Sulfinyl: —S(O)R$^a$, wherein R$^a$ is selected from hydrogen, aliphatic, heteroaliphatic, haloaliphatic, haloheteroaliphatic, aromatic, or an organic functional group.

Sulfonyl: —SO$_2$R$^a$, wherein R$^a$ is selected from hydrogen, aliphatic, heteroaliphatic, haloaliphatic, haloheteroaliphatic, aromatic, or an organic functional group.

Sulfonamide: —SO$_2$NR$^a$R$^b$ or —N(R$^a$)SO$_2$R$^b$, wherein each of R$^a$ and R$^b$ independently is selected from hydrogen, aliphatic, heteroaliphatic, haloaliphatic, haloheteroaliphatic, aromatic, or an organic functional group.

Sulfonate: —SO$_3^-$, wherein the negative charge of the sulfonate group may be balanced with an M$^+$ counter ion, wherein M$^+$ may be an alkali ion, such as K$^+$, Na$^{30}$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as [Ca$^{2+}$]$_{0.5}$, [Mg$^{2+}$]$_{0.5}$, or [Ba$^{2+}$]$_{0.5}$.

Thial: —C(S)H.

Thiocarboxylic acid: —C(O)SH, or —C(S)OH.

Thiocyanate: —S—CN or —N=C=S.

Thioester: —C(O)SR$^a$ or —C(S)OR$^a$ wherein R$^a$ is selected from hydrogen, aliphatic, heteroaliphatic, haloaliphatic, haloheteroaliphatic, aromatic, or an organic functional group.

Thioether: —S-aliphatic or —S-aromatic, such as —S-alkyl, —S-alkenyl, —S-alkynyl, —S-aryl, or —S-heteroaryl; or -aliphatic-S-aliphatic, -aliphatic-S-aromatic, -aromatic-S-aliphatic, or -aromatic-S-aromatic.

Thioketone: —C(S)R$^a$ wherein R$^a$ is selected from hydrogen, aliphatic, heteroaliphatic, haloaliphatic, haloheteroaliphatic, aromatic, or an organic functional group.

II. INTRODUCTION

To date, one class of macrocycles that has never been incorporated into polymers is the nanohoop class of compounds (e.g., cycloparaphenylenes, or "CPPs" or "[n] CPPs"). For example, cycloparaphenylenes, which are comprised of n benzene rings linked end-to-end in the para position, are strained cyclic molecules can be thought of as the shortest fragments of armchair carbon nanotubes (CNTs). Unique photophysical properties arise from bending benzene into a hoop shape in this manner. For example, unlike in their linear counterparts, the HOMO-LUMO energy gap of CPPs decreases as the number of linked benzene rings decreases. This trend is also reflected in the red-shifting fluorescence emission as the hoop size decreases. For example, [12]CPP has an emission maximum at 450 nm while [7]CPP emits at 587 nm. In some embodiments, CPPs share an absorbance maximum near 340 nm. Distortion of the phenyl rings in CPPs can disrupt pi-pi interactions among macrocycles, allowing CPPs with, e.g., 12 or more unsubstituted phenyl rings, to be readily soluble in common organic solvents. CPPs also can comprise finely-tunable pore diameters and resultant supramolecular interactions. Disclosed herein polymer embodiments comprising one or more nanohoop compounds that extend as "side arms" from the polymer. The polymer embodiments disclosed herein have controlled molecular weights, moderate dispersities, and high degrees of polymerization. Also disclosed herein are polymerizable nanohoop monomer embodiments that can be used as templates for polymerization to provide polymer embodiments disclosed herein.

III. POLYMER EMBODIMENTS

Disclosed herein are embodiments of a polymer comprising a polymer backbone functionalized with one or more nanohoop compounds that are covalently attached to the polymer backbone, but do not make up the polymer backbone. In other words, the nanohoop compounds can extend from the polymer backbone as "side arms." In particular embodiments, the nanohoop is not linearly conjugated with the polymer backbone, but it still exhibits radial conjugation with ring systems that make up the nanohoop. In some embodiments, the polymer has a structure satisfying Formula I below.

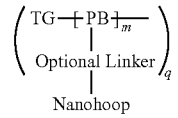

Formula I

With reference to Formula I, the PB group represents the polymer backbone of the polymer (e.g., a polymer backbone formed from polymerization methods disclosed herein and/or a polymer backbone formed from norbornenes, acrylates, methacrylates, methyacrylamides, stryenes, dienes, vinyl acetate, n-vinylpyrrolidone, aldehydes, epoxides, acrylonitriles, cyanoacrylates, alcohols, carboxylic acids, amines, ethers, or the like); "TG" represents a terminating group; the optional linker can be a linker selected from aliphatic, heteroaliphatic, haloaliphatic, haloheteroaliphatic, aromatic, or an organic functional group; the nanohoop can be a nanohoop comprising any suitable number of aromatic ring systems wherein each aromatic ring system is bound to at least two other ring systems of the nanohoop through two separate single covalent bonds that are positioned para, ortho, or meta relative to one another (e.g., 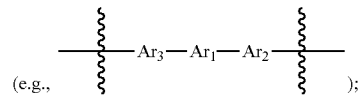 );

m is an integer ranging from two or greater such as 2 to 10,000 or greater, or 2 to 1000 or greater, or 2 to 100 or greater, or the like; and q is an integer selected from 1 or 2. In some embodiments, the nanohoop comprises 6 or more aromatic ring systems (e.g., 6 to 100 aromatic ring systems, or 6 to 50, or 6 to 25, or 6 to 15, or 6 to 10 aromatic ring systems). In some embodiments, the nanohoop compounds can be covalently attached to the polymer backbone through one point of attachment (such as through one carbon atom of a ring of the nanohoop compound), or through two points of attachments (such as through two adjacent carbon atoms of a five-membered ring attached to an aromatic ring system of the nanohoop compound). Also, the nanohoop can be covalently attached to two different polymer backbones (as represented by q being 2). In some embodiments, each of the PB and TG groups independently comprise aliphatic, heteroaliphatic, haloaliphatic, haloheteroaliphatic, aromatic, or organic functional groups.

In some embodiments, the polymer can have a structure satisfying Formula II.

Formula II

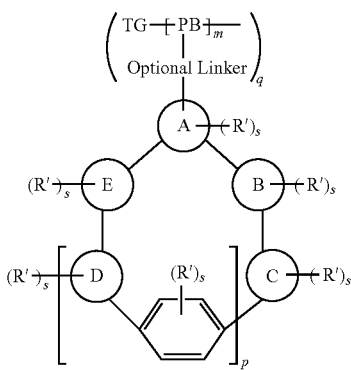

Formula IV

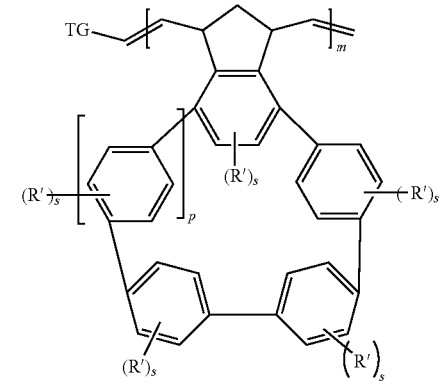

With reference to Formula II, each of rings A, B, C, D, and E independently are aromatic ring systems; each R' independently is a substituent other than hydrogen; each s independently is an integer selected from 0 to 10, such as 0 to 5, or 1 to 5, or 1 to 4, or 1 to 3; each p independently is an integer selected from 1 to 1000, such as 1 to 500, or 1 to 250, or 1 to 100, or 2 to 10; and each of TG, PB, optional linker, and m can be as recited above for Formula I. In some embodiments, rings A, B, C, D, and E can be bound to the other rings of the nanohoop by para, meta, or ortho linkages. In some embodiments, each of rings B, C, D, E, F, and G independently can be an aryl (e.g., phenyl) or heteroaryl group (e.g., pyridinyl). In particular embodiments, each of rings B, C, D, E, F, and G independently can be phenyl. In some embodiments, each R' independently can be aliphatic, heteroaliphatic, haloaliphatic, aromatic, or an organic functional group. In some embodiments, the PB group can comprise a five-membered ring fused to ring A that also comprises two carbon atoms that are functionalized with aliphatic groups. In some embodiments, TG is an aromatic ring (e.g., phenyl). In some embodiments, p is 1, 2, 3, 4, 5, 6, 7, 8, 9, or 10.

In some embodiments, the polymer can have a structure satisfying Formula III or IV, illustrated below.

Formula III

TG

Optional Linker

With reference to Formulas III and IV, TG, each R', m, each p, and each s independently can be as recited for any one or more of the formulas described above. In some embodiments, TG is phenyl; the optional linker, if present, is aliphatic, heteroaliphatic, or aromatic; each R' independently is aliphatic, aryl, heteroaryl, halogen, an electron-accepting group, an electron-donating group, or any combination thereof; each s independently is 0 or 1; and p is 4 or 6.

Representative polymer embodiments are illustrated below.

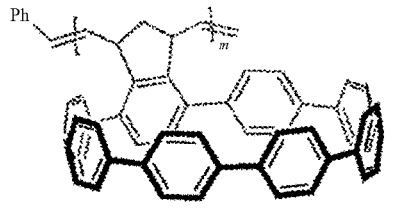

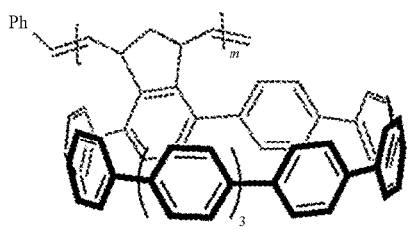

Also disclosed herein are polymerizable nanohoop monomers that can be used to make the polymer embodiments described above. In some embodiments, the polymerizable nanohoop monomers have a structure satisfying Formula V.

Formula V $$\left( \begin{array}{c} PFG \\ | \\ \text{Optional Linker} \end{array} \right)_q$$
$$|$$
$$\text{Nanohoop}$$

With reference to Formula V, the PFG group represents a polymerizable functional group (e.g., norbornenes, acrylates, methacrylates, methyacrylamides, stryenes, dienes, vinyl acetate, n-vinylpyrrolidone, aldehydes, epoxides, acrylonitriles, cyanoacrylates, alcohols, carboxylic acids, amines, ethers, or the like); the optional linker can be a linker selected from aliphatic, heteroaliphatic, haloaliphatic, haloheteroaliphatic, aromatic, or an organic functional group; the nanohoop can be a nanohoop comprising any suitable number of aromatic ring systems wherein each aromatic ring system is bound to at least two other ring systems of the nanohoop through two separate single covalent bonds that are positioned para, ortho, or meta relative to one another

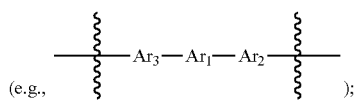

(e.g.,          );

and q is an integer selected from 1 or 2. In some embodiments, the nanohoop comprises 6 or more aromatic ring systems (e.g., 6 to 100, or 6 to 50, or 6 to 25, or 6 to 15, or 6 to 10, aromatic ring systems). In some embodiments, the nanohoop compounds can be covalently attached to the PFG through one point of attachment (such as through one carbon atom of a ring of the nanohoop compound), or through two points of attachments (such as through two adjacent carbon atoms of a five-membered ring attached to an aromatic ring system of the nanohoop compound). Also, the nanohoop can be covalently attached to two different PFGs (as represented by q being 2).

In some embodiments, the polymerizable nanohoop monomer can have a structure satisfying Formula VI.

Formula VI

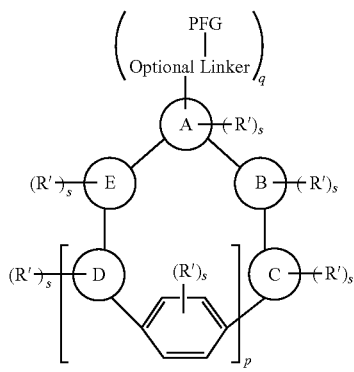

With reference to Formula VI, each of rings A, B, C, D, and E independently are aromatic ring systems; each R' independently is a substituent other than hydrogen; each s independently is an integer selected from 0 to 10, such as 0 to 5, or 1 to 5, or 1 to 4, or 1 to 3; p is an integer selected from 1 to 1000 (e.g., 1 to 500, or 1 to 250, or 1 to 100, or 1 to 10, or 1, 2, 3, 4, 5, 6, 7, 8, 9, or 10); and the PFG, the optional linker, and q can be as recited above for Formula V. In some embodiments, rings A, B, C, D, and E can be bound to the other rings of the nanohoop by para, meta, or ortho linkages. In some embodiments, each of rings B, C, D, E, F, and G independently can be an aryl (e.g., phenyl) or heteroaryl group (e.g., pyridinyl). In particular embodiments, each of rings B, C, D, E, F, and G independently can be phenyl. In some embodiments, each R' independently can be aliphatic, heteroaliphatic, haloaliphatic, aromatic, or an organic functional group. In some embodiments, the PFG can comprise a bicyclic structure comprising at least one double bond and may be bound directly to ring A through a single bond or by being fused to ring A, or may be bound indirectly to ring A through the optional linker group. In some embodiments, the PFG is a norbornene ring system and is fused to ring A. In some embodiments, q is 1 and p is 2 or 3.

In some embodiments, the polymer can have a structure satisfying Formula VII or VIII, illustrated below.

Formula VII

Formula VIII

With reference to Formulas VII and VIII, each R', each s, and p independently can be as recited for any one or more of the formulas described above. In some embodiments, the optional linker, if present, is aliphatic or aromatic; each R' independently is aliphatic, aryl, heteroaryl, halogen, an electron-accepting group, an electron-donating group, or any combination thereof; each s independently is 0 or 1; and p is 4 or 6.

Representative polymerizable nanohoop monomer embodiments are illustrated below.

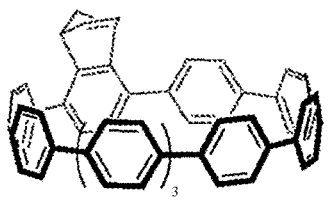

3

IV. METHOD EMBODIMENTS

Also disclosed herein are embodiments of a method for making the nanohoop-functionalized polymer embodiments. In some embodiments, the method comprises polymerizing one or more polymerizable nanohoop monomers to provide a polymer backbone from which the nanohoops extend. In particular embodiments, a polymerizable nanohoop monomer comprises one or more polymerizable functional groups. In some such embodiments, the one or more polymerizable functional groups can be bound to the same individual aromatic ring of the nanohoop, or they can be bound to different aromatic rings of the nanohoop. In particular embodiments, at least one polymerizable functional group is attached to at least one aromatic ring of the nanohoop. In yet some other particular embodiments, two or more polymerizable functional groups are attached to at least one aromatic ring of the nanohoop.

In some embodiments, polymerization can comprise polymerizing the same polymerizable nanohoop monomer to provide a homopolymer comprising a polymer backbone attached to a plurality of nanohoops that extend from the polymer backbone. In yet some additional embodiments, polymerization can comprise polymerizing different polymerizable nanohoop monomer embodiments to provide a heteropolymer comprising a polymer backbone attached to a plurality of different nanohoops wherein at least two nanohoops are different from one another. In yet some additional embodiments, heteropolymer embodiments can comprise a polymer backbone that is made from different polymerizable nanohoop monomers that differ in the identity of their polymermizable functional groups. Polymerization typically takes place by forming bonds between the polymerizable functional groups of the polymerizable nanohoop monomers.

In some embodiments, the method comprises using a polymerization method selected from a ring opening metathesis polymerization method (or ROMP), a reversible addition-fragmentation chain transfer (or RAFT) method, an anionic polymerization method, or a condensation polymerization method. Other suitable polymerization methods also can be used as long as they do not disrupt the structural integrity of the nanohoops.

In some embodiments, the method is a ROMP method and comprises exposing one or more polymerizable nanohoop monomers to a catalyst capable of promoting covalent bond formation between the polymerizable functional groups of the polymerizable nanohoop monomers to thereby provide a polymer backbone, as illustrated in Scheme 1. In some embodiments, the catalyst also can serve as a source for a terminating group that becomes bound to one end of the polymer during polymerization. In some embodiments, chemical bonds (e.g., carbon-carbon double bonds) of a polymerizable functional group can be broken and can then bind with other reactive polymerizable functional groups of other polymerizable nanohoop monomers to thereby form the polymer backbone. In some embodiments, at least one of the polymerizable functional groups can be covalently attached to a terminating group, which can be provided by the catalyst used for polymerization, or by a terminating reagent. A representative ROMP method is illustrated below in Scheme 1.

Scheme 1

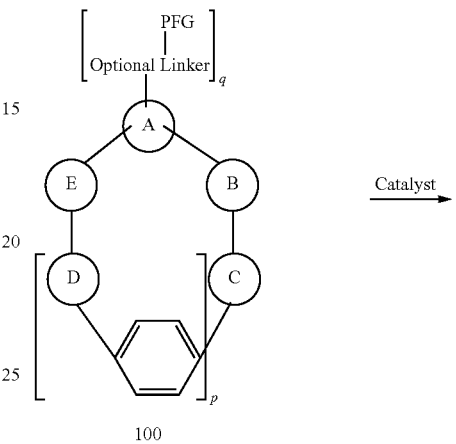

100

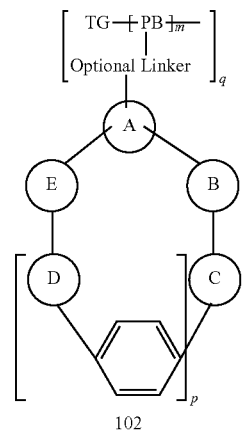

102

With reference to compounds 100 and 102 shown in Scheme 1, each of rings A-E are aromatic groups as defined herein for Formulas II or VI; PFG is a polymerizable functional group; the optional linker is linker group selected from an aliphatic group, a heteroaliphatic group, an aromatic group, an organic functional group, or any combination thereof; p is 1 to 1000 (such as 1 to 500, or 1 to 250, or 1 to 100); TG represents a terminating group; PB represents the polymer backbone provided as polymerization takes place; and m is an integer ranging from 2 or greater (e.g., 2 to 10,000 or greater, or 2 to 1000 or greater, or 2 to 100 or greater, or the like). In some embodiments, the catalyst can be a catalyst capable of promoting ROMP, such as an alkylidene catalyst (e.g., a ruthenium alkylidene catalyst like bromopyridyl Grubbs G3, or other Grubbs catalysts).

In a representative ROMP method, a norbornene group can be used as a polymerizable functional group. When the norbornene group is exposed to an alkylidene catalyst (e.g., a ruthenium-based Grubbs catalyst, such as bromopyridyl Grubbs G3 catalyst 202 shown in Scheme 2), the double bond of the norbornene ring system is broken and the carbon atoms of the double bond each form a new double bond to thereby providing alkene linking groups that make-up the polymer backbone (e.g., see compound 204 in Scheme 2). In some embodiments, at least one of the carbon atoms of the norbornene group becomes covalently attached to a terminating group provided by the catalyst. Representative ROMP methods are shown in Scheme 2.

dithiocarbonate having a structure satisfying a formula $R^aOC(=S)SR^b$ or $R^aSC(=S)OR^b$ (wherein each of $R^a$ and $R^b$ independently can be selected from hydrogen, aliphatic, heteroaliphatic, aromatic, or combinations thereof); a xanthate having a structure satisfying a formula $R^aOC(=S)SM^+$ (wherein $R^a$ is aliphatic, aromatic, or a combination thereof and M is a counterion having a +1 charge, such as

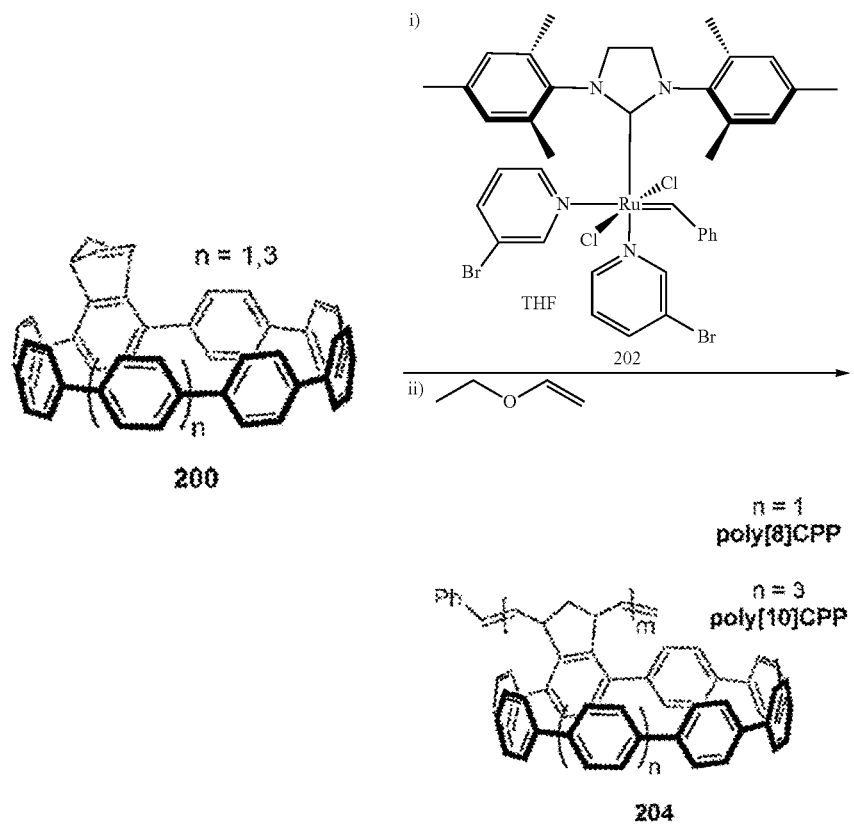

In other embodiments, the method can be a RAFT polymerization method. In such embodiments, polymerizable functional groups of the polymerizable nanohoop monomer(s) can be bound together to form a polymer backbone by reacting the polymerizable nanohoop monomers with a radical source and a RAFT agent. The radical source can be an initiator compound, such as azobisisobutyronitrile (AIBN) or 4,4'-azobis(4-cyanovaleric acid) (ACVA). The RAFT agent can be a dithioester having a structure satisfying a formula $R^aC(=S)SR^b$ (wherein each of $R^a$ and $R^b$ independently can be selected from aliphatic, aromatic, or combinations thereof); a thiocarbamate having a structure satisfying a formula $R^aOC(=S)NR^bR^c$ or $R^aSC(=O)NRbRc$ (wherein each of $R^a$, $R^b$, and $R^c$ independently can be selected from hydrogen, aliphatic, heteroaliphatic, aromatic, or combinations thereof); a dithiocarbamate having a structure satisfying a formula $R^aSC(=S)NR^bR^c$ (wherein each of $R^a$, $R^b$, and $R^c$ independently can be selected from hydrogen, aliphatic, heteroaliphatic, aromatic, or combinations thereof); a trithiocarbonate having a structure satisfying a formula $R^aSC(=S)SR^b$ (wherein each of $R^a$ and $R^b$ independently can be selected from hydrogen, aliphatic, heteroaliphatic, aromatic, or combinations thereof); a sodium, potassium, ammonium, or the like); or a xanthate ester having a structure satisfying a formula $R^aOC(=S)SR^b$ (wherein each of $R^a$ and $R^b$ independently can be selected from aliphatic, aromatic, or combinations thereof). Polymerizable functional groups that can be used in such embodiments can include, but are not limited to, acrylates, methacrylates (e.g., methyacrylate), methacrylamides, stryenes, dienes (e.g., butadiene and derivatives thereof), vinyl acetate, n-vinylpyrrolidone, aldehydes, epoxides, acrylonitriles, and cyanoacrylates. Such polymerizable functional groups can be directly attached to a nanohoop, or they can be indirectly attached through an optional linker.

In yet additional embodiments, the method can be an anionic polymerization method. In such embodiments, polymerizable functional groups of the polymerizable nanohoop monomer(s) can be bound together to form a polymer backbone by reacting the polymerizable nanohoop monomers with an initiator compound, such as an alkali metal or a covalent or ionic metal compound (e.g., covalent or ionic metal amide, alkoxide, hydroxide, amine, phosphine, or cyanide), or an organometallic compound (e.g., an alkyl lithium or Grignard reagent). Polymerizable functional groups that can be used in such embodiments can include, but are not limited to, acrylates, methacrylates (e.g., methyacrylate), methyacrylamides, stryenes, dienes (e.g., butadiene and derivatives thereof), vinyl acetate, n-vinylpyrrolidone, aldehydes, epoxides, acrylonitriles, and cyanoacrylates. Such polymerizable functional groups can be directly attached to a nanohoop, or they can be indirectly attached through an optional linker.

In yet additional embodiments, the method can be a condensation polymerization method. In such embodiments, polymerizable functional groups of the polymerizable nanohoop monomer(s) can be bound together to form a polymer backbone by condensing the polymerizable nanohoop monomers together under reaction conditions that promote condensation. Polymerizable functional groups that can be used in such embodiments can include, but are not limited to, alcohols, carboxylic acids, amines, ethers, and the like. Such polymerizable functional groups can be directly attached to a nanohoop, or they can be indirectly attached through an optional linker.

In some embodiments, the method can further comprise making the polymerizable nanohoop monomer. In some embodiments, the method can further comprise making a polymerizable nanohoop monomer that comprises one or more "pre-installed" functional groups capable of undergoing polymerization to provide a polymer backbone to which the nanohoop is attached. In such embodiments, the functional groups are "pre-installed" because they are installed as the nanohoop is made. In yet some additional embodiments, the method can comprise modifying a nanohoop compound with one or more functional groups capable of polymerizing to provide the polymer backbone. In such embodiments, the nanohoop compound is made first and then is functionalized to comprise the polymerizable functional group.

In some embodiments, the method comprises making a nanohoop monomer comprising a pre-installed polymerizable group. Such a method is described in Scheme 3.

Scheme 3

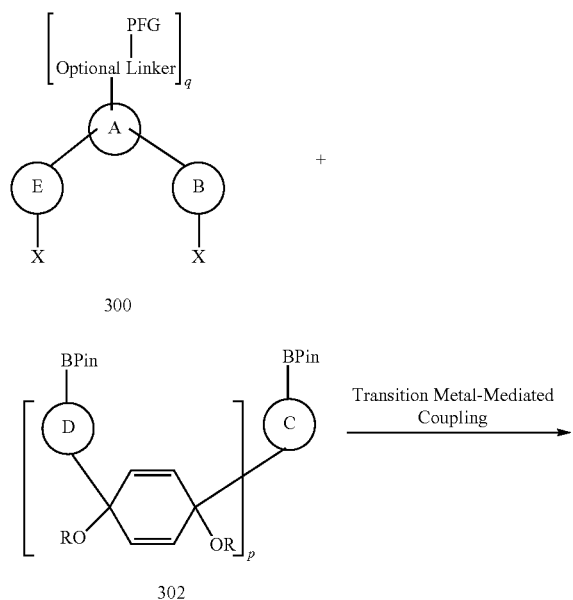

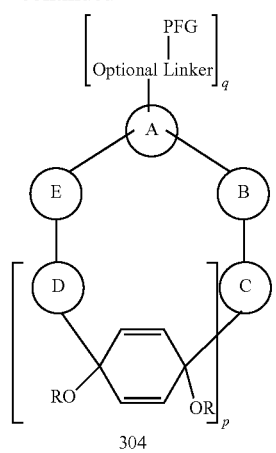

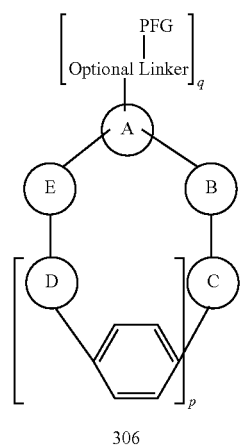

With reference to Scheme 3, two coupling partners (e.g., coupling partners 300 and 302) can be coupled to one another using a transition metal-mediated cross-coupling reaction to provide polymerizable nanohoop monomer precursor 304. In Scheme 1, coupling partner 300 comprises the polymerizable functional group; however, the present disclosure contemplates method embodiments wherein the polymerizable functional group is attached to coupling partner 302. Rings A-E of coupling partners 300 and 302 can be selected from any suitable aromatic group so as to provide nanohoops described herein. With reference to coupling partner 302, each R independently can be a protecting group selected from aliphatic protecting groups (e.g., lower alkyl, such as methyl) or silyl protecting groups (e.g., TES, TMS, TBS, TBDPS, TIPS, and the like). Aromatization of polymerizable nanohoop monomer precursor 304 to polymerizable nanohoop monomer 306 can take place by using a reductive aromatization method. Exemplary reagents and method embodiments for making polymerizable nanohoop monomers comprising pre-installed polymerizable functional groups are detailed in Schemes 4 and 5, below.

Scheme 4

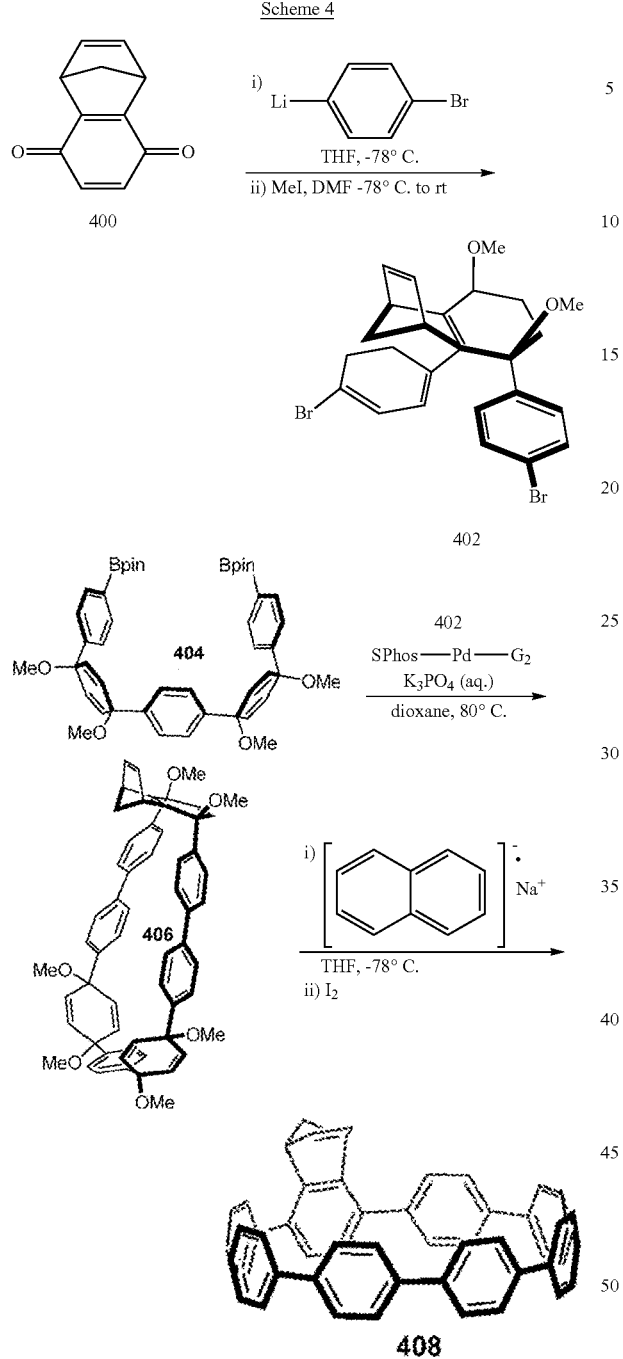

With reference to Scheme 4, a ROMP-reactive benzonorbornene unit was "pre-installed" into a CPP backbone. In particular, double nucleophilic addition of (4-bromophenyl) lithium to norbornene-benzoquinone 400 followed by in situ methylation of the resulting alkoxides yields dibromide 402. This curved intermediate can serve as a common coupling partner for different-sized nanohoop monomer embodiments (e.g., nanohoop monomer embodiments comprising n number of rings in the nanohoop). Coupling partner 404 is prepared by means of iterative diastereoselective nucleophilic additions (described in the Examples section herein). Macrocycle 406 comprises 8 total phenylene and cyclohexadiene units and is obtained via dilute Suzuki-Miyaura cross-coupling of dibromide 402 with bisboronate 404. Reductive aromatization of 406 with sodium naphthalenide yields polymerizable nanohoop monomer 408.

Another exemplary method embodiment is detailed in Scheme 5.

Scheme 5

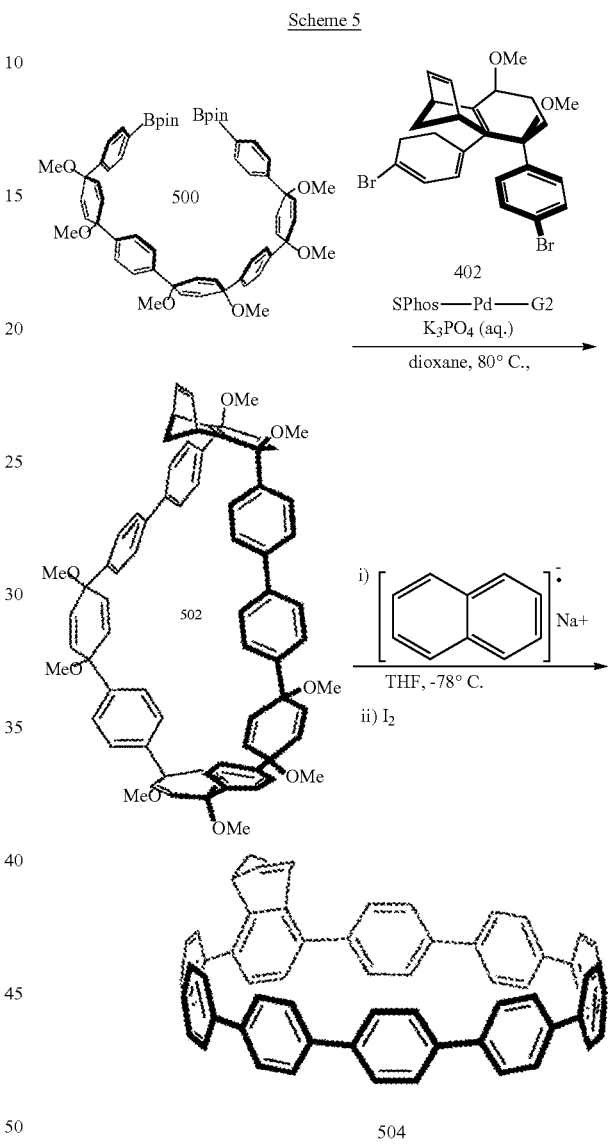

With reference to Scheme 5, Suzuki-Miyaura cross-coupling of bisboronate 500 and dibromide 402 yields macrocycle 502 comprising 10 (masked) phenylene units. Reductive aromatization of 502 yields polymerizable nanohoop monomer 504.

In some embodiments, the polymer embodiments disclosed herein can be used electronic devices, optoelectric devices, and other types of devices employing conjugated polymers. In some embodiments, polymer embodiments can be used as a graphene surrogate and thus can be used in applications that typically employ graphene and/or graphene derivatives. In yet additional embodiments, polymer embodiments can be used as a component for sensor devices (e.g., devices that employ supramolecular sensing).

V. OVERVIEW OF SEVERAL EMBODIMENTS

Disclosed herein are embodiments of a polymer having a structure according to Formula I

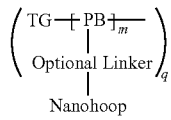

Formula I wherein PB is a polymer backbone; TG is a terminating group; the optional linker is selected from aliphatic, heteroaliphatic, haloaliphatic, haloheteroaliphatic, aromatic, or an organic functional group; the nanohoop comprises six or more aromatic ring systems and wherein each aromatic ring is bound to at least two other rings of the nanohoop by two separate single covalent bonds positioned para, ortho, or meta relative to one another; m is an integer ranging from two or greater; and q is an integer selected from 1 or 2.

In some embodiments, TG is an aromatic ring. In some such embodiments, the aromatic ring is a phenyl ring.

In any or all of the above embodiments, the optional linker is not present and PB is covalently attached to the nanohoop through two points of attachment.

In any or all of the above embodiments, PB is a five-membered ring and two adjacent carbon atoms of the five-membered ring are attached to two adjacent carbon atoms of the nanohoop.

In any or all of the above embodiments, the optional linker is not present and PB is covalently attached to the nanohoop through one point of attachment.

In any or all of the above embodiments, q is 2 and each PB is different from the other. In any or all of the above embodiments, the polymer has a structure according to Formula II

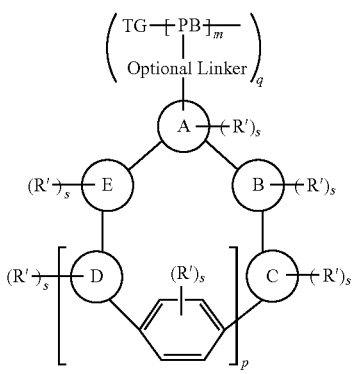

Formula II wherein each of rings A, B, C, D, and E independently are aromatic ring systems; each R' independently is a substituent other than hydrogen; each s independently is an integer selected from 0 to 10; and p is an integer selected from 1 to 1000.

In any or all of the above embodiments, each of rings A, B, C, D, and E independently are aryl or heteroaryl.

In any or all of the above embodiments, each of rings A, B, C, D, and E independently are phenyl or pyridinyl.

In any or all of the above embodiments, each R' independently is selected from aliphatic, heteroaliphatic, haloaliphatic, aromatic, or an organic functional group.

In any or all of the above embodiments, the polymer has a structure according to Formula III or IV

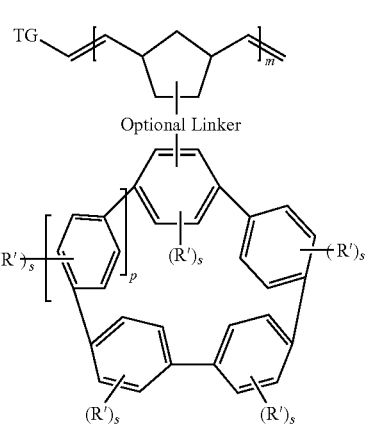

Formula III

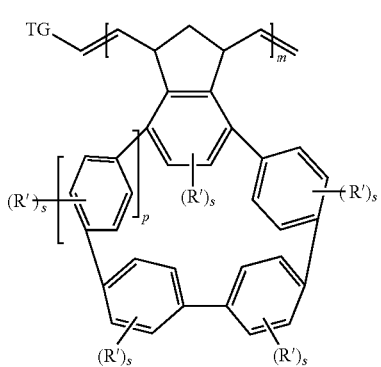

Formula IV wherein each R' independently is a substituent other than hydrogen; each s independently is an integer selected from 0 to 10; and p is an integer selected from 1 to 1000.

In any or all of the above embodiments, each R' independently is selected from aliphatic, aryl, heteroaryl, halogen, an electron-accepting group, an electron-donating group, or any combination thereof.

In any or all of the above embodiments, the polymer is

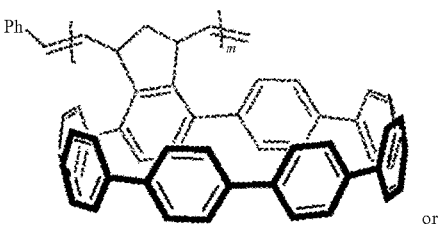

or

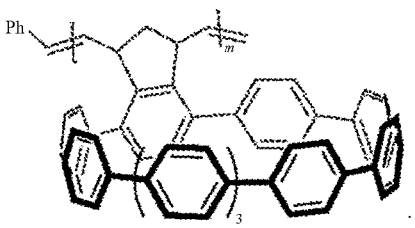

Also disclosed are embodiments of a compound, having a structure according to Formula V

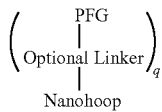

Formula V wherein:

PFG is a polymerizable functional group comprising a bicyclic structure comprising at least one double bond;

the optional linker is selected from aliphatic, heteroaliphatic, haloaliphatic, haloheteroaliphatic, aromatic, or an organic functional group;

the nanohoop comprises six or more aromatic ring systems and wherein each aromatic ring is bound to at least two other rings of the nanohoop by two separate single covalent bonds positioned para, ortho, or meta relative to one another; and $q$ is 1 or 2.

In some embodiments, the compound has a structure according to Formula VII or VIII

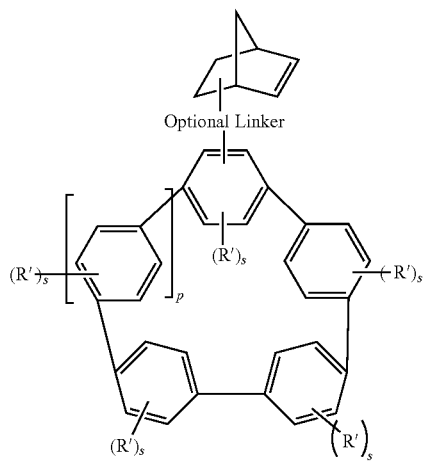

Formula VII

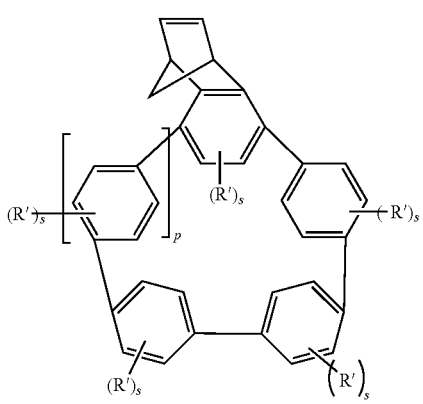

Formula VIII wherein each R' independently is a substituent other than hydrogen; each s independently is an integer selected from 0 to 10; and p is an integer selected from 1 to 1000.

In any or all of the above embodiments, the compound is

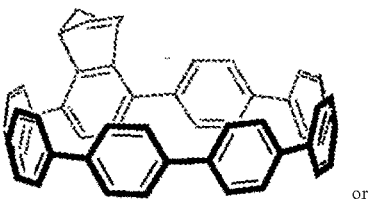

or

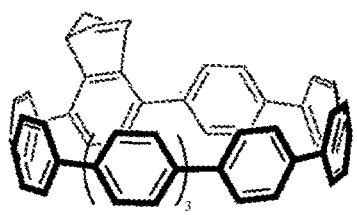

Also disclosed herein are embodiments of a method, comprising exposing one or more polymerizable nanohoop monomers to conditions that promote ring opening metathesis polymerization, reversible addition-fragmentation chain transfer, anionic polymerization, or condensation polymerization between the one or more polymerizable nanohoop monomers to thereby provide a nanohoop-functionalized polymer wherein bonds are formed between polymerizable functional groups of the one or more polymerizable nanohoop monomers; wherein the one or more polymerizable nanohoop monomers independently have a structure according to Formula V

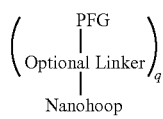

Formula V wherein each PFG independently is selected from a norbornene, an acrylate, a methacrylate, a methyacrylamide, a stryene, a diene, vinyl acetate, n-vinylpyrrolidone, an aldehyde, an epoxide, an acrylonitrile, a cyanoacrylate, an alcohol, a carboxylic acid, an amine, or an ether;

the optional linker is selected from aliphatic, heteroaliphatic, haloaliphatic, haloheteroaliphatic, aromatic, or an organic functional group;

the nanohoop comprises six or more aromatic ring systems and wherein each aromatic ring is bound to at least two other rings of the nanohoop by two separate single covalent bonds positioned para, ortho, or meta relative to one another; and $q$ is 1 or 2.

In some embodiments, the method comprising exposing the one or more polymerizable nanohoop monomers to a ruthenium-based catalyst to promote a ring opening metathesis polymerization between the polymerizable functional groups of the one or more polymerizable nanohoop monomers and wherein the polymerizable nanohoop monomer has a structure according to Formula VII or VIII

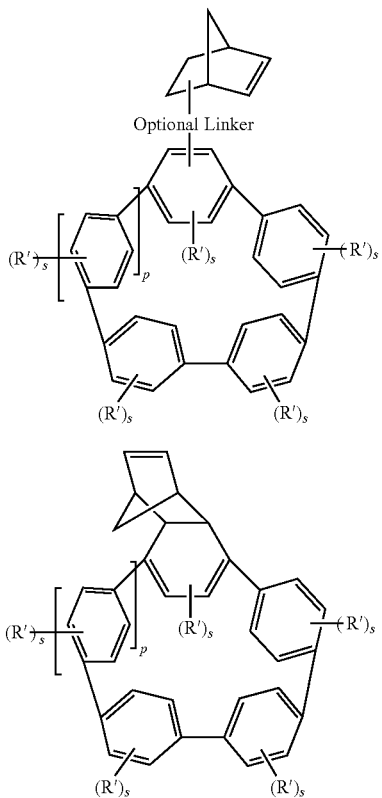

Formula VII

Formula VIII wherein each R' independently is a substituent other than hydrogen; each s independently is an integer selected from 0 to 10; and p is an integer selected from 1 to 1000.

Also disclosed herein are embodiments of a method, comprising: coupling together two coupling partners using a transition metal-mediated cross-coupling reaction to provide a polymerizable nanohoop monomer precursor; and performing a reductive aromatization step with the polymerizable nanohoop monomer precursor to provide a polymerizable nanohoop monomer having a Formula V

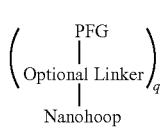

Formula V wherein
each PFG independently is selected from a norbornene, an acrylate, a methacrylate, a methyacrylamide, a stryene, a diene, vinyl acetate, n-vinylpyrrolidone, an aldehyde, an epoxide, an acrylonitrile, a cyanoacrylate, an alcohol, a carboxylic acid, an amine, or an ether;
the optional linker is selected from aliphatic, heteroaliphatic, haloaliphatic, haloheteroaliphatic, aromatic, or an organic functional group;
the nanohoop comprises six or more aromatic ring systems and wherein each aromatic ring is bound to at least two other rings of the nanohoop by two separate single covalent bonds positioned para, ortho, or meta relative to one another; and
q is 1 or 2.

VI. EXAMPLES

Commercially available materials were used without purification. Moisture- and oxygen-sensitive reactions were carried out in flame-dried glassware and under an inert atmosphere of purified nitrogen using syringe/septa technique. Tetrahydrofuran (THF), 1,4-dioxane, and dimethylformamide (DMF) were dried by filtration through alumina according to the methods described by Grubbs. Thin Layer Chromatography (TLC) was performed using Sorbent Technologies Silica Gel XHT TLC plates. Developed plates were visualized using UV light at wavelengths of 254 and 365 nm. Silica column chromatography was conducted with Zeochem Zeoprep 60 Eco 40-63 μm silica gel. Automated flash chromatography was performed using a Biotage Isolera One. Recycling gel permeation chromatography (GPC) was performed using a Japan Analytical Industry LC-9101 preparative HPLC with JAIGEL-1 H/JAIGEL-2H columns in series using $CHCl_3$. $^1H$ and $^{13}C$ NMR spectra were recorded on a Bruker Avance III HD 500 MHz ($^1H$: 500 MHz, $^{13}C$: 126 MHz) NMR spectrometer. All spectra were taken in $CDCl_3$, and the chemical shifts (δ) were reported in parts per million (ppm) referenced to TMS (δ0.00 ppm) for $^1H$ NMR and residual $CHCl_3$ (δ77.16 ppm) for $^{13}C$ NMR. GPC for polymer molecular weight determination was performed on a TOSOH EcoSEC HLC-8320GPC in THF against polystyrene standards using refractive index measurements. Dynamic light scattering (DLS) was performed in THF using the default globular protein model on a Wyatt Technology Mobius. UV-vis absorption and fluorescence spectra were recorded in a 1 cm quartz cuvette on an Agilent Cary 100 spectrophotometer and a Horiba Jobin Yvon Fluoromax-4 Fluorometer, respectively. Fluorescence quantum yields were measured in THF using a Hamamatsu absolute photoluminescence quantum yield measurement system. All absorption and fluorescence measurements were carried out under ambient conditions. Mass spectrometry measurements were carried out by the staff at the School of Chemical Sciences Mass Spectrometry Laboratory at UIUC. For MALDI measurements, trans-2-[3-(4-tert-butylphenyl)-2-methyl-2-propenylidene]malononitrile (DCTB) was used as the matrix.

Example 1

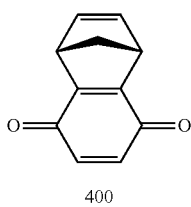

400

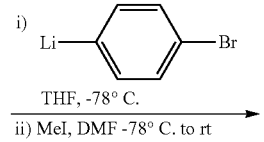

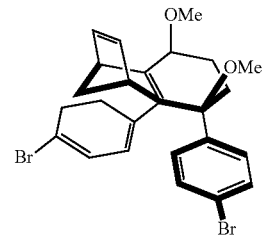

402

Figure 17A:
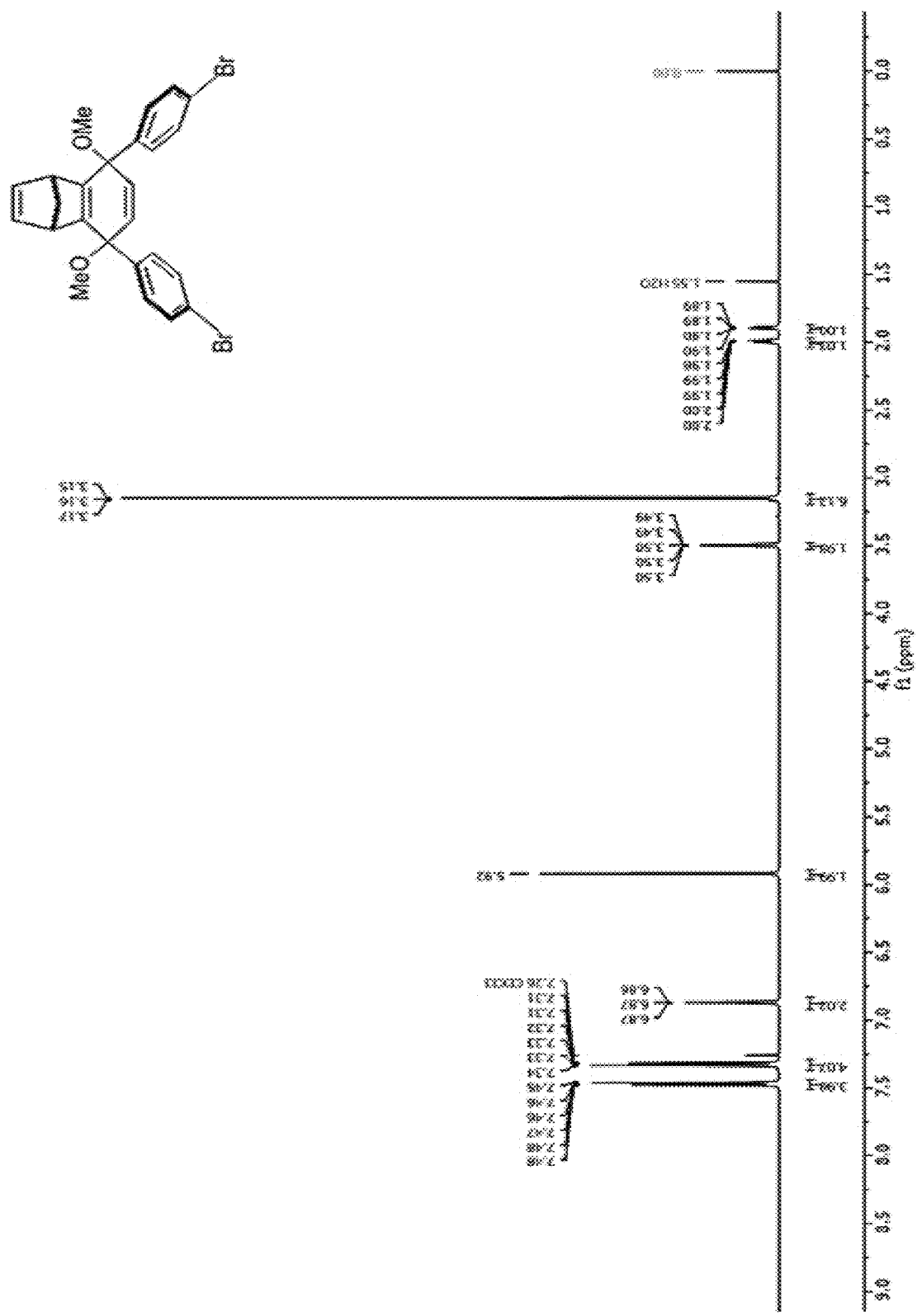
FIGS. 17A-17D are proton NMR spectra (FIGS. 17A and 17C) and carbon NMR spectra (FIGS. 17B and 17D) of intermediates 402 (FIGS. 17A and 17B) and 406 (FIGS. 17C and 17D).
Figure 17B:
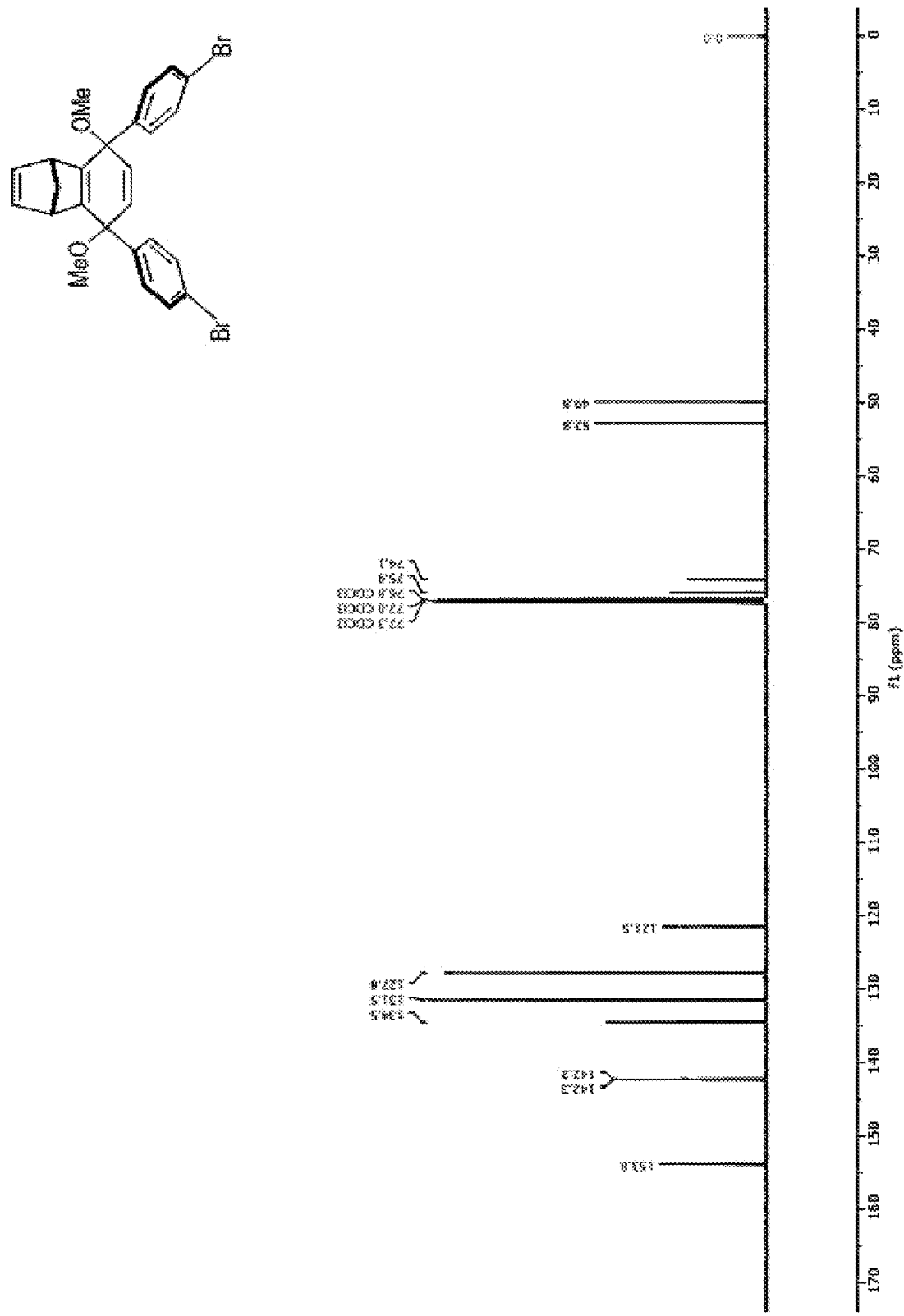

A flame-dried flask was charged with 1,4-dibromobenzene (8.2 g, 34.8 mmol, 3.00 equiv.), which was dissolved in THF (80 mL) and then cooled to −78° C. for 20 minutes. n-BuLi (15.8 mL, 24.8 mmol, 3.00 equiv.) was added dropwise. The reaction was stirred at −78° C. for 20 minutes, after which a solution of norbornene-benzoquinone 400 (2.00 g, 11.6 mmol, 1.00 equiv.) in THF (8 mL) was added dropwise. The reaction was stirred for 1 hour at −78° C. Methyl iodide (7.2 mL, 116.2 mmol, 10.00 equiv.) and a few mL of DMF were added to the reaction, which was stirred overnight at room temperature then quenched with water. The THF was removed under reduced pressure, and the resulting solution was extracted with ethyl acetate (3×). The combined organic layers were washed with 5% aqueous LiCl (3×), water (2×), and brine (1×), then dried over sodium sulfate. Concentration under reduced pressure yielded solid product, which was filtered and washed with hexanes. Additional product was obtained by purifying the filtrate via silica gel column chromatography (0 to 8% ethyl acetate in hexanes) followed by a final wash of product-containing fractions with hexanes. Combined yield was 1.69 g (29%). $^1$H NMR (500 MHz, CDCl$_3$): δ7.49-7.44 (m, 4H), 7.34-7.30 (m, 4H), 6.87 (t, J=1.9 Hz, 2H), 5.92 (s, 2H), 3.50 (p, J=1.6 Hz, 2H), 3.15 (s, 6H), 1.99 (dt, J=6.3, 1.6 Hz, 1H), 1.89 (dt, J=6.3, 1.7 Hz, 1H). $^{13}$C NMR (126 MHz, CDCl$_3$) δ153.8, 142.3, 142.2, 134.5, 131.5, 127.8, 121.5, 75.9, 74.1, 52.8, 49.8. IR (neat): 2983.3, 2931.2, 2873.7, 1481.0, 1392.1, 1299.1, 1070.9, 1007.4, 938.4, 823.3, 726.6, 681.9 cm$^{-1}$. HRMS (TOF MS EI+) (m/z): [M]$^+$ calculated for C$_{25}$H$_{22}$Br$_2$O$_2$: 511.9987; found: 511.9997. See FIGS. 17A and 17B for proton and carbon NMR spectra.

Example 2

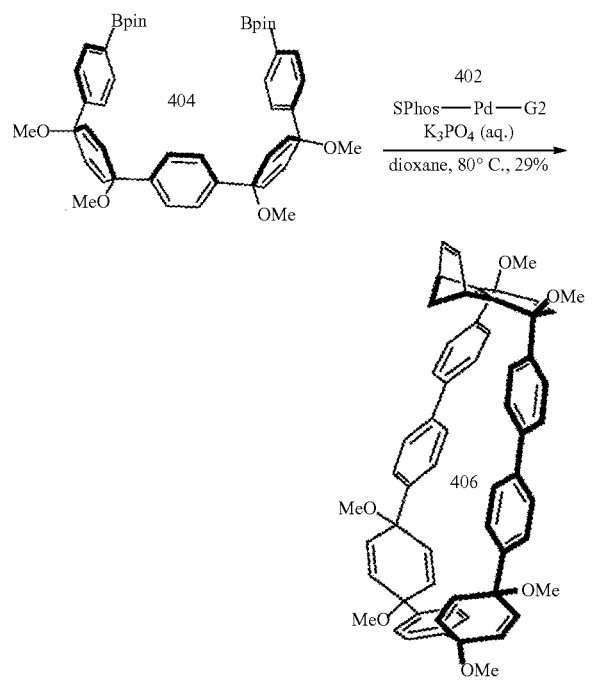

Figure 17C:
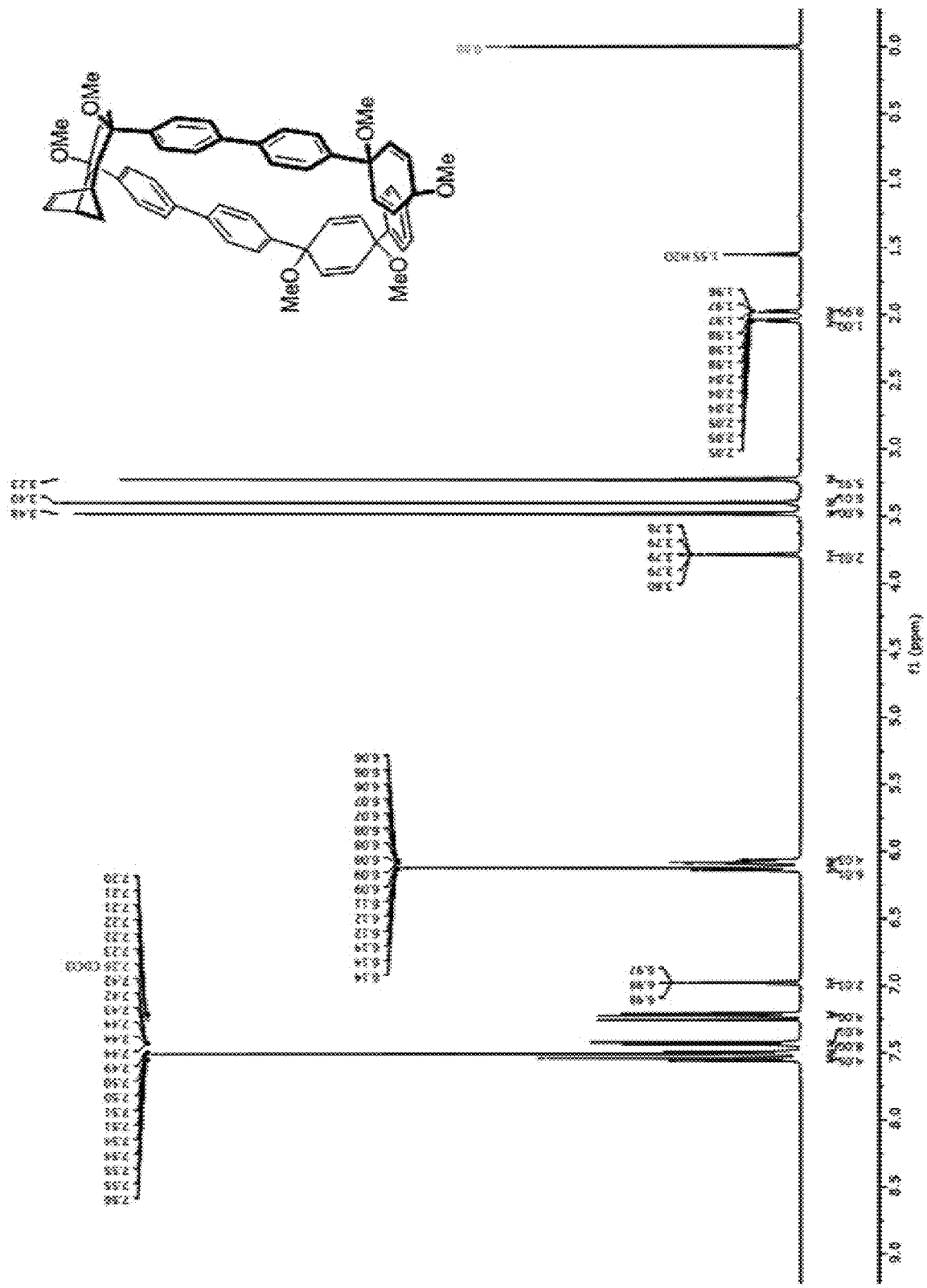
Figure 17D:
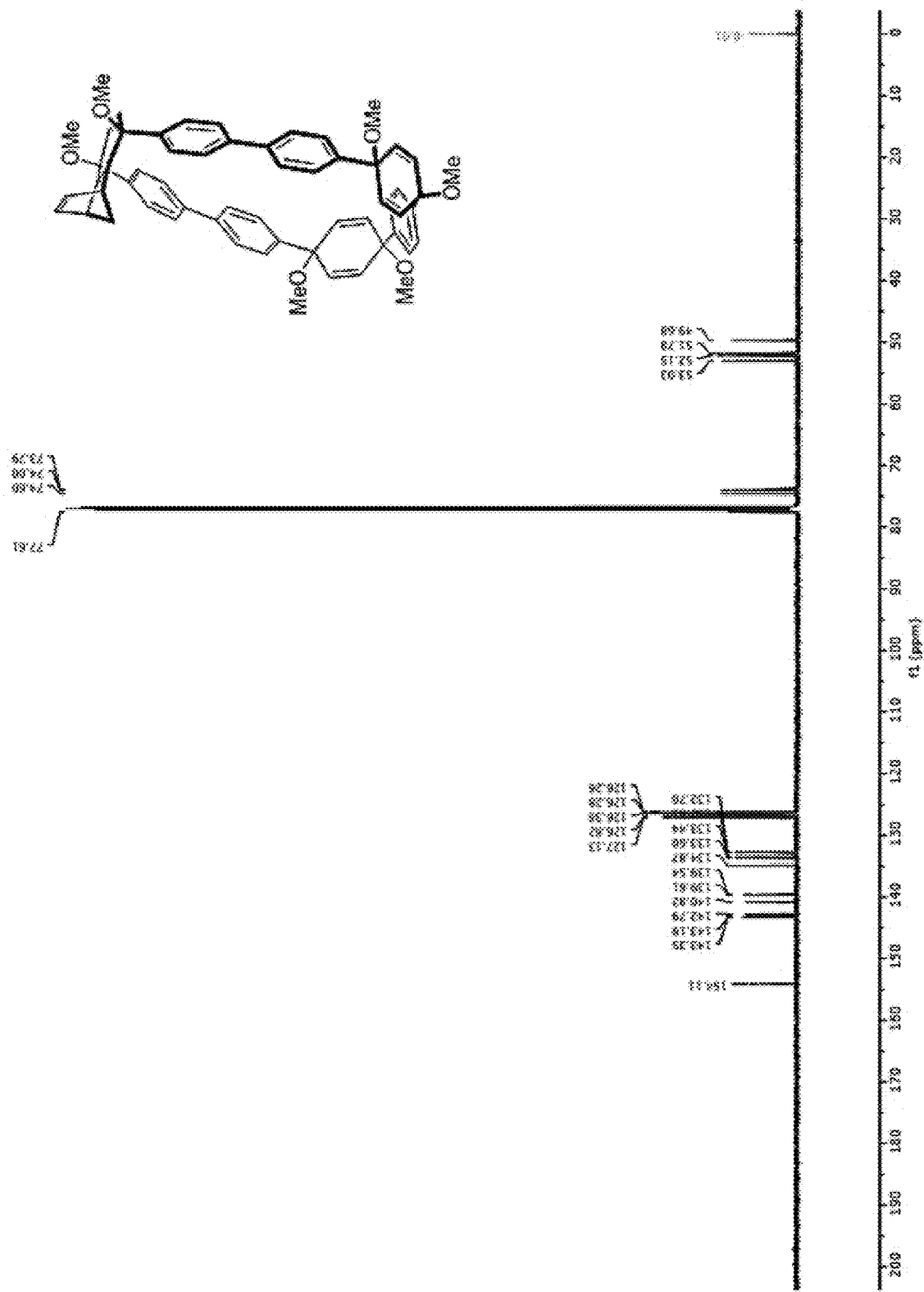

A flame-dried flask was charged with dibromide 402 (300 mg, 0.583 mmol, 1.00 equiv.), bisboronate 404 (487 mg, 0.642 mmol, 1.10 equiv.), and SPhos-Pd-G2 (42 mg, 0.058 mmol, 0.10 equiv.). The flask was evacuated and backfilled with nitrogen for 5 cycles. Dry dioxane (195 mL) was sparged with nitrogen for 1 hr. A 2.00 M. aqueous solution of K$_3$PO$_4$ was sparged with nitrogen for 1 hr. Dioxane was added to the reaction flask, which was then heated to 80° C. 19.5 mL of K$_3$PO$_4$ solution was added. The reaction was stirred overnight at 80° C. After the reaction was cooled to room temperature, the dioxane was removed under reduced pressure, then the resulting material was extracted with DCM (3×). The combined organic layers were washed with water (2×) and brine (1×), then dried over sodium sulfate, filtered through celite, and concentrated under reduced pressure. Silica gel column chromatography on the filtrate (6 to 16% ethyl acetate in 50/50 DCM/hexanes) yielded 160 mg (29%). $^1$H NMR (500 MHz, CDCl$_3$): δ7.55 (d, J=8.6 Hz, 4H), 7.51 (s, 4H), 7.50 (d, J=7.9 Hz, 4H), 7.43 (d, J=8.7 Hz, 4H), 7.21 (d, J=8.6 Hz, 4H), 6.98 (t, J=1.8 Hz, 2H), 6.14-6.06 (m, 10H), 3.79 (t, J=1.5 Hz, 2H), 3.48 (s, 6H), 3.40 (s, 6H), 3.23 (s, 6H), 2.04 (d, 1 H), 1.97 (d, J=6.4 Hz, 1 H). $^{13}$C NMR (126 MHz, CDCl$_3$) δ154.11, 143.35, 143.19, 142.79, 140.82, 139.61, 139.54, 134.87, 133.60, 133.44, 132.83, 132.70, 127.13, 126.82, 126.38, 126.28, 126.26, 77.61, 74.60, 74.00, 73.79, 53.03, 52.15, 51.78, 49.68. IR (neat): 2934.9, 2897.5, 2821.1, 1712.9, 1491.7, 1448.9, 1397.2, 1175.2, 1073.9, 946.7, 818.3 cm$^{-1}$. HRMS (TOF MS EI+) (m/z): [M]$^+$ calculated for C$_{59}$H$_{54}$O$_6$: 858.3920; found: 858.3954. See FIGS. 17C and 17D for proton and carbon NMR spectra.

Example 3

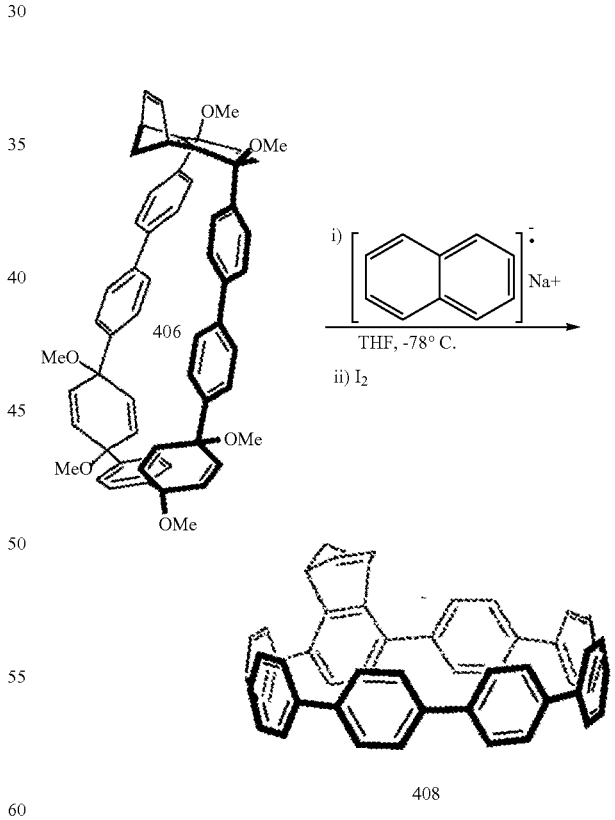

Figure 18A:
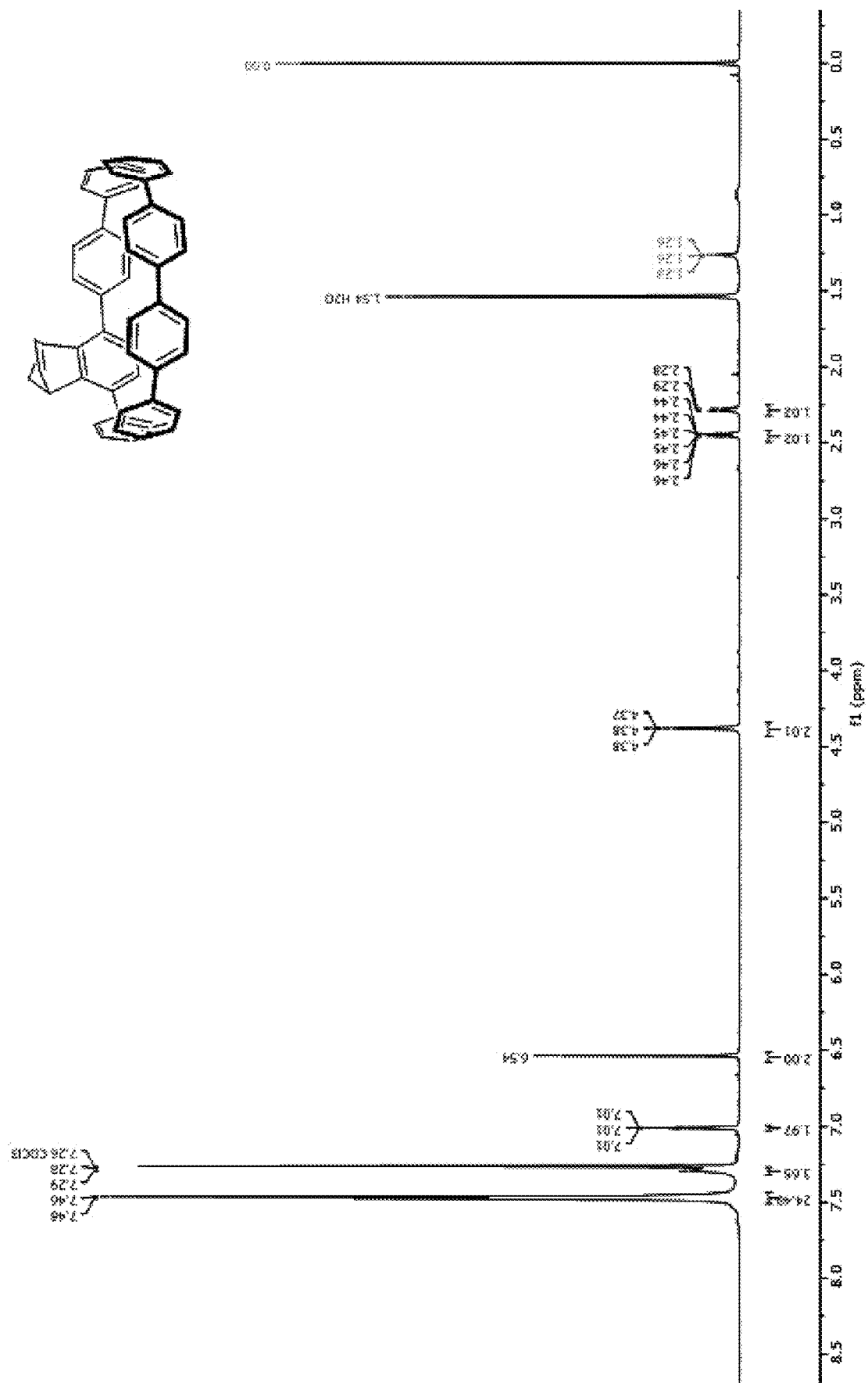
FIGS. 18A and 18B are proton NMR spectra (FIG. 18A) and carbon NMR spectra (FIG. 18B) of polymerizable nanohoop monomer 408.
Figure 18B:
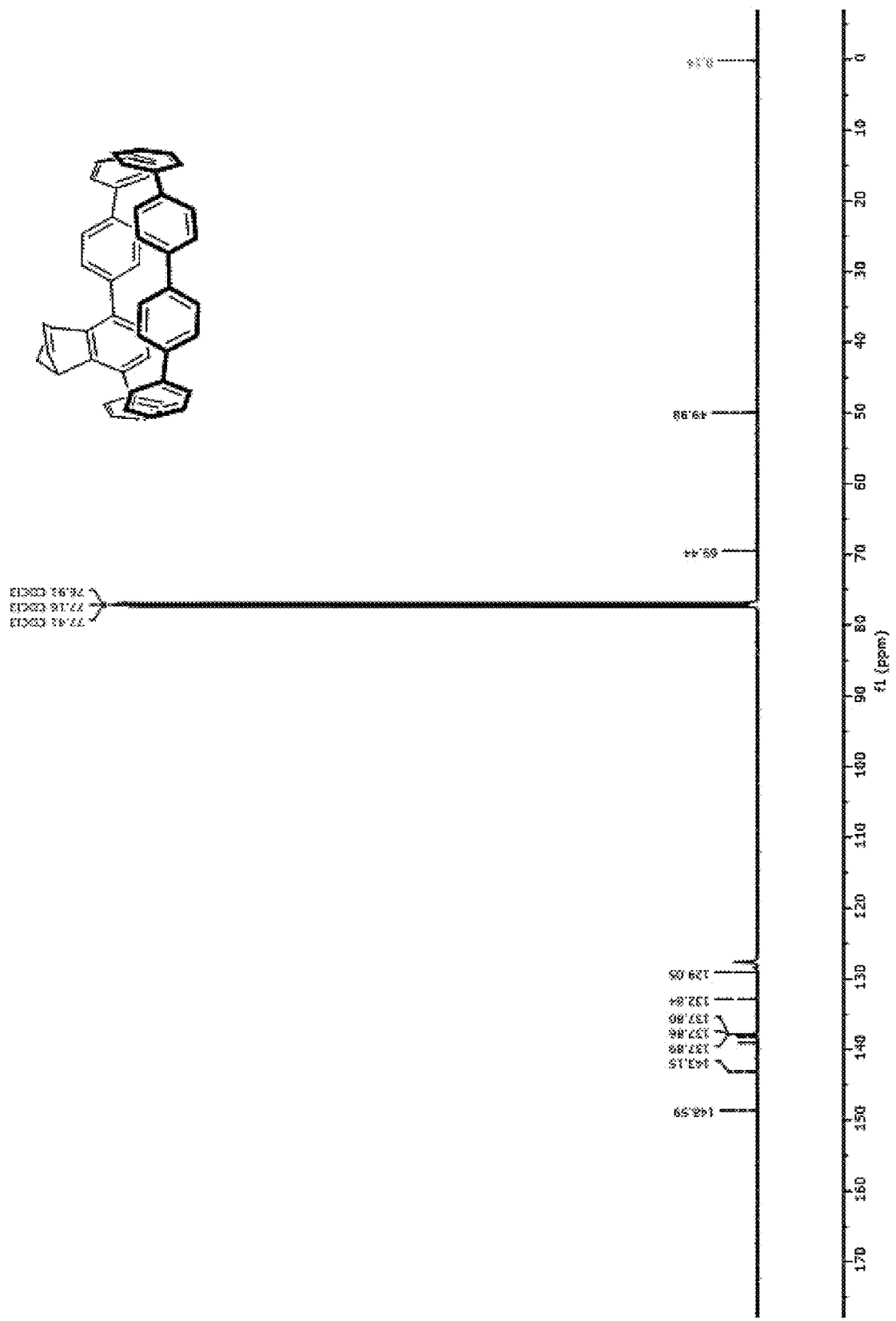
Figure 19A:
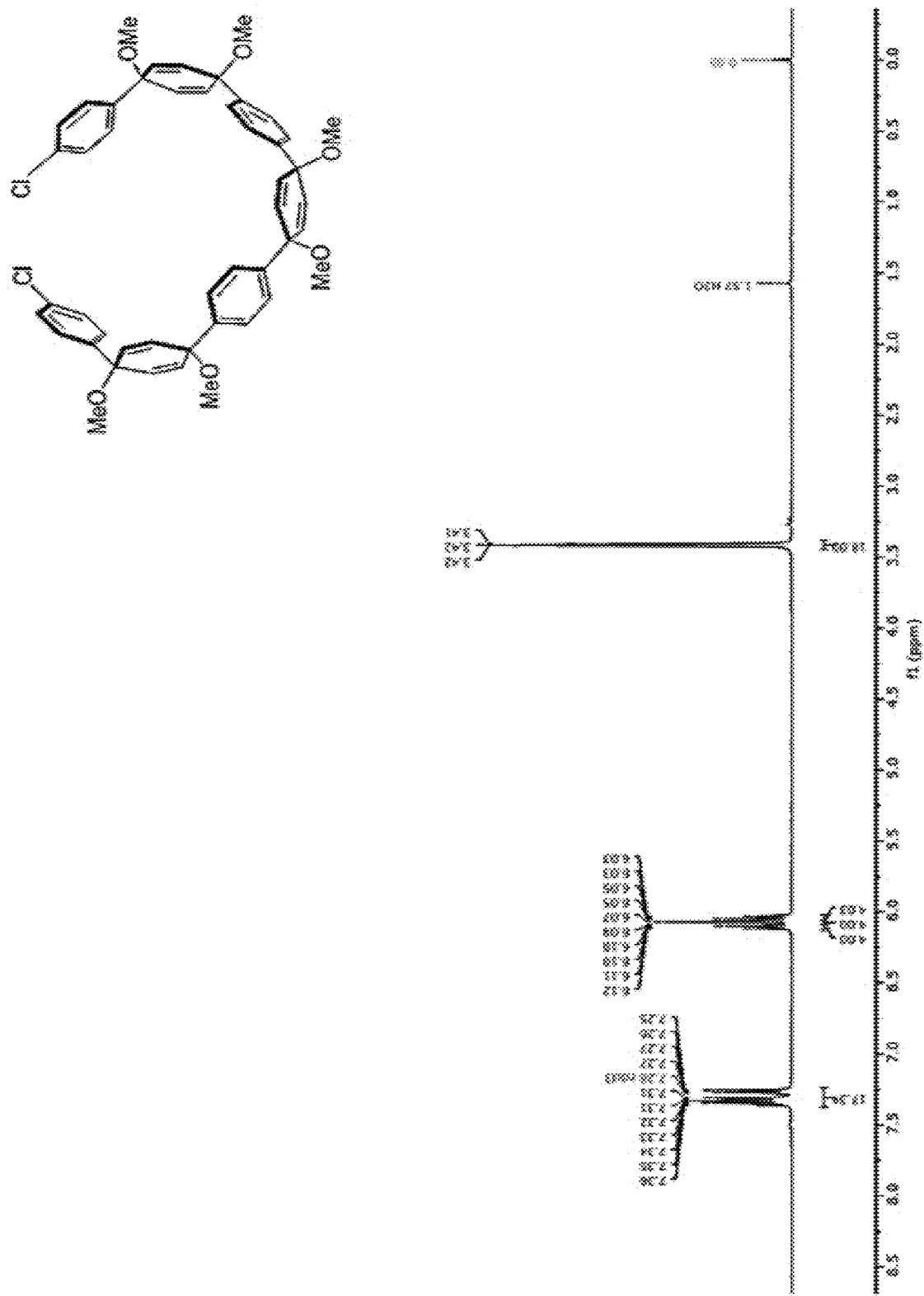
FIGS. 19A-19F are proton NMR spectra (FIGS. 19A, 19C, and 19E) and carbon NMR spectra (FIGS. 19B, 19D, and 19F) of intermediates 510 (FIGS. 19A and 19B), 500 (FIGS. 19C and 19D), and 502 (FIGS. 19E and 19F).
Figure 19B:
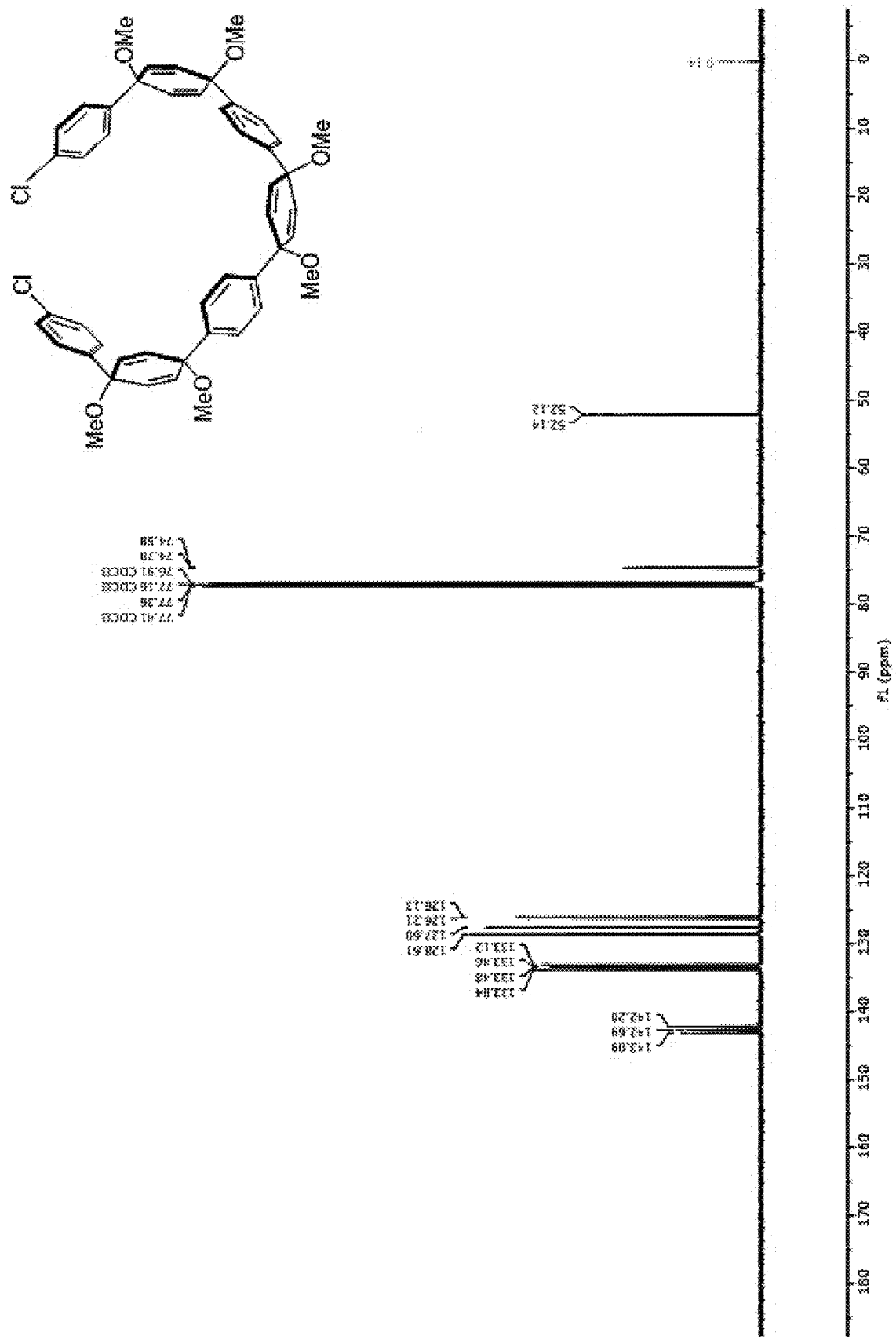

A 0.5 M. sodium naphthalenide solution was prepared by sonicating sodium and naphthalene in THF in a flame-dried flask, then stirring the solution overnight. Macrocycle 406 (83 mg, 0.097 mmol, 1.00 equiv.) was dispersed in THF in a flame-dried flask and stirred at -78° C. for 30 min. Sodium naphthalenide (>2.90 mL, 1.45 mmol, 15.00 equiv.) was added dropwise to the reaction flask until the mixture was brown. The reaction was stirred for 30 minutes and then quenched with dropwise addition of 1 M. iodine solution in THF until orange. Sodium thiosulfate was added until the orange color dissipated, and the reaction was warmed to room temperature. THF was removed under reduced pressure, and the resulting solution was extracted with DCM (3×). The combined organic layers were washed with water (2×) and brine (1×), then dried over sodium sulfate and concentrated under reduced pressure. Automated silica gel column chromatography (5 to 40% DCM in hexanes) yielded 55 mg 408 (85%). $^1$H NMR (500 MHz, CDCl$_3$): δ (ppm) 7.47 (overlapping, 24H), 7.28 (d, J=7.9 Hz, 4H), 7.01 (t, J=1.9 Hz, 2H), 6.53 (s, 2H), 4.38 (t, J=1.9 Hz, 2H), 2.45 (dt, J=7.2, 1.6 Hz, 1H), 2.28 (d, J=7.4 Hz, 1H). $^{13}$C NMR (126 MHz, CDCl$_3$) δ148.59, 143.15, 139.08, 138.25, 138.05, 137.91, 137.89, 137.86, 137.80, 132.84, 129.05, 69.44, 49.98. IR (neat): 3021.8, 1889.6, 1582.9, 1480.7, 1388.8, 1256.9, 998.7, 942.1, 809.7, 723.2 cm$^{-1}$. HRMS (TOF MS EI+) (m/z): [M]$^+$ calculated for C$_{53}$H$_{36}$: 672.2817; found: 672.2833. See FIGS. 18A and 18B for proton and carbon NMR spectra.

dry DMF (5 mL) were added. The reaction was allowed to warm to room temperature overnight. The reaction was quenched with water and extracted with diethyl ether (3×). The combined organic layers were washed with 5% aqueous LiCl (3×), water (2×), and brine (1×), then dried over sodium sulfate and concentrated under reduced pressure. The material was sonicated with hexanes until solid formed, then it was filtered and washed with hexanes. The product was purified further by automated silica gel chromatography in 5 to 12% ethyl acetate in hexanes. 1.50 g were collected (46%). $^1$H NMR (500 MHz, CDCl$_3$): δ7.37-7.24 (overlapping, 16H), 6.11 (d, J=10.2 Hz, 4H), 6.07 (s, 4H), 6.04 (d, J=10.4 Hz, 4H), 3.43-3.40 (overlapping, 18H). $^{13}$C NMR (126 MHz, CDCl$_3$) δ143.09, 142.69, 142.20, 133.84, 133.48, 133.46, 133.12, 128.61, 127.60, 126.21, 126.13, 77.36, 74.70, 74.58, 52.14, 52.13, 52.12. IR (neat): 2939.8, 2819.0, 1489.0, 1452.1, 1403.3, 1228.2, 1179.3, 1070.6, 1013.2, 947.7, 820.3, 729.2, 664.0 cm$^{-1}$. HRMS (TOF MS EI+) (m/z): [M]$^+$ calculated for C$_{48}$H$_{46}$Cl$_2$O$_6$: 788.2671; found: 788.2695. See FIGS. 19A and 19B for proton and carbon NMR spectra.

Example 4

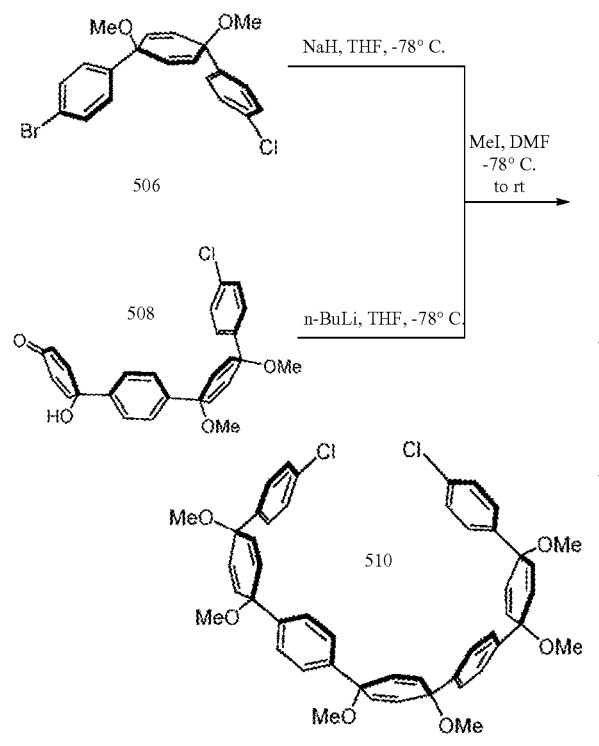

Example 5

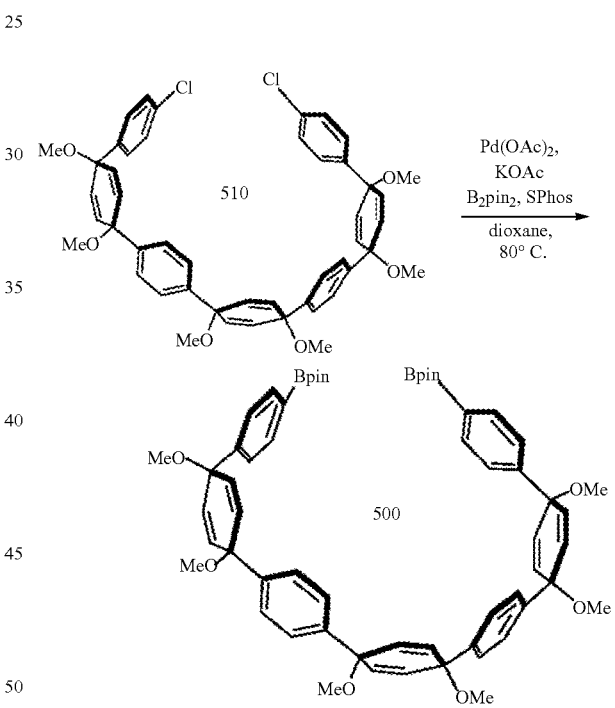

To a slurry of sodium hydride (220 mg, 5.4 mmol, 1.30 equiv.) in 10 mL THF was added a solution of ketone 508 (1.80 g, 4.1 mmol, 1.00 equiv.) in 10 mL THF at -78° C. The reaction mixture was stirred for 2 hr at -78° C. In a separate flask, bromochloride 506 (2.52 g, 6.2 mmol, 1.50 equiv.) was dissolved in 20 mL THF. This solution was cooled to -78° C., then n-BuLi (2.4 mL, 5.8 mmol, 1.40 equiv.) was added dropwise and the reaction was stirred for 30 min. This mixture was then transferred to the slurry containing the deprotonated ketone. The resulting mixture was stirred for 2 hr, at which time MeI (2.6 mL, 4.1 mmol, 10.00 equiv.) and Potassium acetate (373 mg, 3.8 mmol, 6.00 equiv.) was flame-dried in a flask and cooled under nitrogen. Ground B$_2$pin$_2$ (482 mg, 1.9 mmol, 3.00 equiv.), dichloride 510 (500 mg, 0.6 mmol, 1.00 equiv.), Pd(OAc)$_2$ (14 mg, 0.1 mmol, 0.10 equiv.), and SPhos (68 mg, 0.2 mmol, 0.26 equiv.) were added to the flask, which was then evacuated and backfilled with nitrogen for 5 cycles. The flask was sealed with a septum and purged with nitrogen for 1 hr. Dry dioxane (5 mL) was sparged with nitrogen for 1 hr then added to reaction flask. The reaction was heated to 80° C., then stirred overnight. After the reaction was cooled to room temperature, the mixture was filtered through a plug of celite, and the filtrate was concentrated under reduced pressure.

Figure 19C:
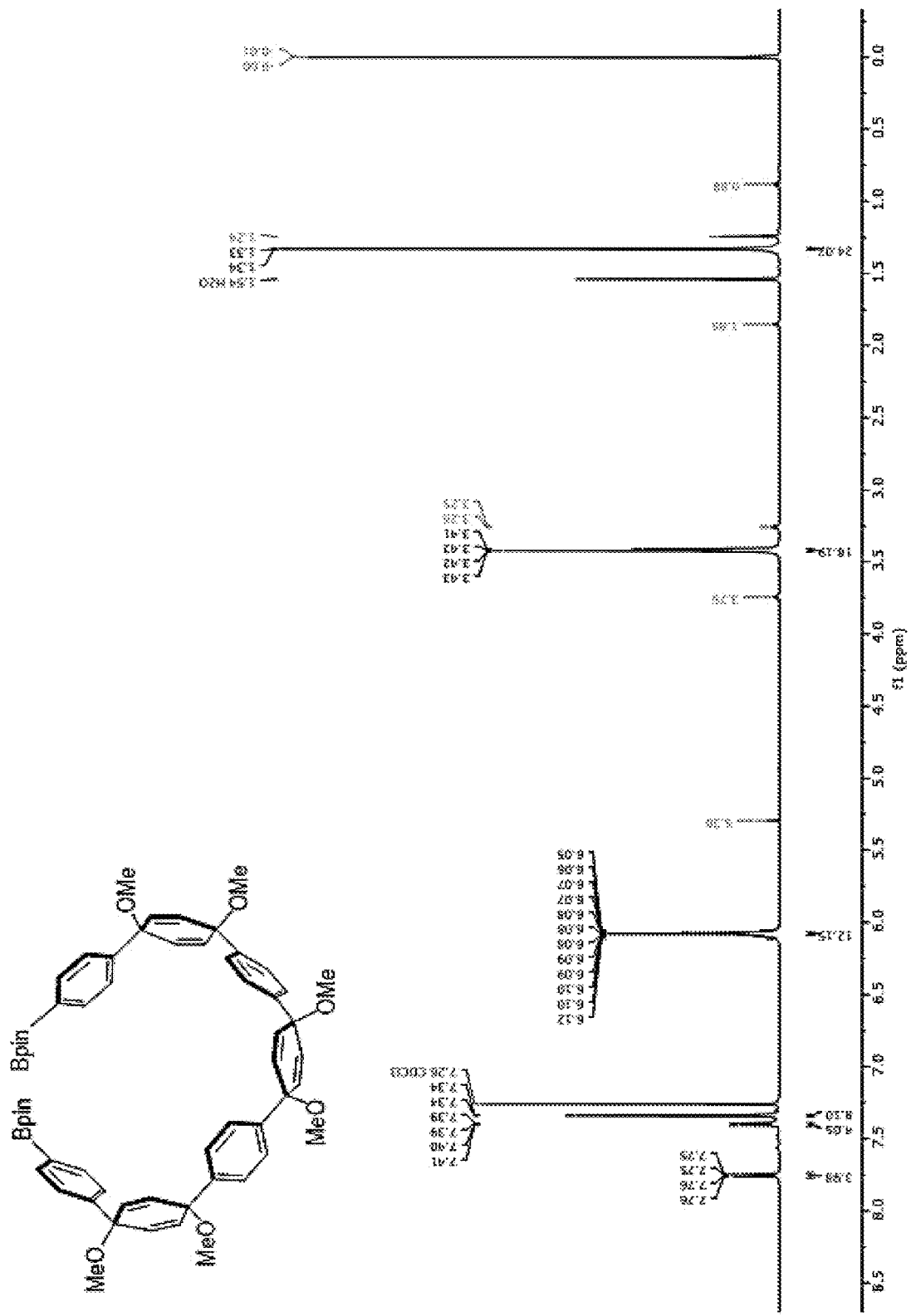
Figure 19D:
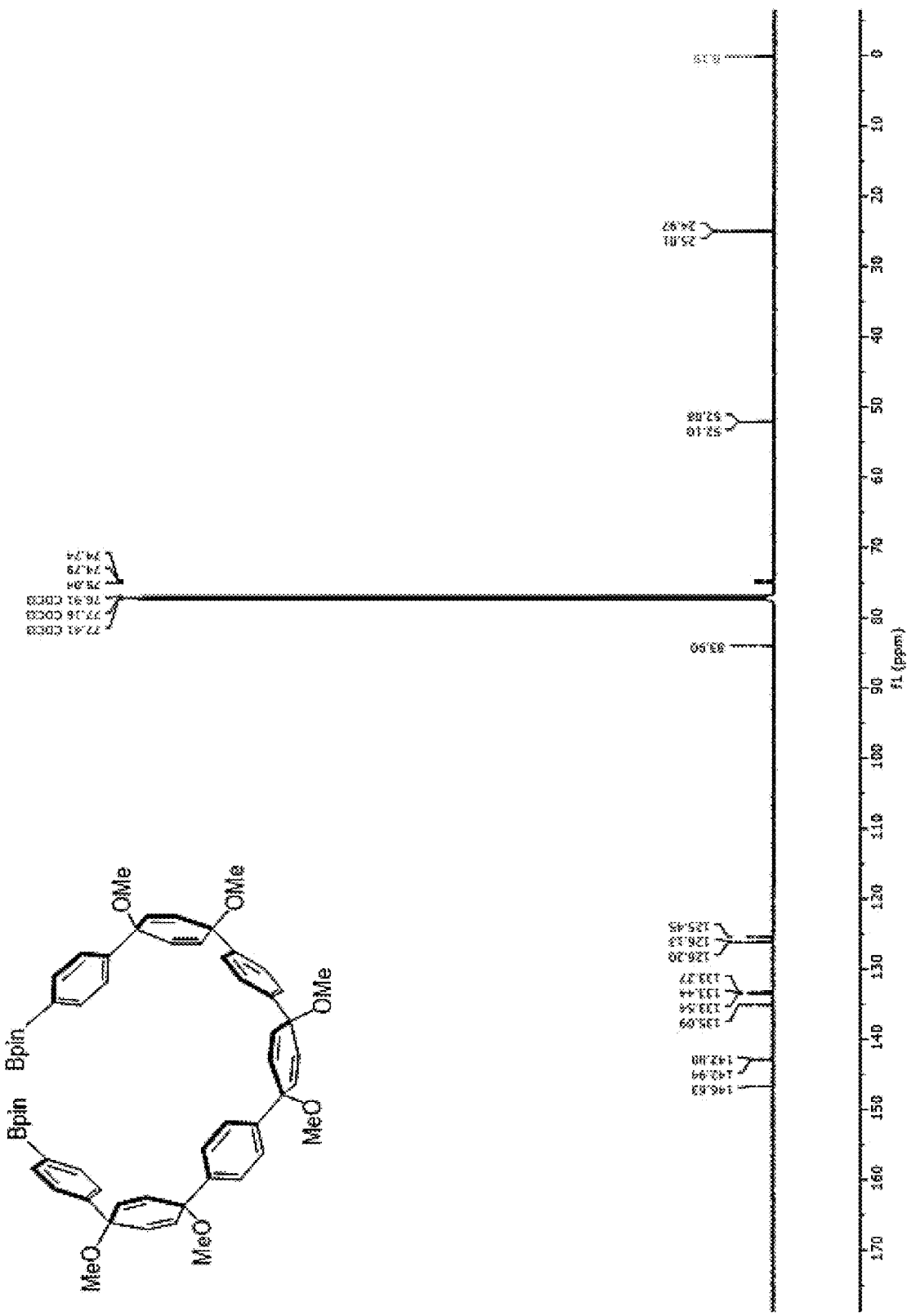

The material was sonicated with methanol and filtered. The product was then run through a very short silica plug using ethyl acetate and concentrated again to yield 430 mg (70%). $^1$H NMR (500 MHz, CDCl$_3$): δ7.75 (d, J=8.0 Hz, 4H), 7.40 (d, J=8.3 Hz, 4H), 7.34 (s, 8H), 6.10-6.06 (m, 12H), 3.42 (m, 18H), 1.33 (s, 24H). $^{13}$C NMR (126 MHz, CDCl$_3$) δ146.63, 142.94, 142.80, 135.09, 133.54, 133.48, 133.44, 133.27, 126.20, 126.13, 125.45, 83.90, 75.04, 74.79, 74.74, 52.10, 52.08, 25.01, 24.97. IR (neat): 2979.9, 2938.2, 2896.7, 2821.6, 1501.1, 1489.4, 1450.9, 1403.2, 1358.1, 1179.3, 1079.3, 1013.8, 948.7, 826.4, 757.3, 657.2 cm$^{-1}$. HRMS (FTMS ESI) (m/z): [M$^+$ Na]+calculated for C$_{60}$H$_{70}$B$_2$O$_{10}$Na: 995.5047; found: 995.5031. See FIGS. 19C and 19D for proton and carbon NMR spectra.

Example 6

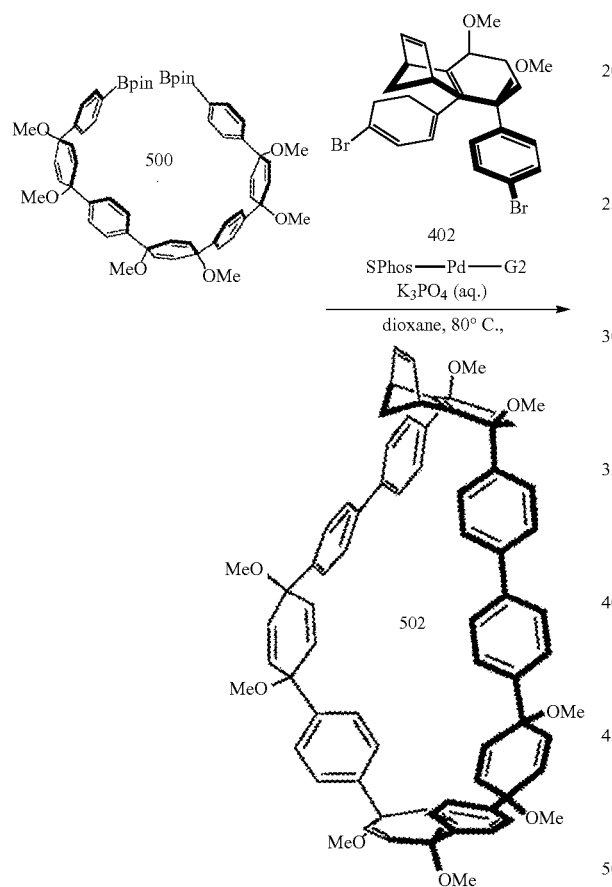

Figure 19E:
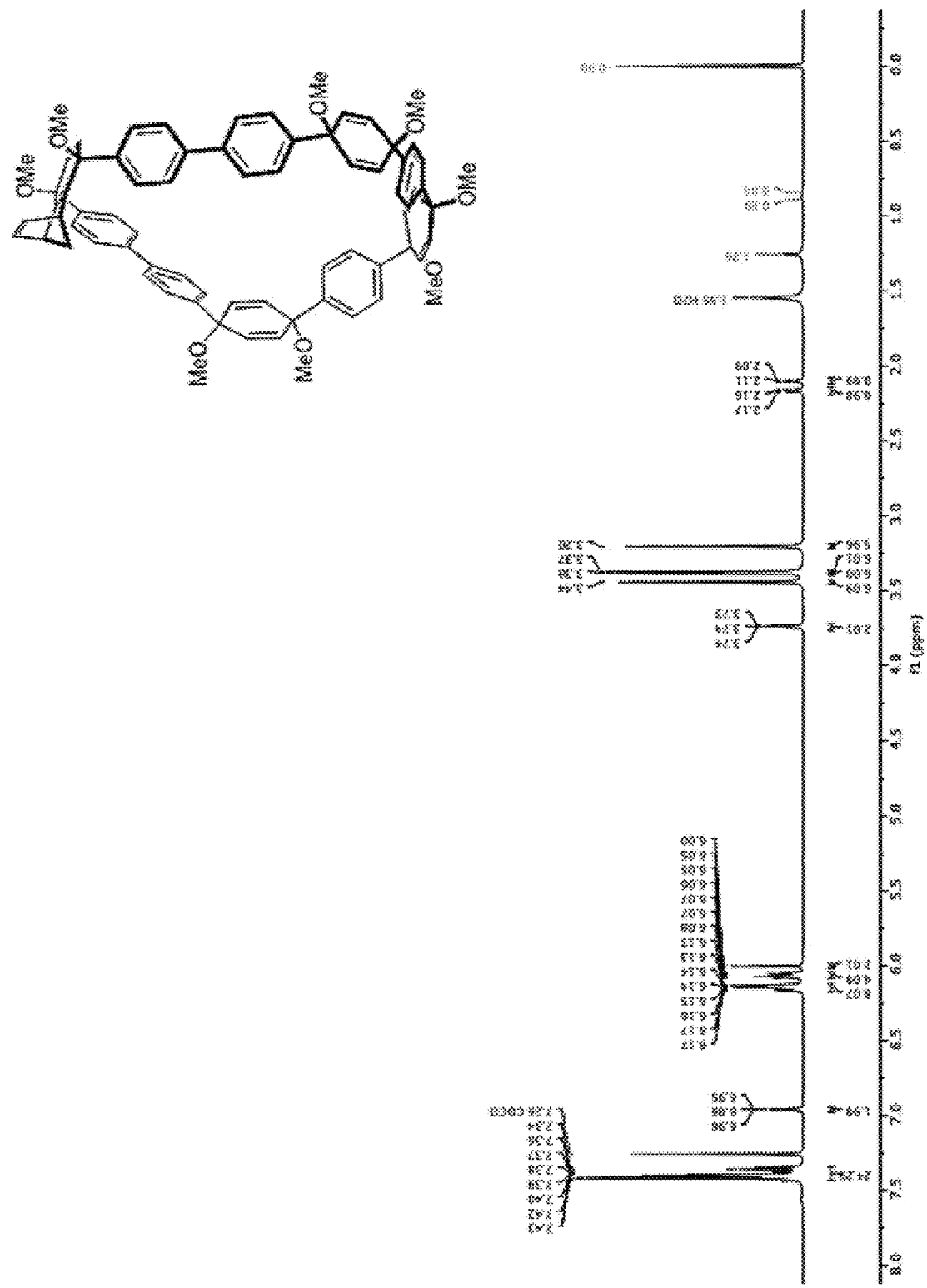
Figure 19F:
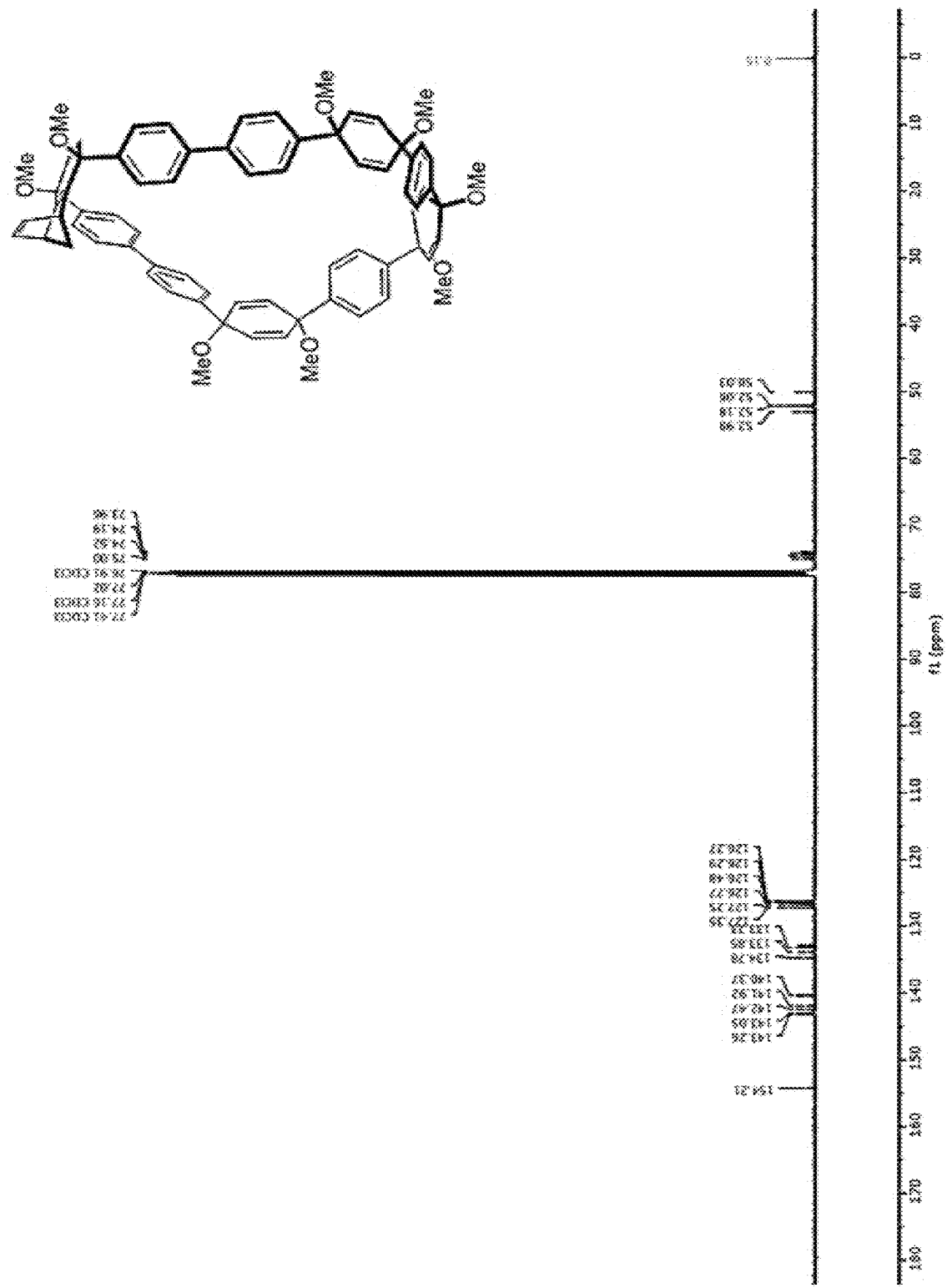

A flame-dried flask was charged with dibromide 402 (720 mg, 1.40 mmol, 1.00 equiv.), bisboronate 500 (1.43 g, 1.47 mmol, 1.05 equiv.), and SPhos-Pd-G2 (101 mg, 0.14 mmol, 0.10 equiv.). The flask was evacuated and backfilled with nitrogen for 5 cycles. The flask was then purged with nitrogen. A 2.00 M. aqueous solution of K$_3$PO$_4$ was sparged with nitrogen for 1 hr. Dioxane (470 mL) was added to the reaction flask via cannulation, and the solution was sparged for 20 min. before being heated to 80° C. for 10 min. 47 mL of K$_3$PO$_4$ solution was added, and the reaction was stirred for 30 min. at 80° C. After the reaction was cooled to room temperature, the dioxane was removed under reduced pressure, then the resulting material was filtered through a celite pad with DCM and water. The filtrate was extracted with DCM (3×). The combined organic layers were washed with water (2×) and brine (1×), then dried over sodium sulfate and concentrated under reduced pressure. The material was purified by automated silica gel column chromatography (0 to 14% ethyl acetate in DCM), then washed with acetone and filtered, yielding 415 mg (28%). $^1$H NMR (500 MHz, CDCl$_3$): δ7.43-7.35 (overlapping, 24H), 6.96 (s, 2H), 6.17-6.14 (overlapping, 8H), 6.07 (m, 4H), 6.00 (s, 2H), 3.73 (s, 2H), 3.44 (s, 6H), 3.38 (s, 6H), 3.37 (s, 6H), 3.20 (s, 6H), 2.17 (d, J=6.0 1H), 2.10 (d, J=6.2 Hz, 1H). $^{13}$C NMR (126 MHz, CDCl$_3$) δ154.21, 143.26, 143.05, 142.97, 142.47, 141.92, 140.42, 140.37, 134.78, 134.01, 133.85, 133.23, 133.02, 132.86, 127.35, 127.25, 126.77, 126.48, 126.29, 126.27, 77.02, 75.00, 74.52, 74.19, 73.96, 52.98, 52.18, 52.06, 50.03. IR (neat): 2978.9, 2936.2, 2896.6, 2821.4, 1608.8, 1490.1, 1450.6, 1403.0, 1358.2, 1173.4, 1072.8, 1013.7, 948.0, 822.2, 656.74 cm$^{-1}$. HRMS (TOF MS EI+) (m/z): [M+Na]$^+$ calculated for C$_{73}$H$_{68}$O$_8$Na: 1095.4812; found: 1095.4840. See FIGS. 19E and 19F for proton and carbon NMR spectra.

Example 7

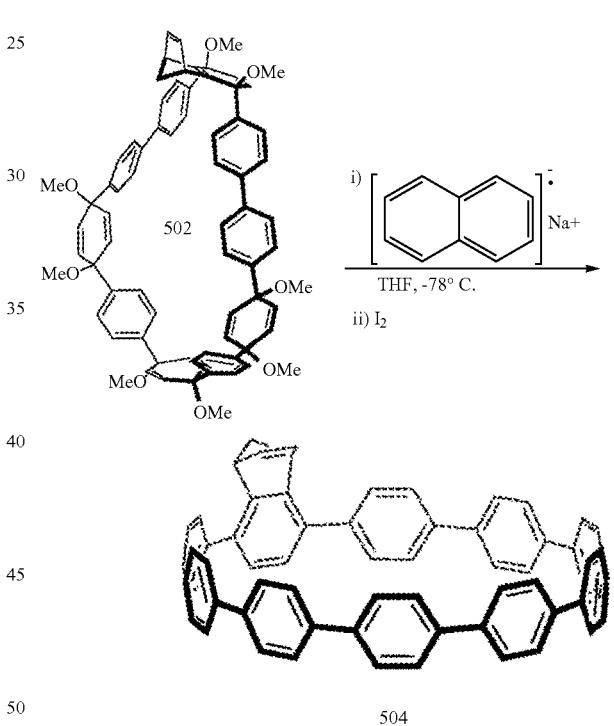

Figure 20A:
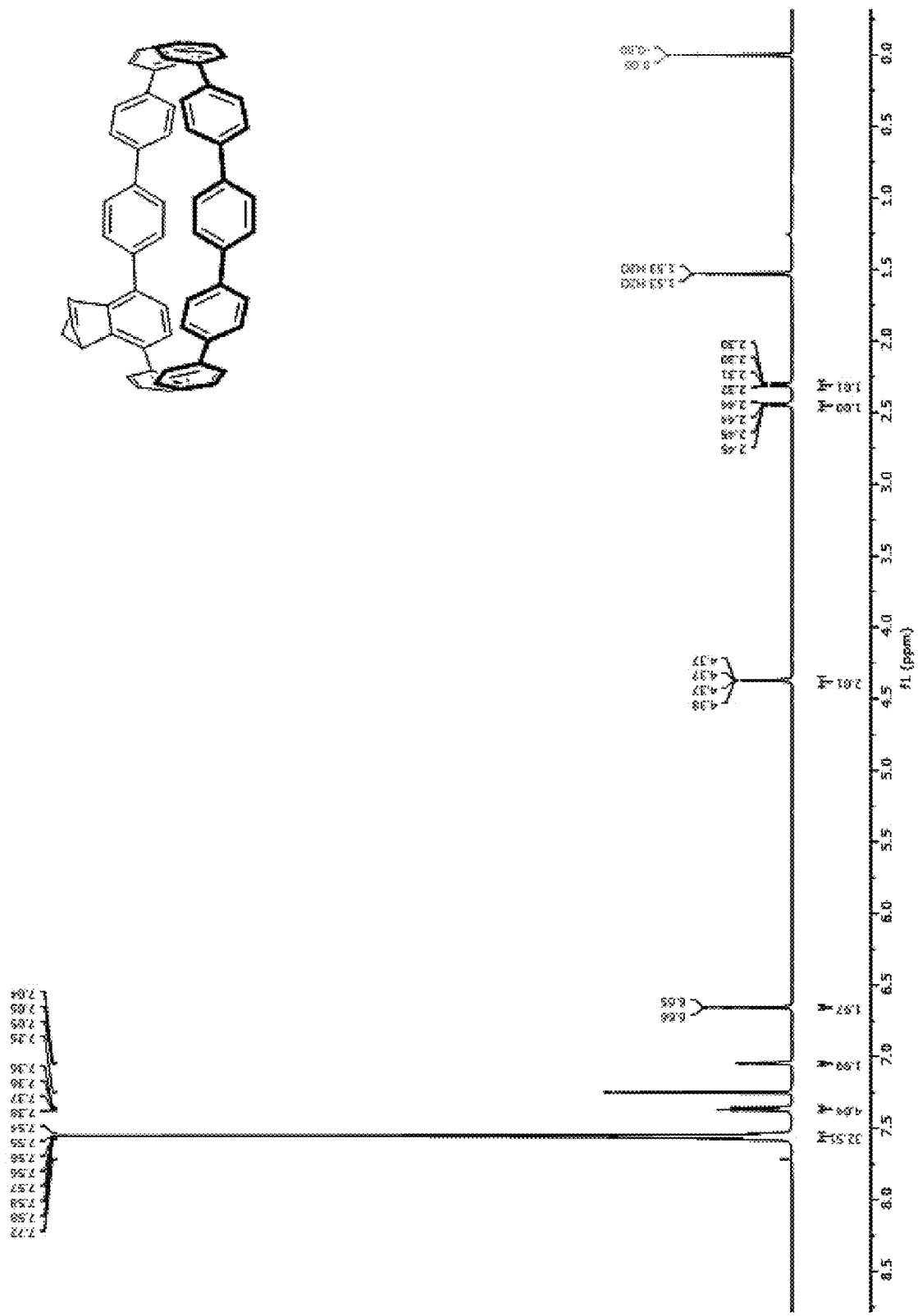
FIGS. 20A and 20B are proton NMR spectra (FIG. 20A) and carbon NMR spectra (FIG. 20B) of polymerizable nanohoop monomer 504.
Figure 20B:
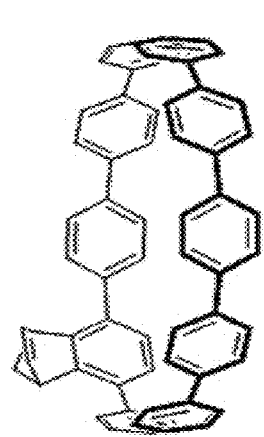
Figure 20B:
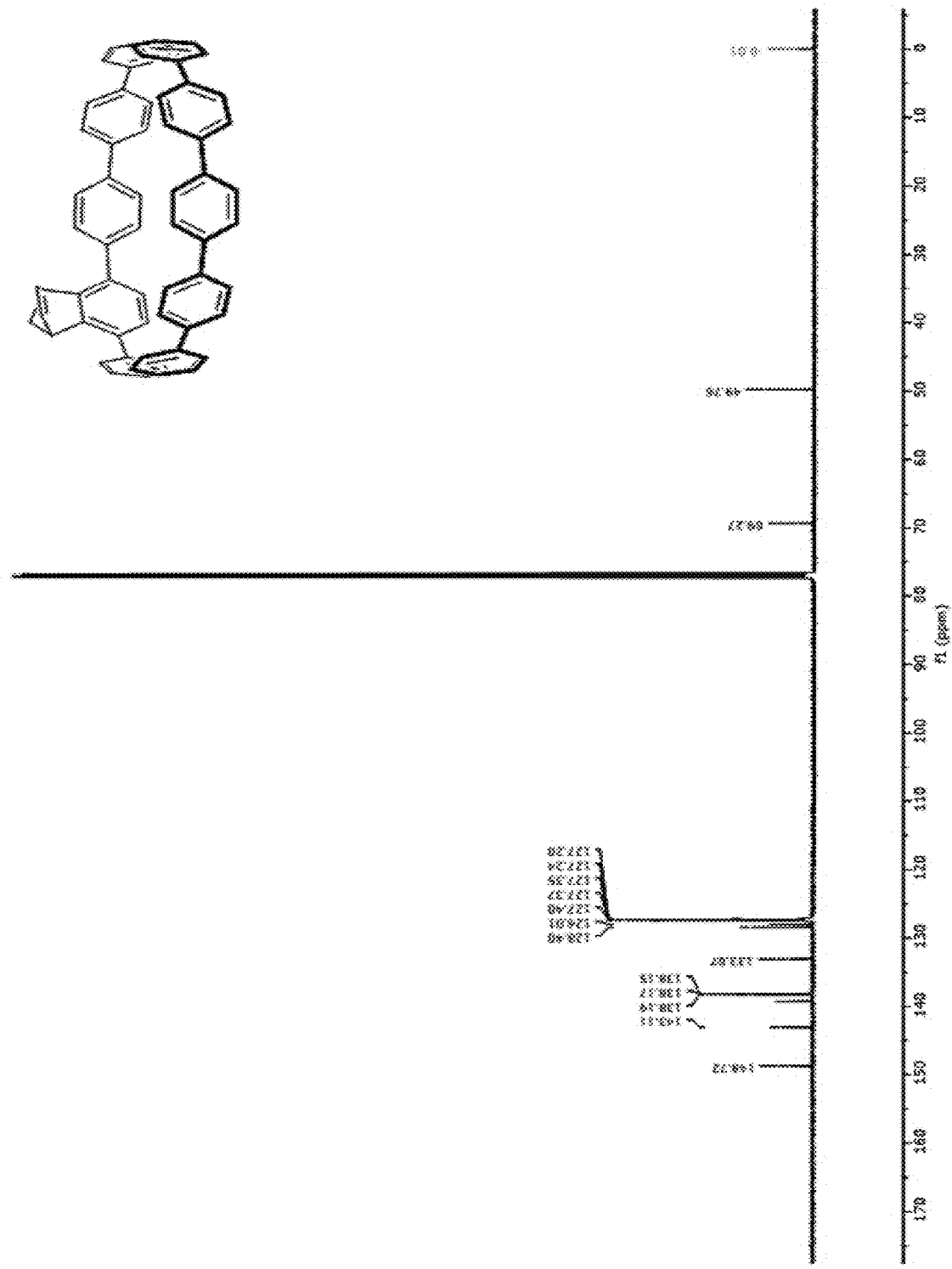

A 0.5 M. sodium naphthalenide solution was prepared by sonicating sodium and naphthalene in THF in a flame-dried flask, then stirring the solution overnight. Macrocycle 502 (395 mg, 0.368 mmol, 1.00 equiv.) was dispersed in THF in a flame-dried flask and stirred at −78° C. for 30 min. Sodium naphthalenide (>11.0 mL, 5.52 mmol, 15.00 equiv.) was added dropwise to the reaction flask until the mixture was brown. The reaction was stirred for 20 minutes and then quenched with dropwise addition of 1 M. iodine solution in THF until orange. Sodium thiosulfate was added until the orange color dissipated, and the reaction was warmed to room temperature. The resulting solution was extracted with DCM (3×). The combined organic layers were washed with water (2×) and brine (1×), then dried over sodium sulfate and concentrated under reduced pressure. The material was adsorbed on silica and purified by automated silica gel column chromatography (15-35% DCM in hexanes), yielding 229 mg (75%). $^1$H NMR (500 MHz, CDCl$_3$): δ7.56 (overlapping, 32H), 7.36 (d, J=8.2 Hz, 4H), 7.05 (t, J=1.7 Hz, 2H), 6.65 (s, 2H), 4.37 (s, 2H), 2.45 (d, J=7.6 Hz, 1 H), 2.31 (d, J=7.3 Hz, 1 H). $^{13}$C NMR (126 MHz, CDCl$_3$) δ148.72, 143.11, 139.27, 138.26, 138.19, 138.17, 138.15, 133.07, 128.40, 128.01, 127.40, 127.37, 127.35, 127.24, 127.20, 69.27, 49.76. IR (neat): 3021.3, 1895.4, 1589.7, 1479.3, 1386.6, 1000.2, 905.4, 805.7, 730.6 cm$^{-1}$. HRMS (TOF MS EI+) (m/z): [M]$^+$ calculated for C$_{65}$H$_{44}$: 824.3443; found: 824.3467. See FIGS. 20A and 20B for proton and carbon NMR spectra.

Example 8

Figure 2:
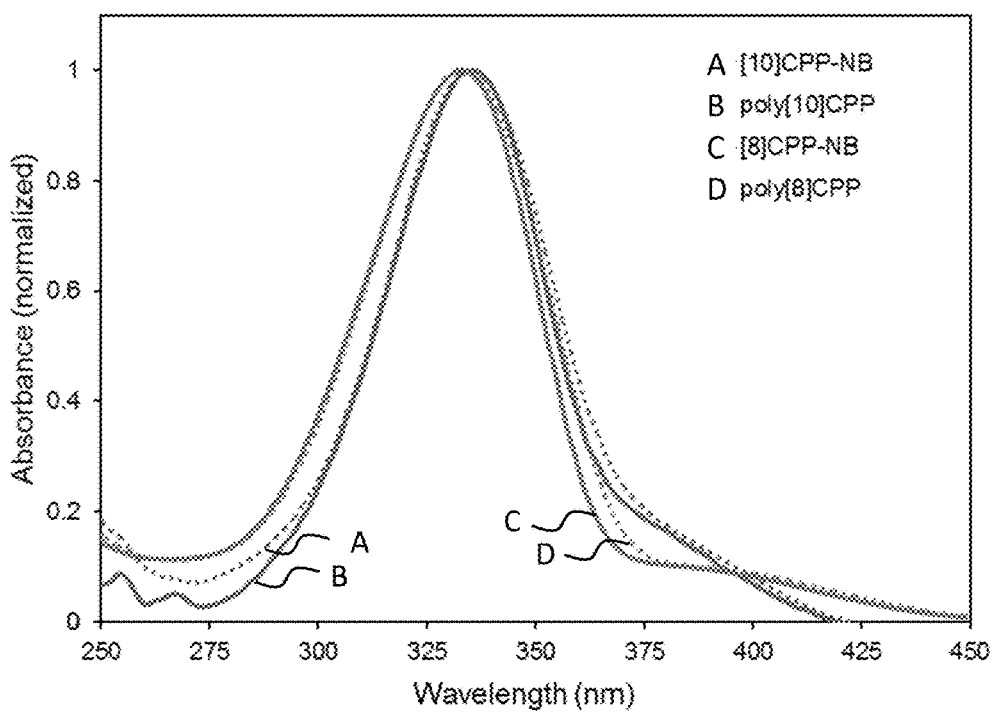
FIG. 2 shows absorbance spectra of monomers and polymers measured in THF, wherein exemplary CPP-NB monomers and poly-CPPs share the common absorbance of underivatized CPPs near 340 nm.
Figure 3:
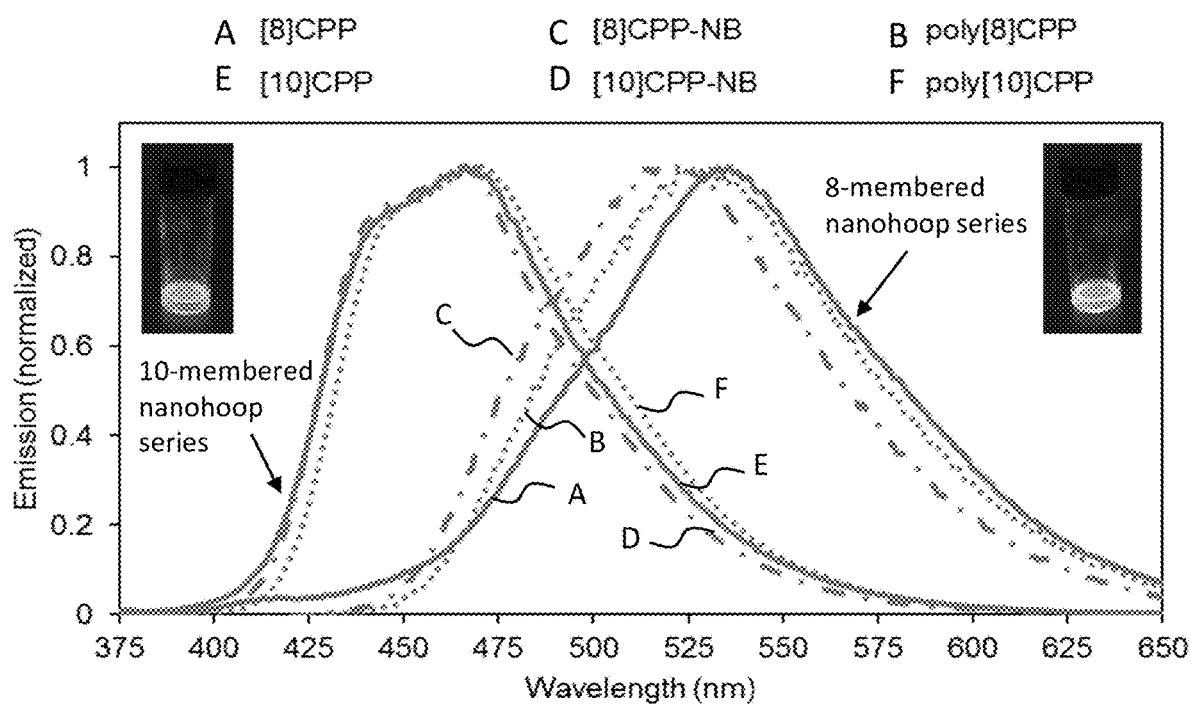
FIG. 3 shows fluorescence emission maxima for polymerizable nanohoop monomer 408 (521 nm) and polymerizable nanohoop monomer 504 (462 nm), which match closely with [8]CPP (533 nm) and [10]CPP (466 nm), respectively; the insets show samples of poly[10]CPP (left) and poly[8]CPP (right) under long-wave UV light.
Figure 4A:
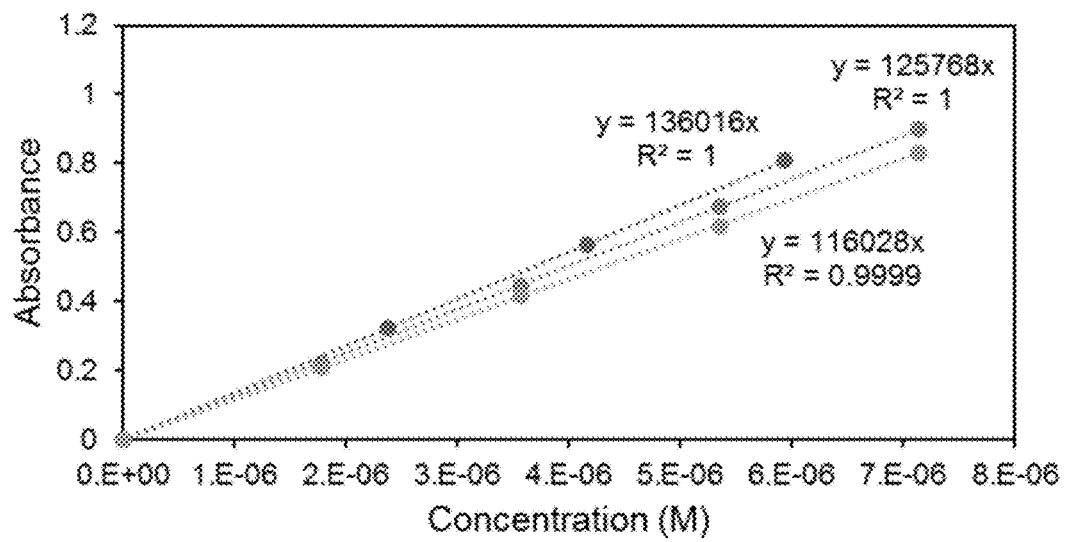
FIGS. 4A and 4B show experimental and fitted data for the extinction coefficients measurements for polymerizable nanohoop monomer 408 (FIG. 4A) and polymerizable nanohoop monomer 504 (FIG. 4B), wherein the extinction coefficients were measured in THF.
Figure 4B:
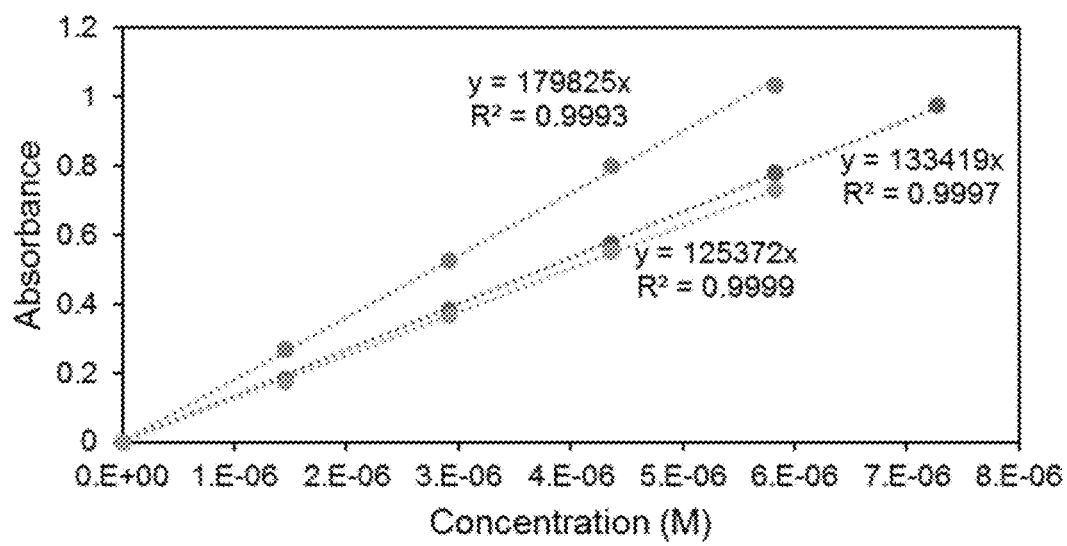

Before polymerization, each monomer was characterized using single crystal X-ray crystallography in addition to UV-vis absorbance and fluorescence spectroscopy. X-ray crystallography revealed that polymerizable nanohoop monomer 408 crystallized with the norbornene unit disordered over two positions, whereas polymerizable nanohoop monomer 504 crystallized with the norbornene alkene exclusively oriented toward the center of the macrocycle. The alkene bond angles in both monomers were between 107° and 110° (FIG. 1). polymerizable nanohoop monomer 408 and polymerizable nanohoop monomer 504 exhibit nearly identical characteristics to the corresponding unsubstituted CPPs in terms of both absorbance and emission (see FIG. 2 and FIG. 3). In underivatized CPPs, both extinction coefficient and quantum yield increase as the number of benzene rings increases, and this size-dependent trend holds true for polymerizable nanohoop monomer 408 and polymerizable nanohoop monomer 504 as well (see FIGS. 4A and 4B). Extinction coefficients were found to be 1.3×10$^5$ L·mol$^{-1}$cm$^{-1}$ and 1.5×10$^5$ L·mol$^{-1}$cm$^{-1}$ for polymerizable nanohoop monomer 408 and polymerizable nanohoop monomer 504, respectively.

Example 9

In this example, a general method for making a polymer embodiment is described. As a general procedure, a polymerizable nanohoop monomer is added to a small vial with a stir bar, placed under N$_2$, then dissolved in dry THF. A solution of bromopyridyl Grubbs G3 in THF is quickly added to the vial via syringe, and the reaction is stirred for 30 minutes or until all monomer is consumed. The reaction is quenched with ethyl vinyl ether, and the material is precipitated from cold methanol. The polymer is collected by vacuum filtration.

Figure 21A:
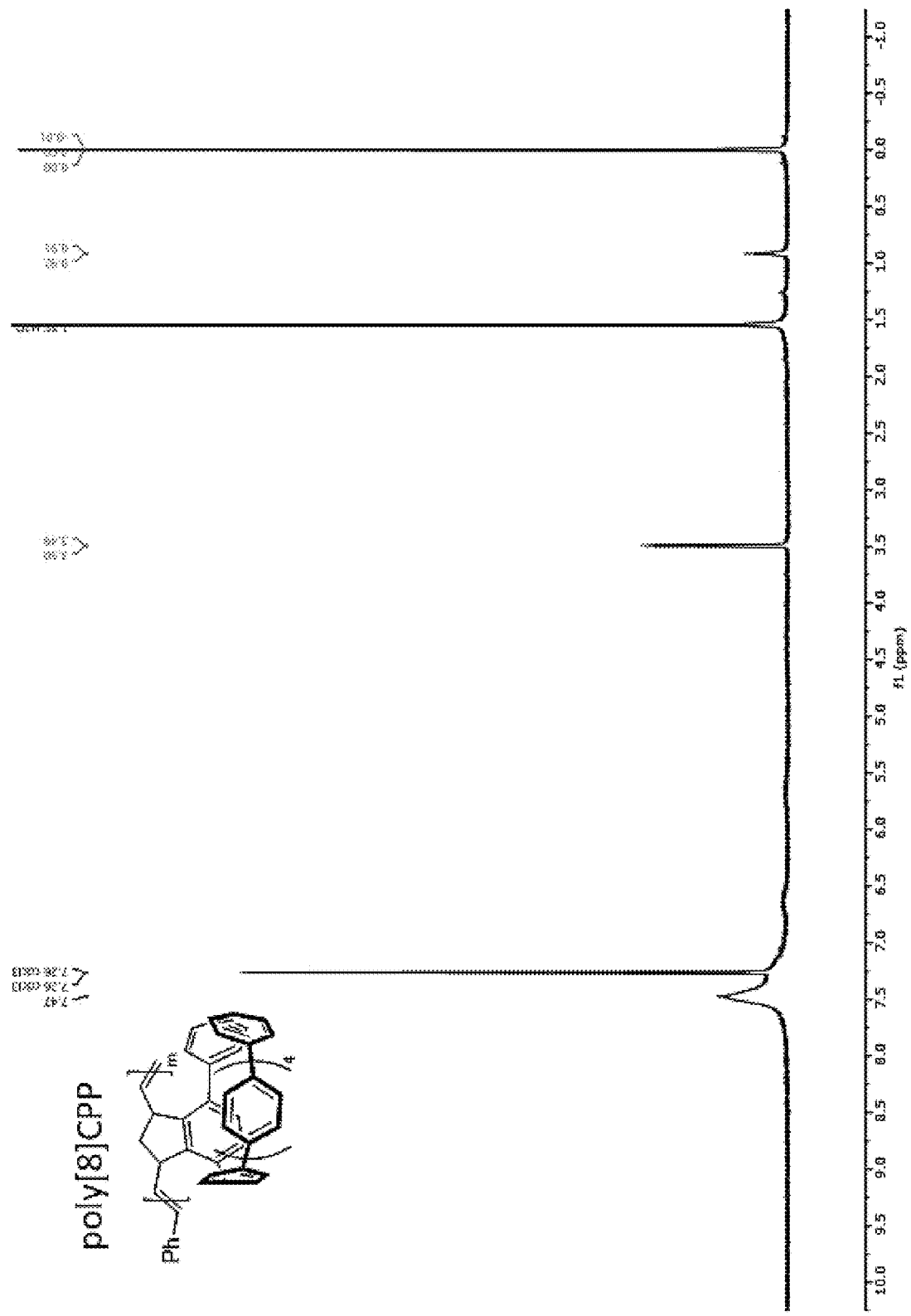
FIGS. 21A and 21B are proton NMR spectra of polymer embodiments obtained from polymerizing polymerizable nanohoop monomer 408 (FIG. 21A) and polymerizable nanohoop monomer 504 (FIG. 21 B).

In a representative example, polymerizable nanohoop monomer 408 was added to a small vial with a stir bar, placed under N$_2$, then dissolved in dry THF. A solution of bromopyridyl Grubbs G3 in THF was quickly added to the vial via syringe, and the reaction was stirred until all monomer is consumed. The reaction was quenched with ethyl vinyl ether, and the material was precipitated from cold methanol. The polymer (referred to herein as "poly[8]CPP") was collected by vacuum filtration. See FIG. 21A for the corresponding proton NMR spectrum.

Figure 21B:
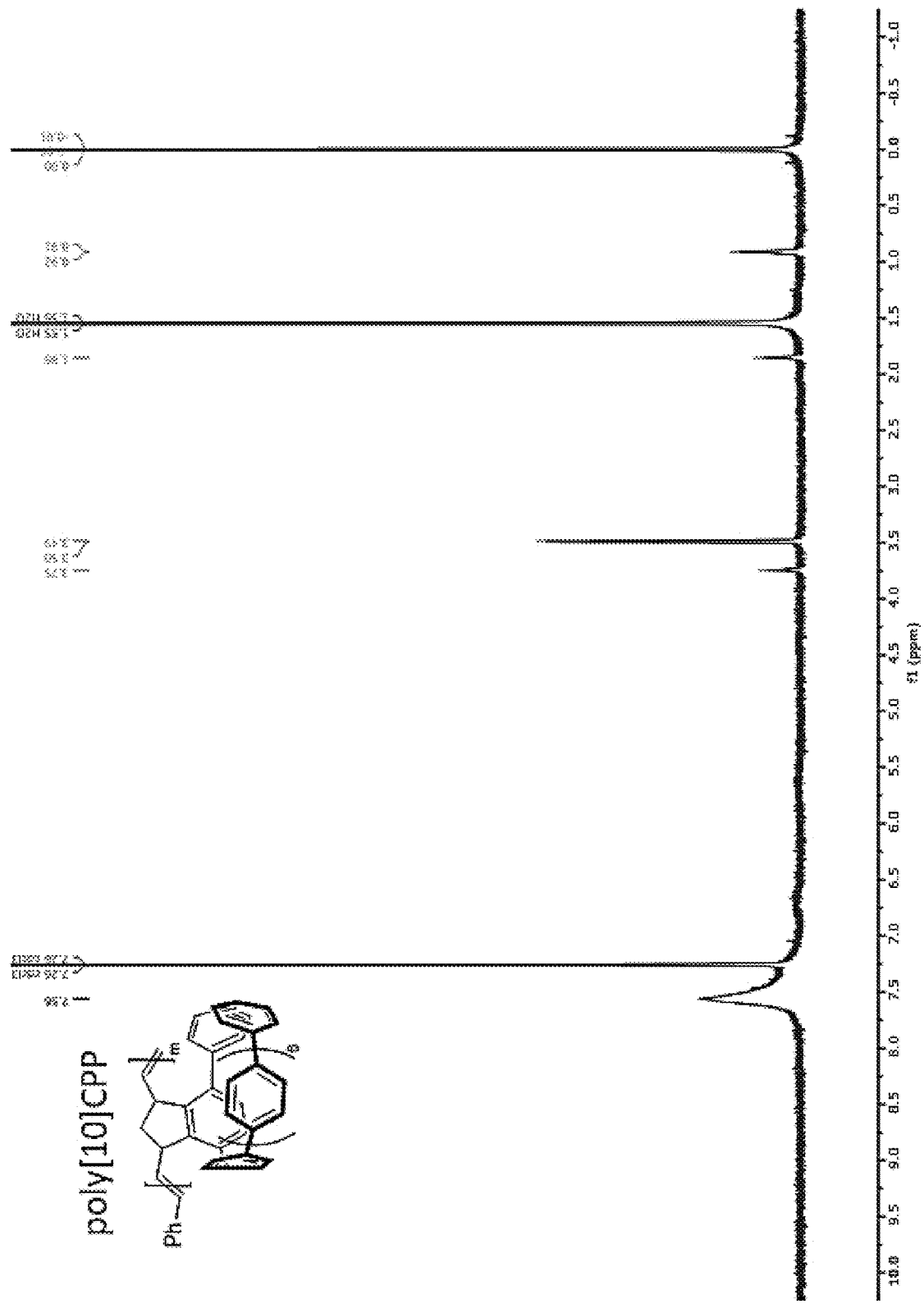

In another representative example, polymerizable nanohoop monomer 504 was added to a small vial with a stir bar, placed under N$_2$, then dissolved in dry THF. A solution of bromopyridyl Grubbs G3 in THF was quickly added to the vial via syringe, and the reaction was stirred until all monomer is consumed. The reaction was quenched with ethyl vinyl ether, and the material was precipitated from cold methanol. The polymer (referred to herein as "poly[10]CPP") was collected by vacuum filtration. See FIG. 21B for the corresponding carbon NMR spectrum For the polymers obtained from polymerizable nanohoop monomers 408 and 504, dispersity values around 1.3 according to gel permeation chromatography (GPC) analysis (Table 1). The polymers were well-soluble in common organic solvents such as chloroform and THF, in stark contrast to linear phenylenes which require solubilizing side chains. $^1$H NMR spectra of the polymers show broad multiplets characteristic of substituted [8]CPP and [10]CPP (at 7.48 and 7.55 ppm, respectively) and extremely broad/flat peaks in the alkyl and alkene regions, suggesting that the polymers, at least in some embodiments, are not stereoregular and likely contain a mix of cis and trans alkenes. In situ NMR spectroscopy revealed that both monomers are consumed at approximately the same rate (see FIGS. 5A and 5B). To probe the living nature of CPP-NB polymerization, polymerizable nanohoop monomer 408 was polymerized over a range of monomer-to-initiator ratios. GPC and dynamic light scattering (DLS) analysis of poly[8]CPP samples revealed a linear trend between monomer-to-initiator ratio and polymer molecular weight (see FIG. 6 and Table 1). These results indicate that not only can CPPs be kept intact throughout ROMP, but they can be polymerized in a living fashion.

Figure 7:
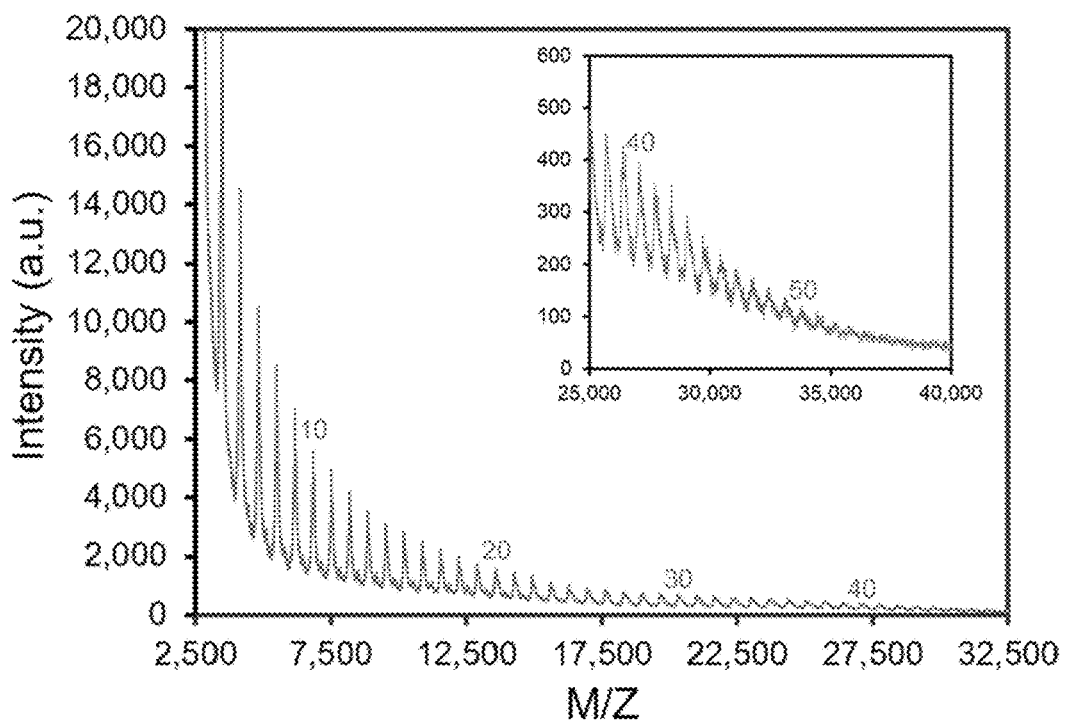
FIG. 7 shows the matrix-assisted laser desorption/ionization (MALDI) spectrum of a sample of poly[8]CPP, which shows consistent spacing of 673 Da between peaks; the number of repeat units (m) is labeled periodically above the corresponding peaks and for this sample (with Mw 7,800 Da measured by GPC and 13,100 Da measured by DLS) MALDI peaks are visible from about 2,500 to 35,000 Da.

To study the absolute molecular weight distributions of these polymers, several poly-CPP samples were analyzed by matrix-assisted laser desorption ionization (MALDI) mass spectrometry (see FIG. 7). In some embodiments, the wide range of polymer chain lengths present in the samples precluded quantitative analysis of the spectra; however, the uniform spacing between peaks corresponding with the monomer masses—673 Da for polymerizable nanohoop monomer 408 and 825 Da for polymerizable nanohoop monomer 504—further confirmed formation of the desired polymer structures with intact CPP units. Though the upper limits for achievable poly-CPP molecular weights were not tested in this example, MALDI peaks corresponding to polymer chains containing 50 or more repeat units were observed.

TABLE 1

GPC and DLS characterization of representative poly-CPP samples. Polymerizations were conducted using 10-30 mg monomer, and yields were typically quantitative.

| | GPC Analysis | | DLS Analysis | | |
|---|---|---|---|---|---|
| Sample Identity | $M_w$ (Da) | Đ ($M_w/M_n$) | $M_w$ (Da) | $R_h$ (nm) | Dispersity |
| poly[8]CPP | 1,300 | 1.24 | 4,100 | 1.1 | 47% |
| poly[8]CPP | 7,800 | 1.30 | 13,100 | 1.8 | 24% |
| poly[8]CPP | 9,000 | 1.49 | 17,100 | 2.0 | 25% |

TABLE 1-continued

GPC and DLS characterization of representative poly-CPP samples. Polymerizations were conducted using 10-30 mg monomer, and yields were typically quantitative.

| | GPC Analysis | | DLS Analysis | | |
|---|---|---|---|---|---|
| Sample Identity | $M_w$ (Da) | Ð ($M_w/M_n$) | $M_w$ (Da) | $R_h$ (nm) | Dispersity |
| poly[8]CPP | 13,000 | 1.33 | 23,600 | 2.3 | 25% |
| poly[8]CPP | 19,300 | 1.63 | 38,600 | 2.9 | 15% |
| 3:1 poly[8]CPP-random-[10]CPP | 13,600 | 1.32 | 21,000 | 2.2 | 13% |
| 1:1 poly[8]CPP-random-[10]CPP | 17,600 | 1.34 | 27,500 | 2.5 | 21% |
| 1:1 poly[8]CPP-random-[10]CPP | 14,600 | 1.52 | 30,000 | 2.5 | 24% |
| 1:3 poly[8]CPP-random-[10]CPP | 17,400 | 1.33 | 24,500 | 2.3 | 12% |
| poly[10]CPP | 16,900 | 1.27 | 23,600 | 2.3 | 20% |

Example 10

In this example, the optical properties of polymer were evaluated. In particular, THF solutions of poly[8]CPP and poly[10]CPP were examined using UV-vis absorption and fluorescence spectroscopy. Absorbance and emission spectra of the homopolymers, like those of the monomers, show little change from the spectra of the parent CPPs (see FIGS. 2 and 3). Fluorescence quantum yields were determined to be 27% and 63%.

Figure 8:
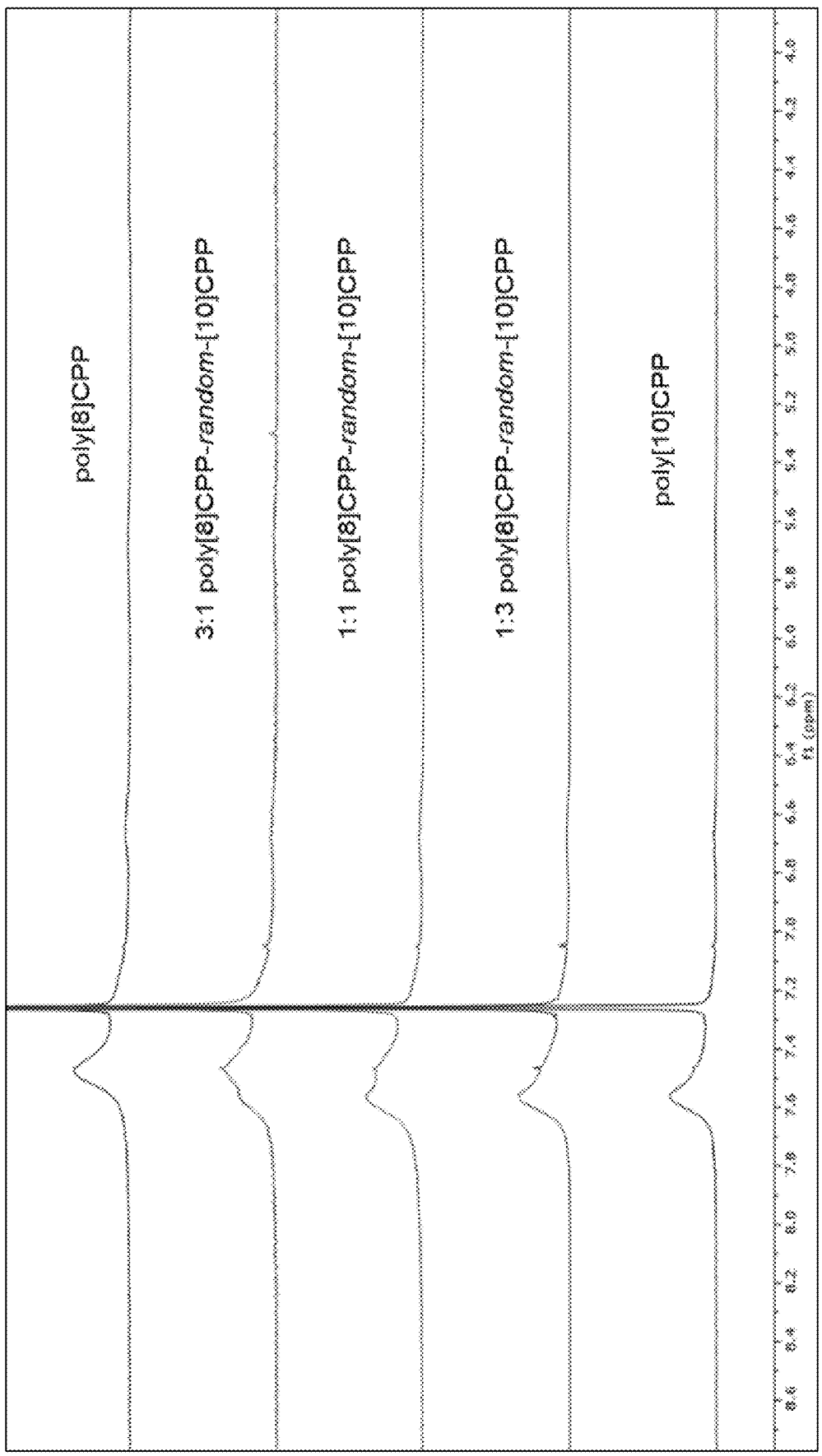
FIG. 8 shows stacked nuclear magnetic resonance (NMR) spectra for (i) poly[8]CPP, (ii) three random copolymers with varying ratios of polymerizable nanohoop monomer 408 and polymerizable nanohoop monomer 504, and (iii) poly[10]CPP.
Figure 9:
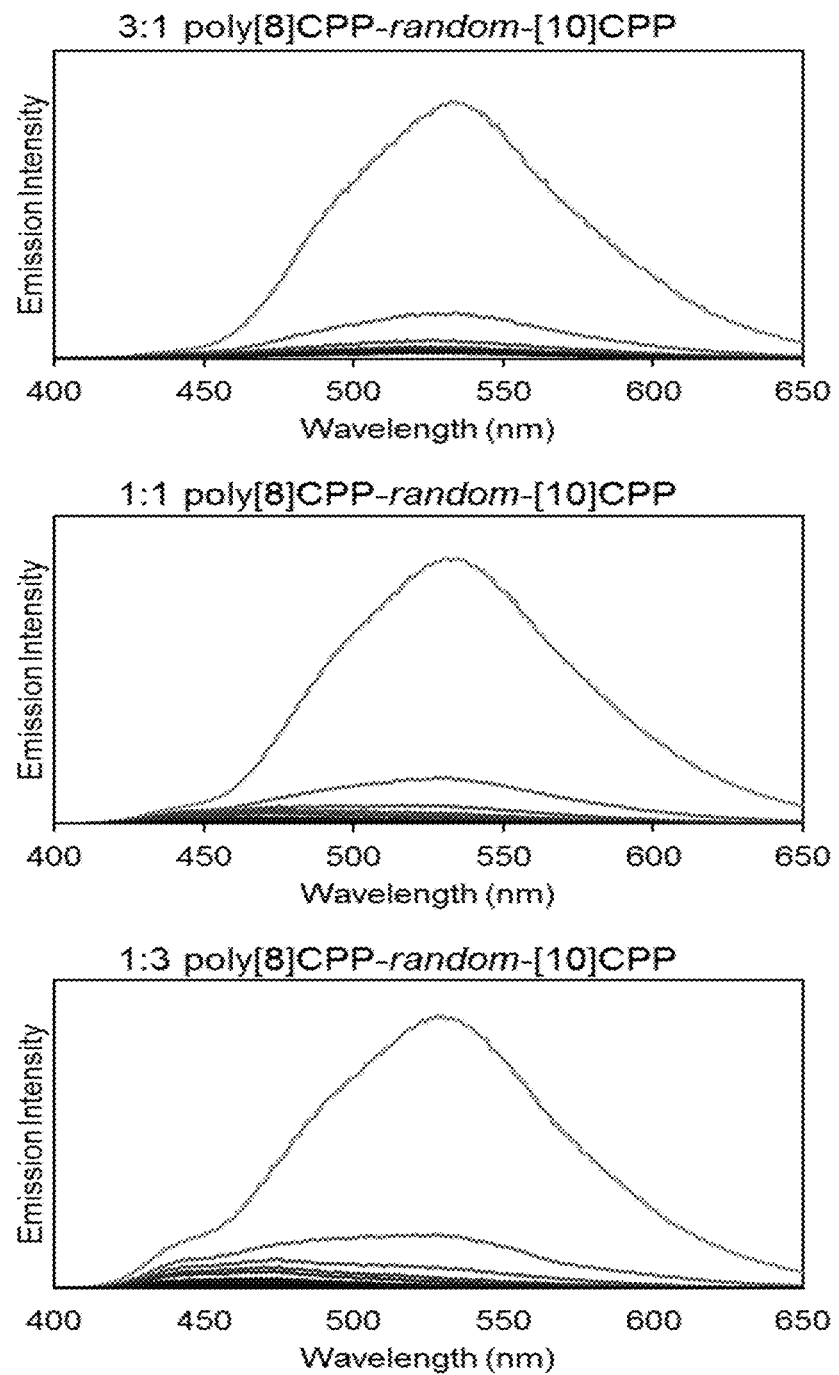
FIG. 9 shows the emission spectra and quenching response to $C_{60}$ of each of the three random copolymers of FIG. 8.
Figure 10:
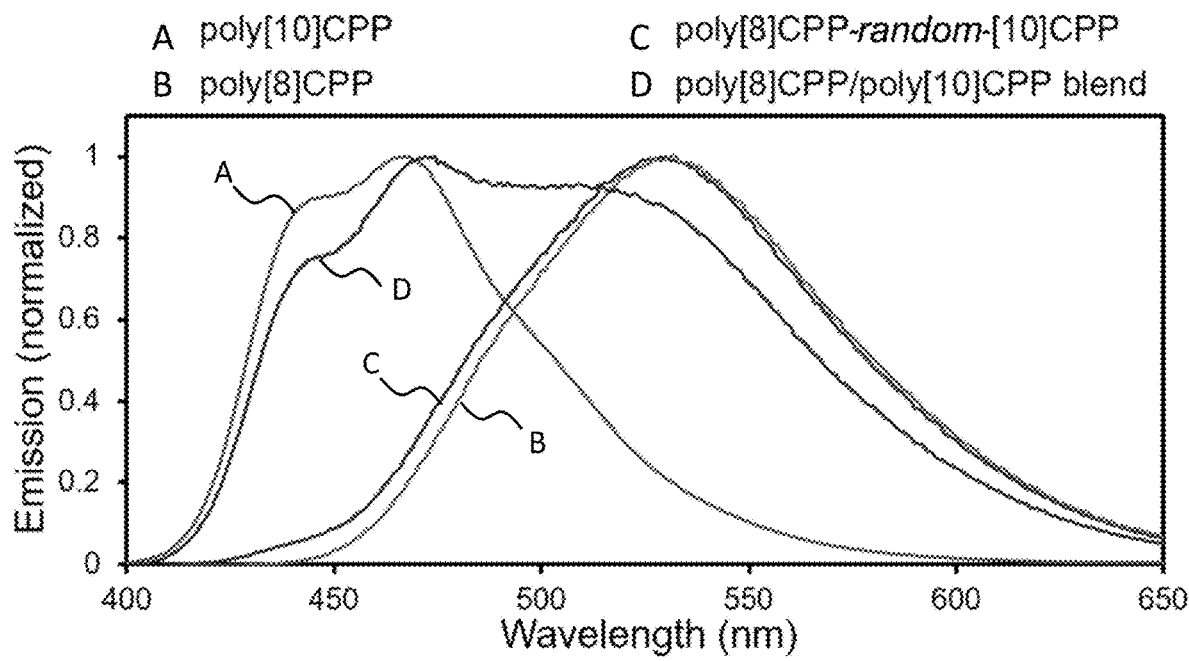
FIG. 10 show fluorescence emission spectra of poly-CPPs, which shows that a poly[8]CPP/poly[10]CPP blend exhibits characteristics of both poly[8]CPP and poly[10] CPP in its emission profile, whereas the emission of poly [8]CPP-random-[10]CPP resembles the emission of poly[8] CPP.

The tunability of the fluorescence emission of poly-CPPs also was evaluated. In one example, polymerizable nanohoop monomer 408 and polymerizable nanohoop monomer 504 units were combined in one polymer to determine if this would produce an additive emission profile with features from both fluorophores. A copolymer was prepared by premixing equimolar amounts of polymerizable nanohoop monomer 408 and polymerizable nanohoop monomer 504 before addition of initiator to the reaction. Incorporation of both units in the resultant polymer, poly[8]CPP-random-[10]CPP, was confirmed by $^1$H NMR and emission intensity analysis (see FIGS. 8 and 9, respectively). In this embodiment, the fluorescence emission of this polymer closely resembled the emission of polymerizable nanohoop monomer 408 with a major peak at 529 nm (see FIG. 10). Only a slight shoulder extending from about 415 to 520 nm revealed any contribution from the polymerizable nanohoop monomer 504 units to the overall emission profile. For comparison, a blend of poly[8]CPP and poly[10]CPP homopolymers in THF was prepared. This poly[8]CPP/poly[10]CPP blend displays clear emission contributions from both types of polymers, indicating that the two types of homopolymers are electronically independent in the blend. In contrast, the unexpected emission of copolymerized polymerizable nanohoop monomer 408 and polymerizable nanohoop monomer 504 suggests that when these hoops are covalently linked in close proximity, interactions emerge that are not observed among individual CPP molecules or blended homopolymers. In poly[8]CPP-random-[10]CPP, the fluorescence of the smaller hoops dominates the overall emission spectrum, indicating energy transfer between the hoop units. A related effect was recently observed in a comparative heterocatenane composed of [9]CPP and [12]CPP. The observance of energy transfer in CPP copolymers suggests that CPP units can play a role in advanced emissive materials composed of multiple fluorophores.

Example 11

Figure 11:
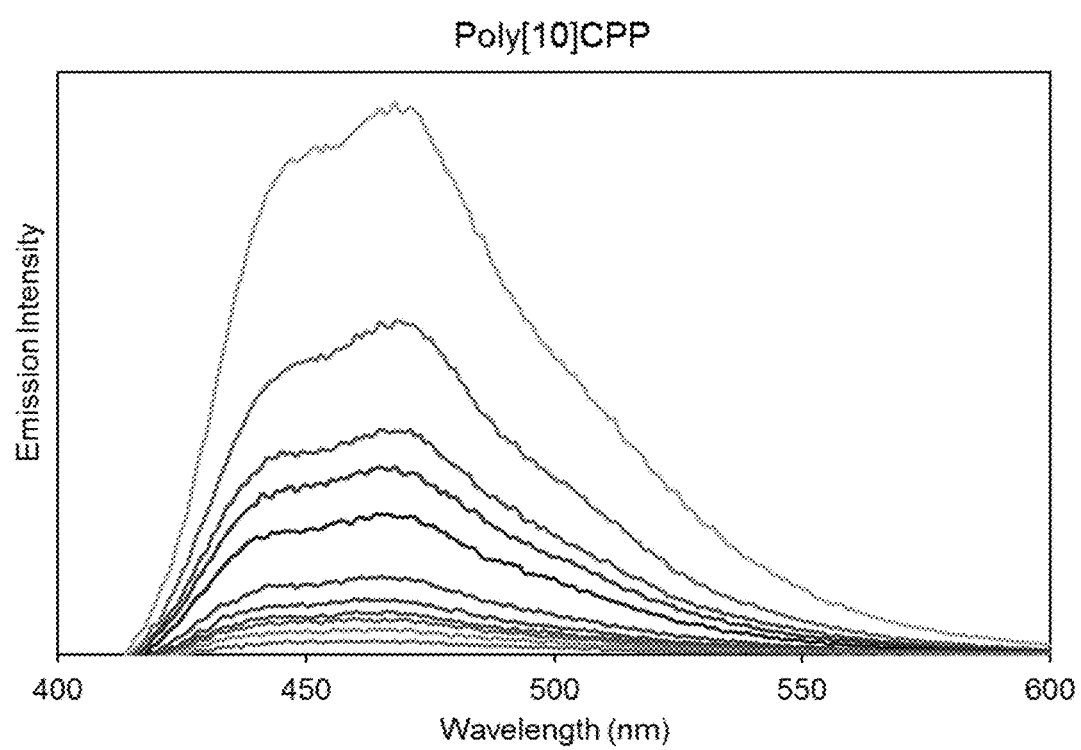
FIG. 11 shows fluorescence quenching of poly[10]CPP by Cso, wherein the arrow indicates direction of increasing $C_{60}$ concentration; fluorescence emission was measured in toluene with excitation at 340 nm and quenching is also visibly apparent when $C_{60}$ is added to polymerizable nanohoop monomer 504 or poly[10]CPP.
Figure 12:
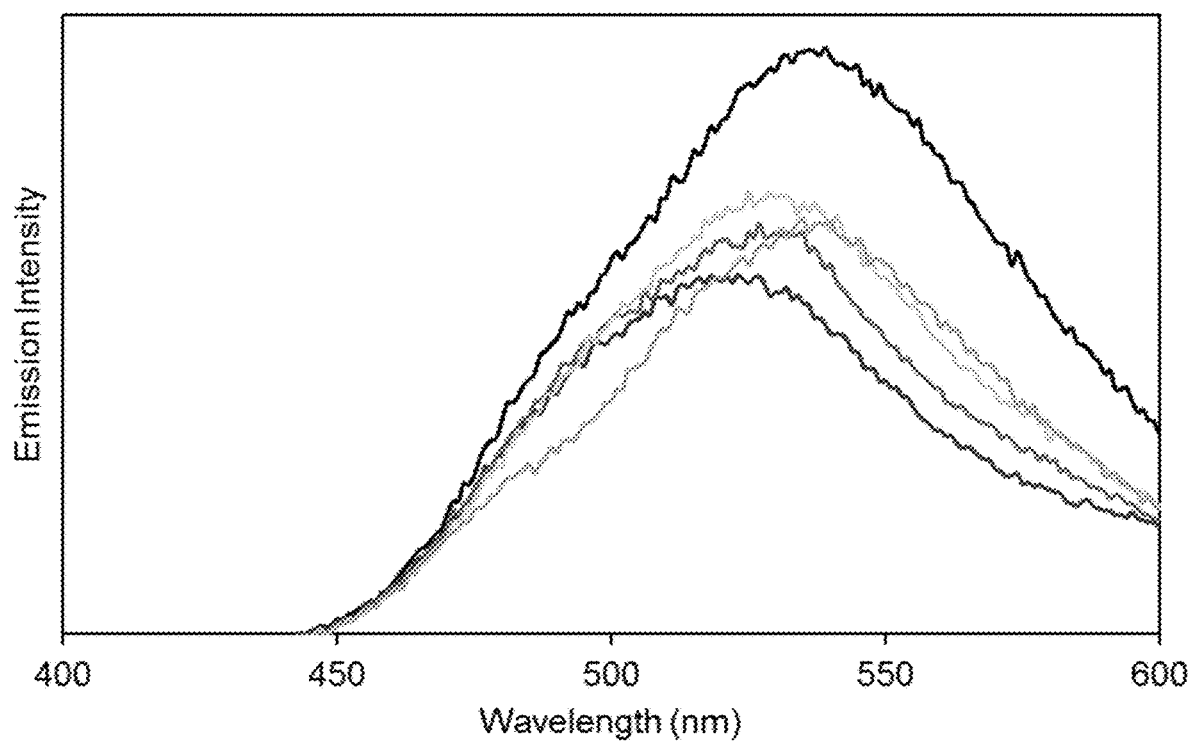
FIG. 12 shows that a slight decrease in fluorescence emission of poly[8]CPP was observed on addition of $C_{60}$ due to dynamic quenching, but the emission intensity leveled off after further $C_{60}$ addition; lighter gray traces correspond to higher concentrations of Cso.
Figure 13A:
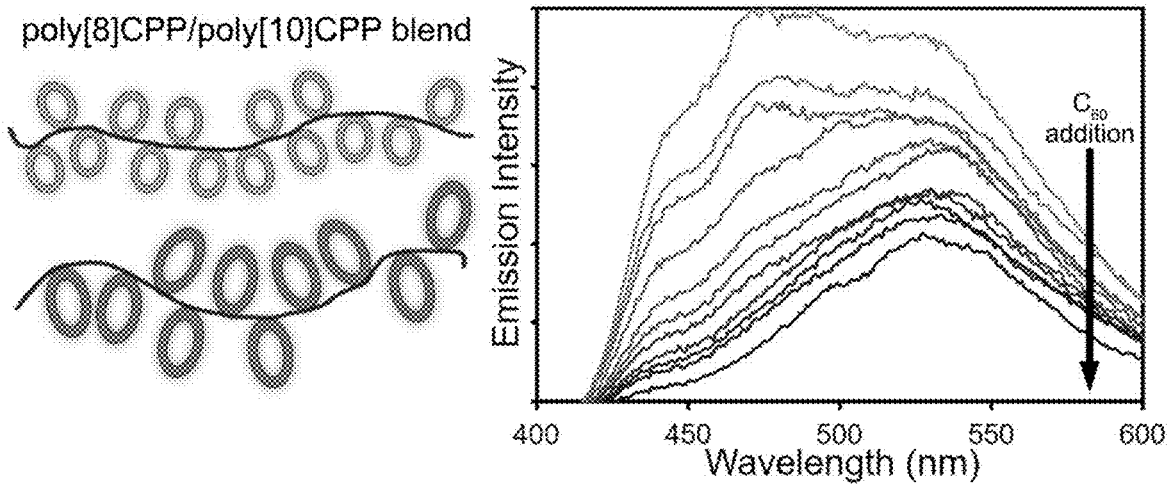
FIGS. 13A and 13B show poly[8]CPP/poly[10]CPP blend (FIG. 13A) and poly[8]CPP-random-[10]CPP (FIG. 13B), represented pictorially on the left, exhibit drastically different emission profiles and responses to the addition of Cso.
Figure 13B:
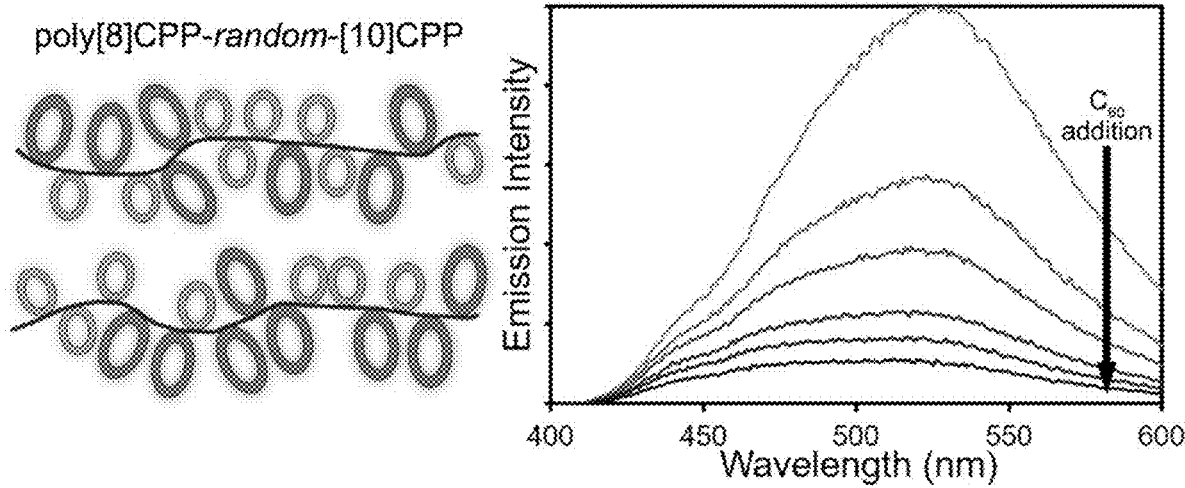

In this example, fluorescence quenching experiments were used to investigate the host-guest interactions of poly-CPPs with $C_{60}$, using solutions of the polymers in toluene. Poly[10]CPP exhibits the characteristic fluorescence quenching of [10]CPP by $C_{60}$ (see FIG. 11), whereas poly[8]CPP, like [8]CPP, has no inherent affinity for $C_{60}$ and undergoes only minor dynamic quenching from $C_{60}$ addition (see FIG. 12). Upon $C_{60}$ addition to the poly[8]CPP/poly[10]CPP blend, the region of the emission spectrum attributed to the contribution from poly[10]CPP, from around 420 nm to 500 nm, undergoes the greatest quenching effect from $C_{60}$, while the emission peak at 528 nm attributed to the emission contribution from poly[8]CPP persists (see FIG. 13A). The emission maximum of the blend can be gradually shifted to longer wavelengths by selective quenching of the emission of poly[10]CPP by $C_{60}$. Aliquots of $C_{60}$ were then added to a solution of poly[8]CPP-random-[10]CPP, which resulted in a gradual fluorescence quenching across the entire spectrum (see FIG. 13B). Very similar emission and quenching was observed in copolymer samples with 3:1 and 1:3 molar ratios of polymerizable nanohoop monomer 408 and polymerizable nanohoop monomer 504 (see FIGS. 8 and 9). The difference in quenching between the poly[8]CPP/poly[10]CPP blend and poly[8]CPP-random-[10]CPP reinforces that the close covalent linkage of multiple sizes of CPPs is responsible for these emergent properties.

Example 12

In this example, representative polymers were characterized using different characterization techniques. Results are presented below.

X-Ray Crystallography Data

Single crystals suitable for crystallographic analysis were grown from slow evaporation of a solution of 402 in DCM/hexanes and slow diffusion of pentane into solutions of 408 and 504 in THF. Crystal data has been deposited to the Cambridge Crystallographic Database with CCDC numbers 1949617, 1949616, and 1949615.

Diffraction intensities for 402, 408 and 504 were collected at 173 K on a Bruker Apex2 CCD diffractometer using CuKα radiation, λ=1.54178 Å. Space groups were determined based on systematic absences. Absorption corrections were applied by SADABS. Structures were solved by direct methods and Fourier techniques and refined on $F^2$ using full matrix least-squares procedures. All non-H atoms were refined with anisotropic thermal parameters. H atoms in all structures were refined in calculated positions in a rigid group model. The structure of 408 was determined in non-centrosymmetrical space group symmetry R3c, but not in possible centro-symmetrical space group R-3c. The refinement in non-centrosymmetrical space group symmetry R3c shown that the Flack parameter is close to zero, but not to 0.5 as could be expected if the centro-symmetrical space group R-3c is correct. Crystals of 408 are formed as thin strips and give very weak X-ray diffraction at high angles. Even using a strong Incoatec IμS Cu source for 408 it was possible to collect data only up to 2 $\theta_{max}$=98.44°. However the collected data provide an appropriate number of measured reflections per a number of refined parameters, 4073/472. In both 408 and 504 structures solvent pentane molecules fill out empty space in the packing and in the hoops and are highly disordered. These disordered solvent molecules were treated by SQUEEZE. The corrections of the X-ray data by SQUEEZE are 760 and 480 electron/cell; the required values are 756 and 336 electron/cell for eighteen and eight pentane molecules in the full unit cells, respectively in 408 and 504. The five-member ring in 408 is disordered over two positions with opposite orientations as well. Resolution for 408 and 504 structures is relatively low due to a lot of disordered fragments in the structures and weak X-ray diffraction at high angles, but the found X-ray structures clearly shown the structure of the hoops in these compounds. All calculations were performed by the Bruker SHELXL-2014 package.

Crystallographic Data for 402: $C_{25}H_{22}Br_2O_2$, M=514.24, 0.11×0.08×0.06 mm, T=173(2) K, Monoclinic, space group P2$_1$/c, a=12.3702(5) Å, b =15.2429(6) Å, c=12.0344(4) Å, β=112.703(1)°, V=2093.36(14) Å3, Z=4, D$_c$=1.632 Mg/m3, μ(Cu)=5.058 mm-1, F(000)=1032, 2 $\theta_{max}$=133.31°, 16491 reflections, 3694 independent reflections [$R_{int}$=0.0496], R1=0.0313, wR2=0.0848 and GOF=1.044 for 3694 reflections (262 parameters) with I>2 σ(1), R1=0.0344, wR2=0.0870 and GOF=1.044 for all reflections, max/min residual electron density +0.573/−0.507 eÅ$^{-3}$. See FIG. 14.

Crystallographic Data for 408: $C_{58}H_{48}$, $C_{53}H_{36}$·$(C_5H_{12})$, M=744.96, 0.09×0.08×0.01 mm, T=173(2) K, Trigonal, space group R3c, a=16.3432(5) Å, b=16.3432(5) Å, c=80.413(4) Å, V=18600.8(14) Å3, Z=18, D$_c$=1.197 Mg/m3, μ(Cu)=0.508 mm-1, F(000)=7128, 2 $\theta_{max}$=98.44°, 25725 reflections, 4073 independent reflections [$R_{int}$=0.0604], R1=0.0534, wR2=0.1340 and GOF=1.085 for 4073 reflections (472 parameters) with I>2 σ(1), R$^1$=0.0688, wR2 =0.1424 and GOF=1.087 for all reflections, max/min residual electron density +0.140/−0.137 eÅ$^{-3}$. See FIG. 15.

Crystallographic Data for 504: $C_{75}H_{68}$, $C_{65}H_{44}$·2$(C_5H_{12})$, M=969.29, 0.11×0.08×0.06 mm, T=173(2) K, Monoclinic, space group P2$_1$/c, a=6.5747(3) Å, b =28.3155(16) Å, c=32.6239(17) A, β=91.334(4)°, V=6071.8(5) Å3, Z=4, D$_c$=1.060 Mg/m3, μ(Cu)=0.447 mm-1, F(000)=2072, 2 $\theta_{max}$=133.40°, 46166 reflections, 10685 independent reflections [$R_{int}$=0.0443], R1=0.0507, wR2=0.1396 and GOF=1.051 for 10685 reflections (586 parameters) with I>2 σ(1), R1=0.0617, wR2=0.1461 and GOF=1.051 for all reflections, max/min residual electron density +0.391/−0.198 eÅ$^{-3}$. See FIG. 16.

Kinetics

Figure 5A:
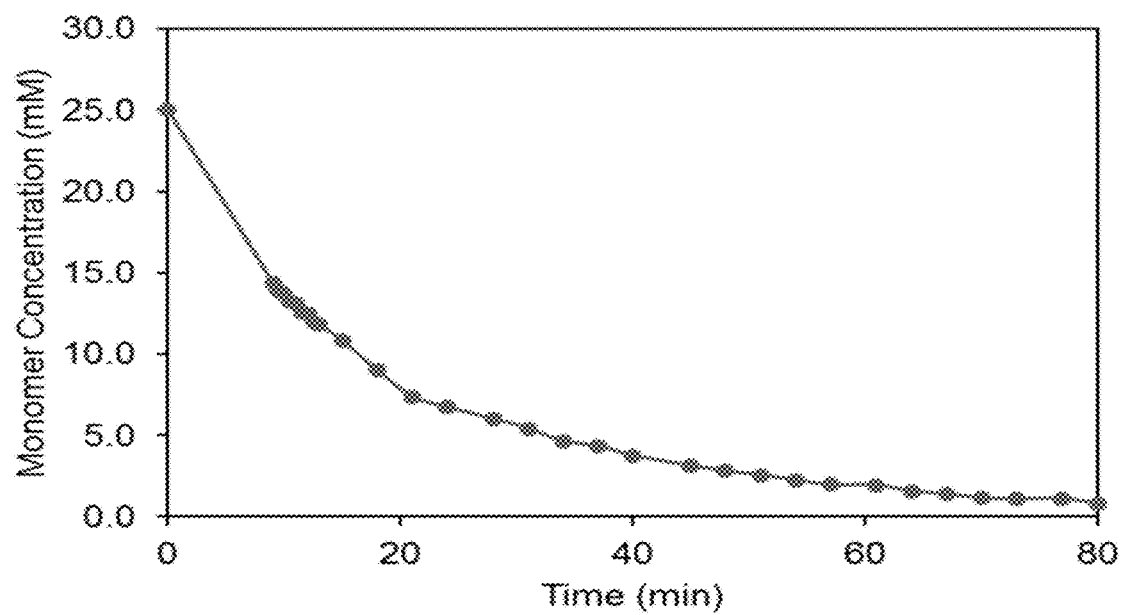
FIGS. 5A and 5B are plots showing the conversion of polymerizable nanohoop monomer 408 (FIG. 5A) and polymerizable nanohoop monomer 504 (FIG. 5B) to polymer over time; wherein, based on spectra taken of room temperature polymerizations, both monomers were typically consumed within about 30 minutes.
Figure 5B:
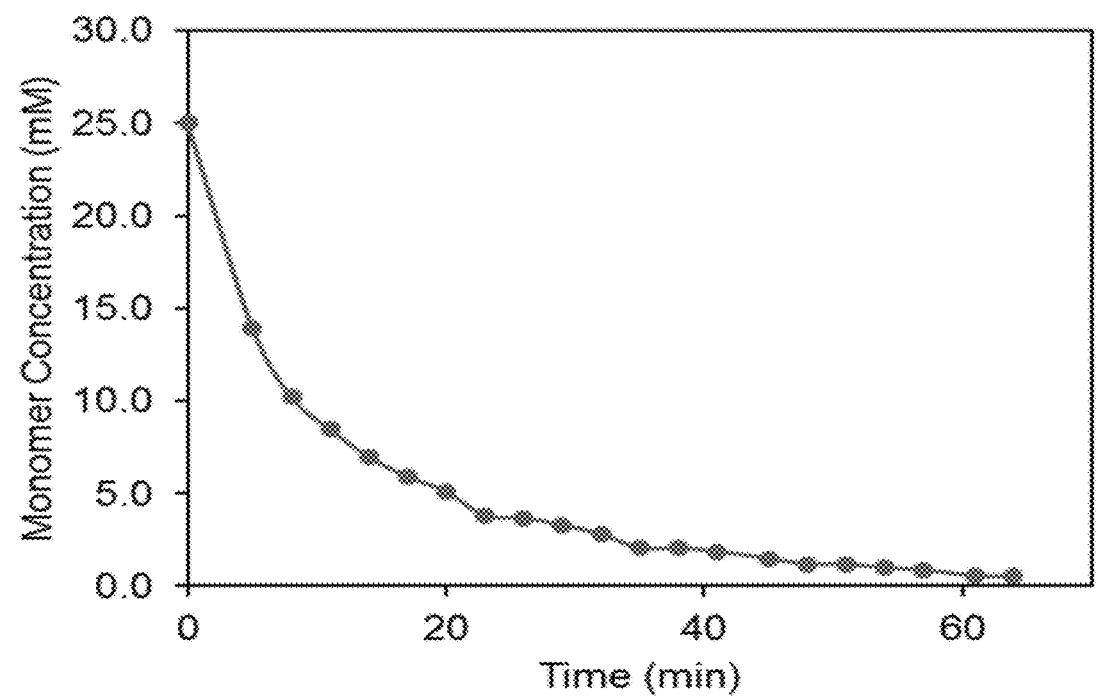
Figure 6:
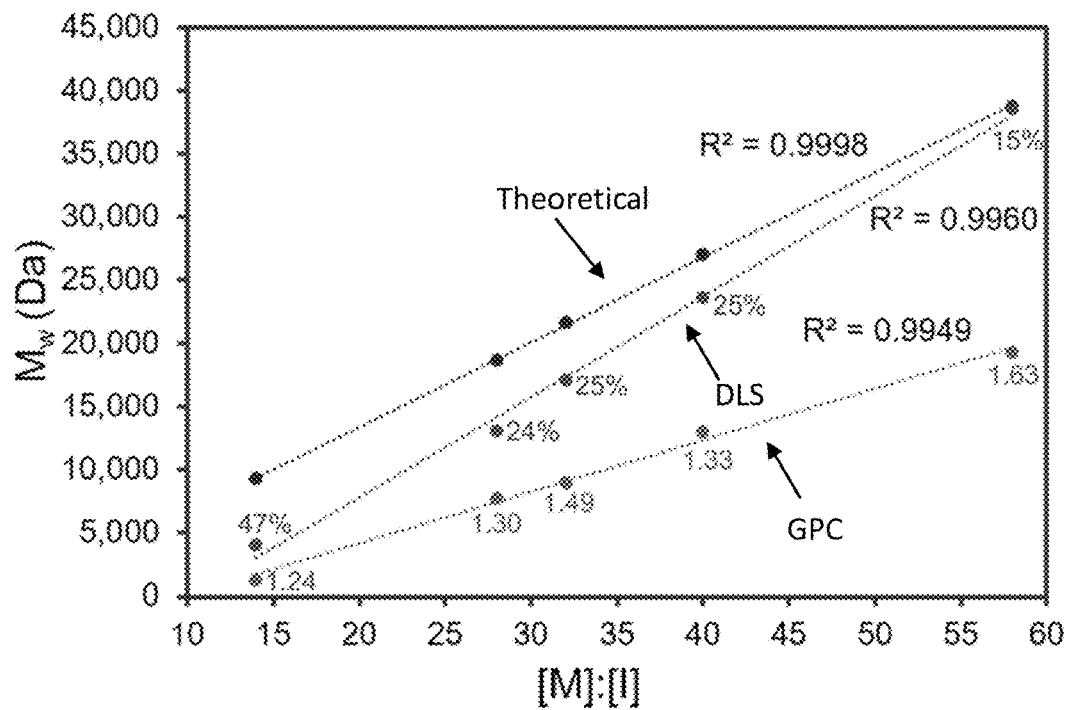
FIG. 6 shows poly[8]CPP molecular weight values measured by gel permeation chromatography (GPC) and dynamic light scattering (DLS) scale linearly with the molar ratio of monomer to initiator; the dispersity values determined by GPC and DLS are indicated next to the respective data points.

The 90° pulse width was calibrated for both monomers, and a 90° pulse width of 11.25 μs at −11.43 dB was used. Longitudinal relaxation time constants (T1) for both monomers were determined by inversion-recovery to be approximately 1 s, so a relaxation delay of 5 s was used for all acquisitions. Kinetic experiments were conducted in THF-d$_8$ with concentrations of 32 mM monomer, 3.2 mM Grubbs G3 initiator, and approximately 21 mM dimethyl sulfone (δ2.86 ppm) as an internal standard. A proton spectrum was acquired for each sample before Grubbs G3 addition to determine the initial amount of monomer relative to dimethyl sulfone. Each sample was kept in an ice bath during Grubbs G3 addition then shaken and inserted into the NMR spectrometer. Spectra were acquired every 3 minutes until the polymerization was complete. All spectra were acquired at 10° C. Peaks at 4.32 ppm and 4.33 ppm were used to track consumption over time of polymerizable nanohoop monomer 408 and polymerizable nanohoop monomer 504, respectively. Toward the end of the polymerizations, however, the baseline around these peaks was no longer flat, interfering with accurate integration. Therefore, line fitting excluded data points after these times although small amounts of monomer remained. Results of conversion of the monomers to polymers over time are shown in FIGS. 5A and 5B.

In view of the many possible embodiments to which the principles of the present disclosure may be applied, it should be recognized that the illustrated embodiments are only preferred examples and should not be taken as limiting. Rather, the scope is defined by the following claims. We therefore claim as our invention all that comes within the scope and spirit of these claims.

We claim:

1. A polymer having a structure according to Formula I

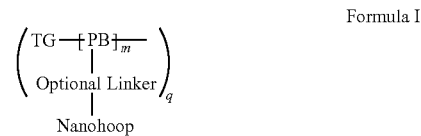

Formula I wherein PB is a polymer backbone; TG is a terminating group; the optional linker is selected from aliphatic, heteroaliphatic, haloaliphatic, haloheteroaliphatic, aromatic, or an organic functional group; the nanohoop comprises six or more aromatic ring systems, wherein each aromatic ring is directly bound to at least two other rings of the nanohoop by two separate single covalent bonds positioned para, ortho, or meta relative to one another, and wherein the nanohoop is not linearly conjugated with the PB; m is an integer ranging from two or greater; and q is an integer selected from 1 or 2.

2. The polymer of claim 1, wherein the TG is an aromatic ring.

3. The polymer of claim 2, wherein the aromatic ring is a phenyl ring.

4. The polymer of claim 1, wherein the optional linker is not present and the PB is covalently attached to the nanohoop through two points of attachment.

5. The polymer of claim 4, wherein the PB is a five-membered ring and two adjacent carbon atoms of the five-membered ring are attached to two adjacent carbon atoms of the nanohoop.

6. The polymer of claim 1, wherein the optional linker is not present and the PB is covalently attached to the nanohoop through one point of attachment.

7. The polymer of claim 1, wherein q is 2 and each PB is different from the other.

8. The polymer of claim 1, wherein the polymer has a structure according to Formula II

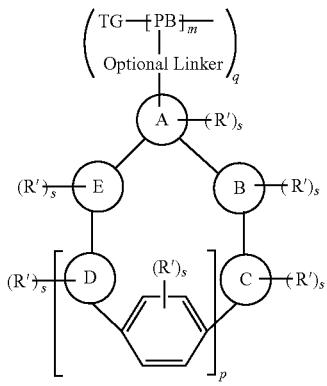

Formula II wherein each of rings A, B, C, D, and E independently are aromatic ring systems; each R' independently is a substituent other than hydrogen; each s independently is an integer selected from 0 to 10; and p is an integer selected from 1 to 1000.

9. The polymer of claim 8, wherein each of rings A, B, C, D, and E independently are aryl or heteroaryl.

10. The polymer of claim 8, wherein each of rings A, B, C, D, and E independently are phenyl or pyridinyl.

11. The polymer of claim 8, wherein each R' independently is selected from aliphatic, heteroaliphatic, haloaliphatic, aromatic, or an organic functional group.

12. The polymer of claim 1, wherein the polymer has a structure according to Formula III or IV

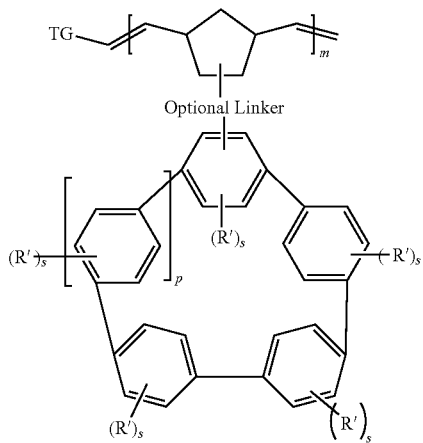

Formula III

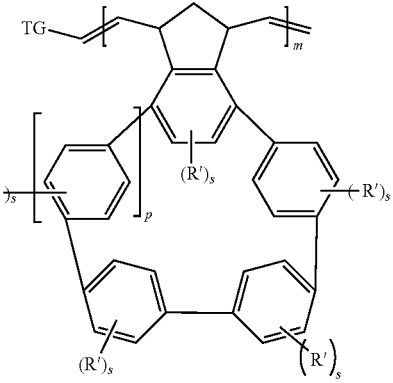

Formula IV wherein each R' independently is a substituent other than hydrogen; each s independently is an integer selected from 0 to 10; and p is an integer selected from 1 to 1000.

13. The polymer of claim 12, wherein each R' independently is selected from aliphatic, aryl, heteroaryl, halogen, an electron-accepting group, an electron-donating group, or any combination thereof.

14. The polymer of claim 1, wherein the polymer is

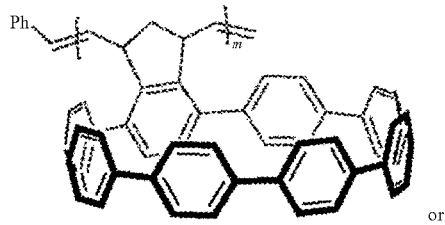

or

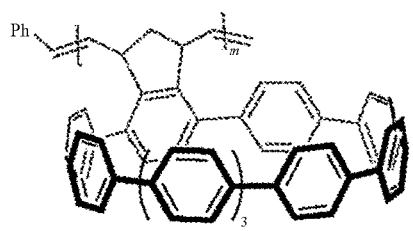

15. A method, comprising exposing one or more polymerizable nanohoop monomers to conditions that promote ring opening metathesis polymerization, reversible addition-fragmentation chain transfer, anionic polymerization, or condensation polymerization between the one or more polymerizable nanohoop monomers to thereby provide the nanohoop-functionalized polymer according to claim 1, wherein bonds are formed between polymerizable functional groups of the one or more polymerizable nanohoop monomers; wherein the one or more polymerizable nanohoop monomers independently have a structure according to Formula V

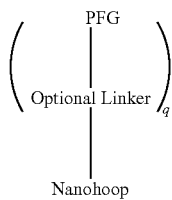

Formula V wherein each PFG independently is selected from a norbornene, an acrylate, a methacrylate, a methyacrylamide, a stryene, a diene, vinyl acetate, n-vinylpyrrolidone, an aldehyde, an epoxide, an acrylonitrile, a cyanoacrylate, an alcohol, a carboxylic acid, an amine, or an ether;

the optional linker is selected from aliphatic, heteroaliphatic, haloaliphatic, haloheteroaliphatic, aromatic, or an organic functional group;

the nanohoop comprises six or more aromatic ring systems and wherein each aromatic ring is directly bound to at least two other rings of the nanohoop by two separate single covalent bonds positioned para, ortho, or meta relative to one another; and q is 1 or 2.

16. The method of claim 15, wherein the method comprising exposing the one or more polymerizable nanohoop monomers to a ruthenium-based catalyst to promote a ring opening metathesis polymerization between the polymerizable functional groups of the one or more polymerizable nanohoop monomers and wherein the polymerizable nanohoop monomer has a structure according to Formula VII or VIII

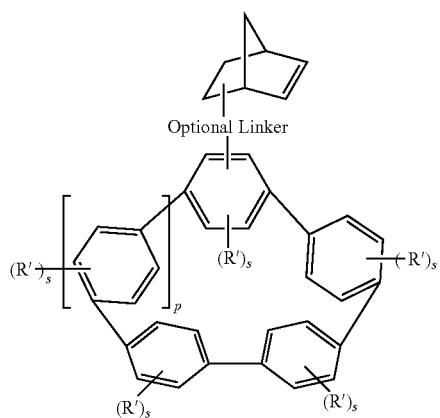

Formula VII

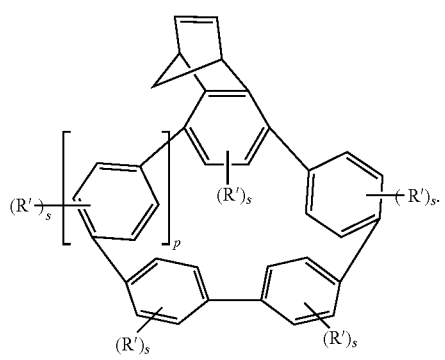

Formula VIII

* * * * *